United States Patent [19]

Matsuo et al.

[11] Patent Number: 5,994,378
[45] Date of Patent: Nov. 30, 1999

[54] THIAZOLYLBENZOFURAN DERIVATIVES AND PHARMACEUTICAL COMPOSITIONS CONTAINING THEM

[75] Inventors: Masaaki Matsuo, Toyonaka; Kazuo Okumura, Osaka; Shinji Shigenaga; Hiroaki Nishimura, both of Kobe; Hiroshi Matsuda, Osaka; Daijiro Hagiwara, Moriguchi; Tadashi Terasaka, Ikeda, all of Japan

[73] Assignee: Fujisawa Pharmaceutical Co., Ltd., Osaka, Japan

[21] Appl. No.: 09/101,766

[22] PCT Filed: Jan. 17, 1997

[86] PCT No.: PCT/JP97/00073

§ 371 Date: Jul. 21, 1998

§ 102(e) Date: Jul. 21, 1998

[87] PCT Pub. No.: WO97/27190

PCT Pub. Date: Jul. 31, 1997

[30] Foreign Application Priority Data

Jan. 22, 1996 [GB] United Kingdom ............... 9601235
Jul. 18, 1996 [AU] Australia ............................ 1111

[51] Int. Cl.$^6$ ................... C07D 417/04; A01K 31/42
[52] U.S. Cl. ................... 514/365; 548/181; 548/205
[58] Field of Search .................... 548/181, 205; 514/305

[56] References Cited

U.S. PATENT DOCUMENTS 5,296,495  3/1994  Matsuo et al. .

FOREIGN PATENT DOCUMENTS 07179856  7/1995  Japan ...................... 548/200

*Primary Examiner*—Robert Gerstl
*Attorney, Agent, or Firm*—Oblon, Spivak, McClelland, Maier & Neustadt, P.C.

[57] ABSTRACT

This invention relates to novel thiazolylbenzofuran derivatives of formula (I) wherein $R^1$ is lower alkyl, L is single bond or lower alkylene optionally substituted with aryl, oxo or hydroxy, and Q is a heterocyclic group optionally substituted with one or more suitable substituent(s); or lower alkoxy substituted with aryl which is substituted with one or more suitable substituent(s) and at least one of which is lower alkoxy optionally substituted with cyano, protected carboxy, carboxy, lower alkylene, a heterocyclic group optionally substituted with oxo, or amidino optionally substituted with hydroxy or lower alkoxy, or its salt, which possess activities as leukotriene and SRS-A antagonists or inhibitors.

8 Claims, No Drawings

THIAZOLYLBENZOFURAN DERIVATIVES AND PHARMACEUTICAL COMPOSITIONS CONTAINING THEM

This invention relates to novel compounds and pharmaceutically acceptable salts thereof.

More particularly, it relates to new thiazolylbenzofuran derivatives and pharmaceutically acceptable salts thereof, which have activities as leukotriene and Slow Reacting Substance of Anaphylaxis (hereinafter, SRS-A) antagonists or inhibitors, to processes for preparation thereof, to a pharmaceutical composition comprising the same, and to methods of using the same therapeutically in the prevention and/or treatment of allergy or inflammation in human beings or animals.

One object of this invention is to provide new and useful thiazolylbenzofuran derivatives and pharmaceutically acceptable salts thereof, which possess activities as leukotriene and SRS-A antagonists or inhibitors.

Another object of this invention is to provide processes for the preparation of said derivatives and salts thereof.

A further object of this invention is to provide a pharmaceutical composition comprising, as an active ingredient, said thiazolylbenzofuran derivatives and pharmaceutically acceptable salt thereof.

Still further object of this invention is to provide a therapeutical method for the prevention and/or treatment of allergy or inflammation, and more particularly of asthma, psoriasis, hepatitis, bronchitis, gastritis, esophagitis, pancreatitis, arthritis, nephritis, inflammatory bowel disease, shock [e.g., septic shock, anaphylactic shock, etc.], arteriosclerosis, myocardial infarction, cerebral vasospasm, rhinitis, conjunctivitis, eczema, ischemic cerebral disease, chronic obstructive lung disease, cerebral edema, adult respiratory distress syndrome, neonatal pulmonary hypertension, Chrohn's disease, dermatitis (e.g., atopic dermatitis, etc.), rheumatism, gastric ulcer, peptic ulcer, gout or the like, using said thiazolylbenzofuran derivatives and pharmaceutically acceptable salts thereof.

Some thiazolylbenzofuran derivatives have been known as described, for example, in J. Heterocycl. Chem., 16, 97(1979), Chemical Abstract, 70, 11630b and 90, 152062t, and European Patent Application Publication No. 0 528 337.

The object thiazolylbenzofuran derivatives of this invention are new and can be represented by the following general formula (I):

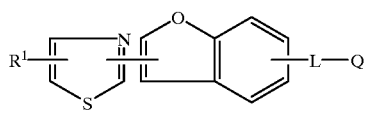

wherein $R^1$ is lower alkyl,
L is single bond or lower alkylene optionally substituted with aryl, oxo or hydroxy, and
Q is a heterocyclic group optionally substituted with one or more suitable substituent(s); or
lower alkoxy substituted with aryl which is substituted with one or more suitable substituent(s) and at least one of which is lower alkoxy optionally substituted with cyano, protected carboxy, carboxy, lower alkylene, a heterocyclic group optionally substituted with oxo, or amidino optionally substituted with hydroxy or lower alkoxy,
and its salt.

One preferable genus within the embodiment described in general formula (I) is the compound of the formula (II):

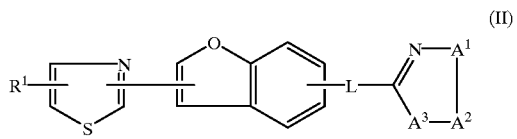

wherein —$A^1$—$A^2$—$A^3$— is (a) —$CR^2$=$CR^3$—X—, (b) —N=N—$NR^4$— or (c) —$NR^5$—N=N—,
X is S, O or $NR_6$, and
$R^2, R^3, R^4, R^5$ and $R^6$ are each independently hydrogen or suitable substituent,
in addition to their significances above, when $R^2$ and $R^3$ are taken together with the carbon atoms to which they are attached, they form an aromatic ring optionally substituted with one or more suitable substituent(s).

Within this genus is the preferable sub-genus of the compound of formula (II) wherein
$R^2$ and $R^3$ are each independently hydrogen or substituent selected from the group consisting of acyl; carboxy; protected carboxy; aryl; and lower alkyl optionally substituted with acyl, carboxy, protected carboxy, halogen, a heterocyclic group or cyano,
$R^4$ is hydrogen or lower alkyl optionally substituted with aryl which is optionally substituted with carboxy or protected carboxy, and
$R^5$ and $R^6$ are each same as $R^4$.

A preferable second genus within the embodiment described in general formula (I) is the compound of the formula (III)

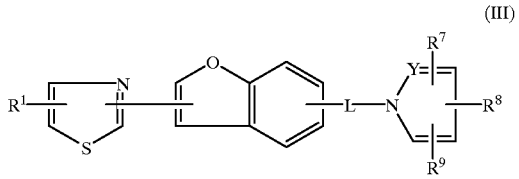

wherein Y is $CR^{10}$ or N, and
$R^7, R^8, R^9$ and $R^{10}$ are each independently hydrogen or suitable substituent,
in addition to their significances above, when $R^7$ and $R^8$ are taken together with the vicinal carbon atoms to which they are attached, they form an aromatic ring optionally substituted with one or more suitable substituent(s).

Within this genus is the preferable sub-genus of the compound of formula (III) wherein
$R^7$ and $R^8$ form a ring together with the vicinal carbon atoms to which they are attached, and $R^7$ and $R^8$ are represented by the structure:

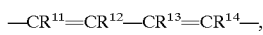

—$CR^{11}$=$CR^{12}$—$CR^{13}$=$CR^{14}$—, $R^9$ is hydrogen; cyano; acyl; carboxy; protected carboxy; a heterocyclic group; lower alkyl optionally substituted with acyl, carboxy or protected carboxy; or lower alkenyl optionally substituted with carboxy or protected carboxy,
$R^{10}$ is same as $R^9$, and
$R^{11}, R^{12}, R^{13}$ and $R^{14}$ are each independently hydrogen or substituent selected from the group consisting of acyl; carboxy; protected carboxy; halogen; nitro;

amino; hydroxy; lower cycloalkoxy; lower alkyl optionally substituted with halogen, hydroxy, acyl, carboxy or protected carboxy; and lower alkoxy optionally substituted with cyano, a heterocyclic group, acyl, carboxy, protected carboxy, lower alkylene, or aryl optionally substituted with halogen, acyl, carboxy or protected carboxy.

Within this sub-genus is the preferable class of the compound of the formula (III)
wherein Y is N
$R^9$ is a heterocyclic group, and
one of $R^{11}$ $R^{12}$, $R^{13}$ and $R^{14}$ is lower alkoxy and the others are each hydrogen.

A preferable third genus within the embodiment described in general formula (I) is the compound of the formula (I) wherein L is single bond, and
Q is lower alkoxy substituted with aryl, wherein aryl group is substituted with one or more of the same or different alkoxy group(s) optionally substituted with carboxy, protected carboxy, acyl, cyano, lower alkylene, a heterocyclic group optionally substituted with oxo, or amidino optionally substituted with hydroxy or lower alkoxy.

Within this genus is the preferable sub-genus of the compound of formula (I)
wherein Q is lower alkoxy substituted with aryl, wherein aryl group is substituted with lower alkoxy and lower alkoxy substituted with carboxy.

The object compound (I) or its salt can be prepared by processes as illustrated in the following schemes.

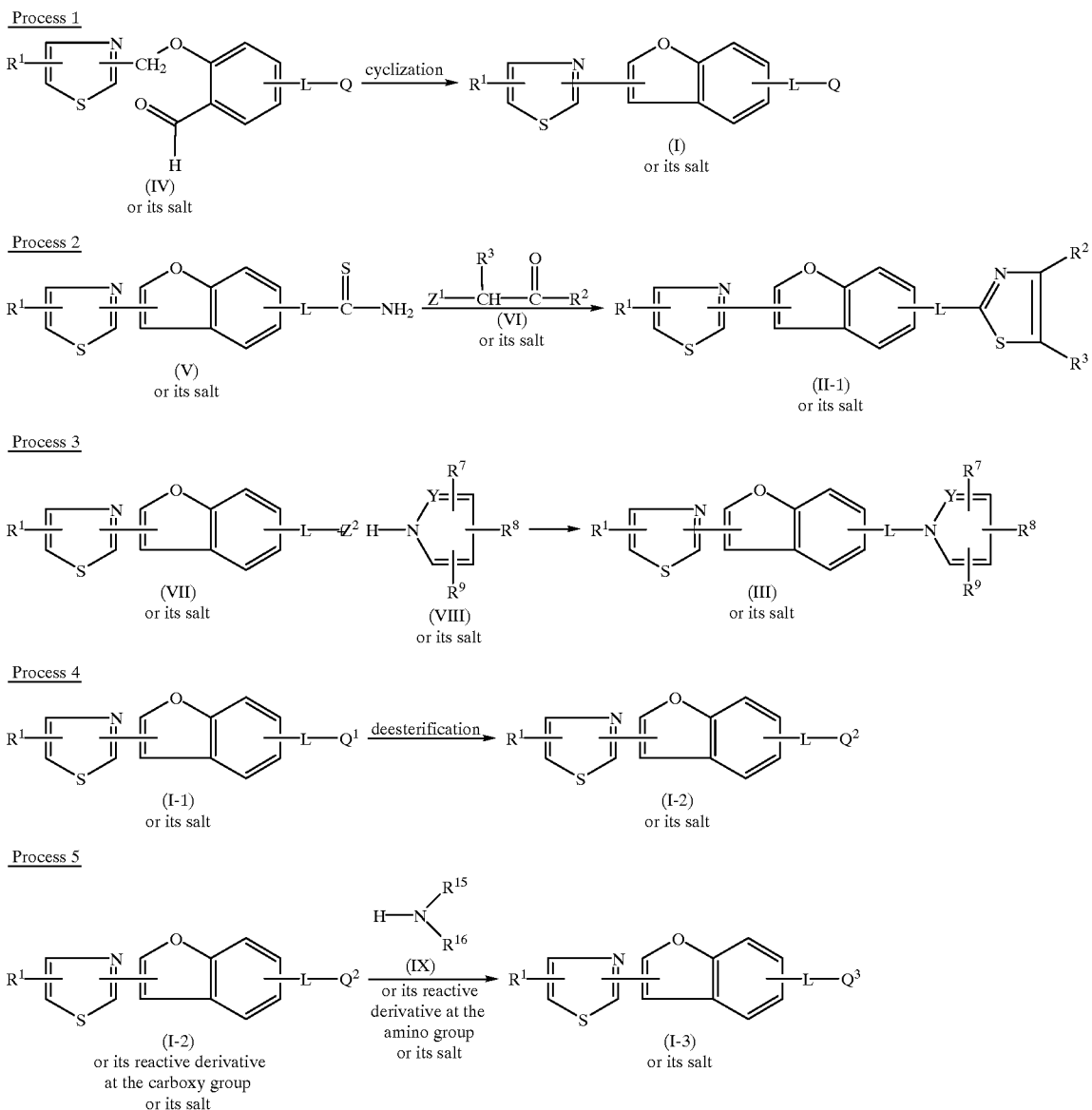

Process 6
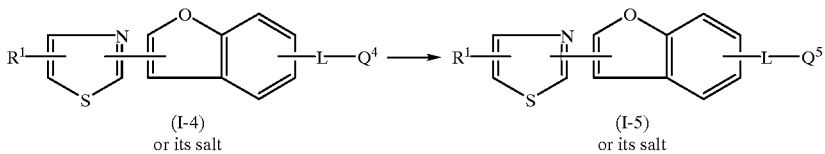
Process 7
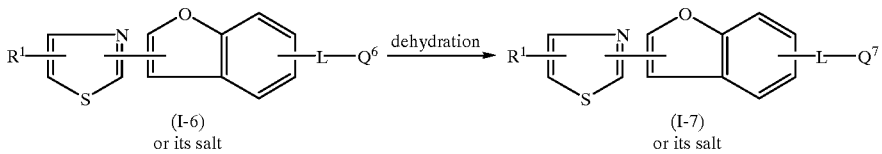
Process 8
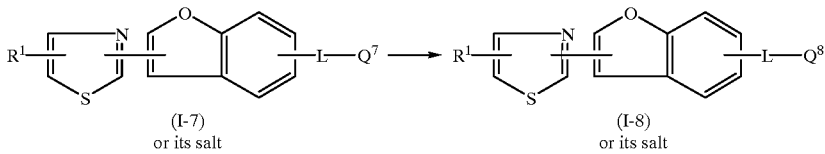
Process 9
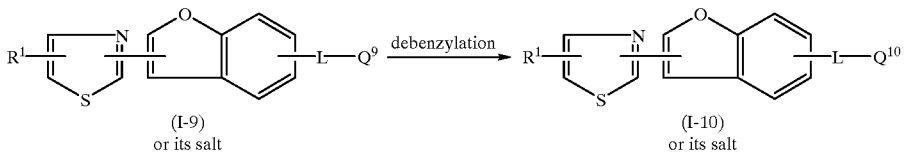
Process 10
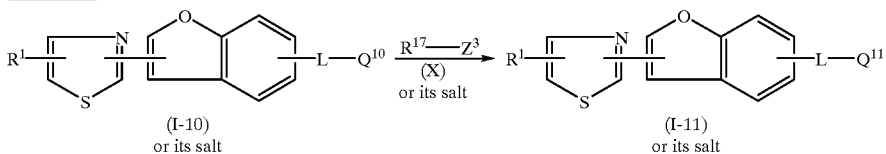
Process 11
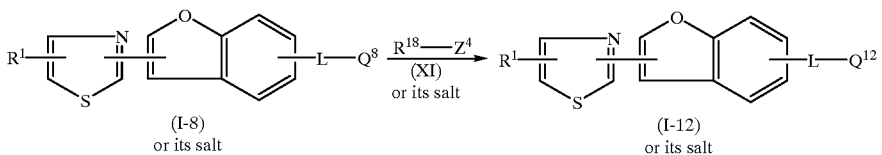
Process 12
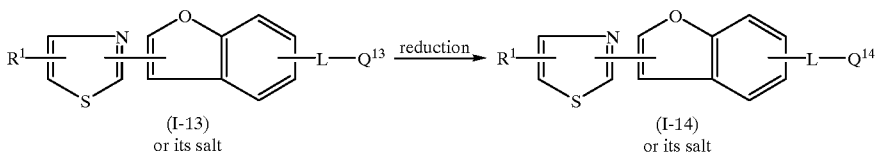
Process 13
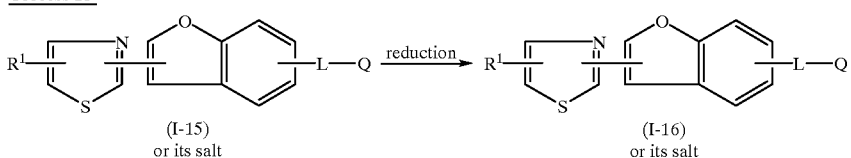
Process 14
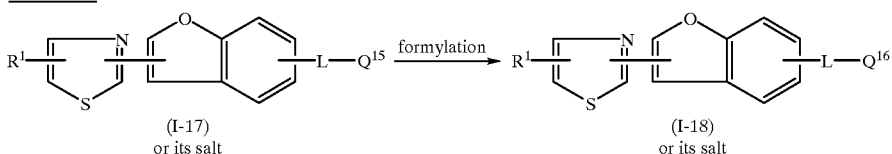

-continued
Process 15
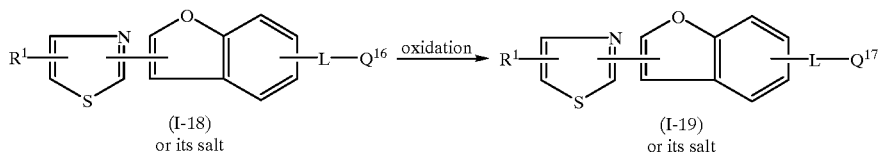
(I-18)
or its salt
(I-19)
or its salt
Process 16
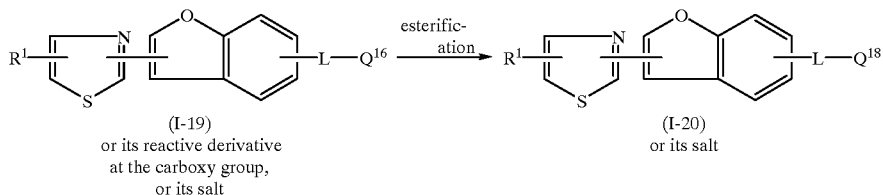
(I-19)
or its reactive derivative
at the carboxy group,
or its salt
(I-20)
or its salt
Process 17
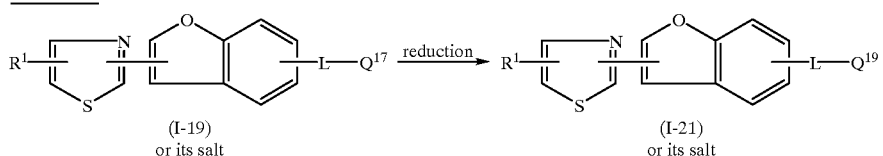
(I-19)
or its salt
(I-21)
or its salt
Process 18
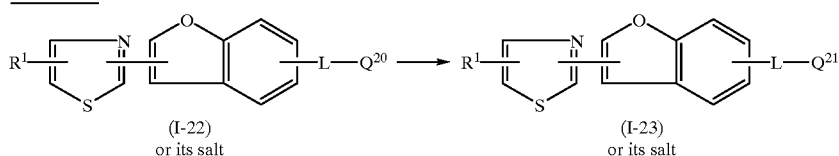
(I-22)
or its salt
(I-23)
or its salt
Process 19
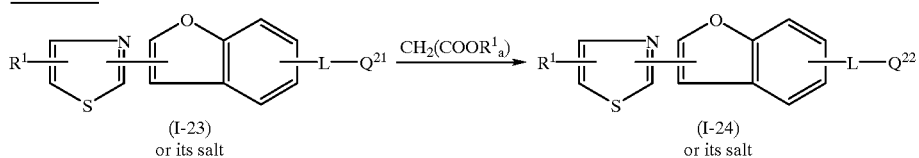
(I-23)
or its salt
(I-24)
or its salt
Process 20
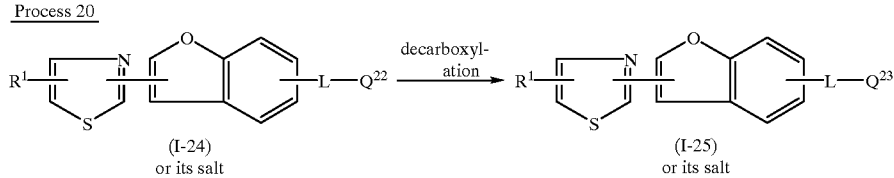
(I-24)
or its salt
(I-25)
or its salt
Process 21
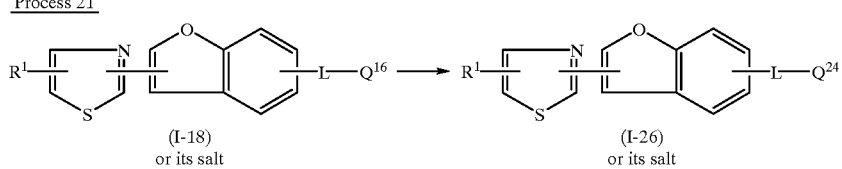
(I-18)
or its salt
(I-26)
or its salt
Process 22
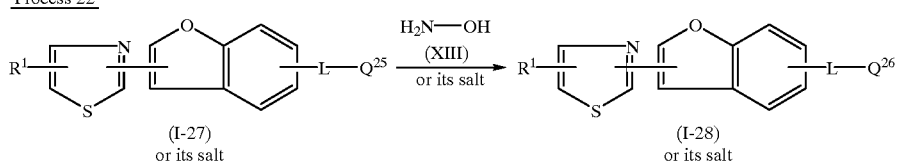
(I-27)
or its salt
(I-28)
or its salt
Process 23
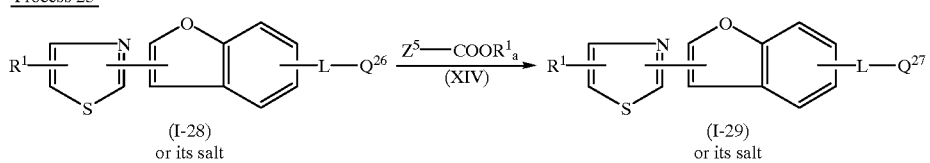
(I-28)
or its salt
(I-29)
or its salt Process 24

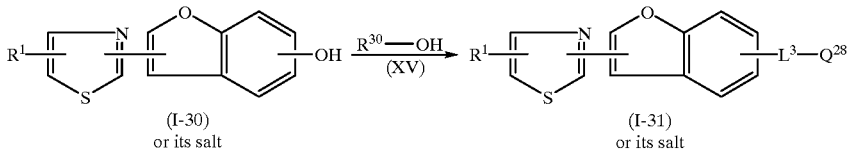

(I-30) or its salt (I-31) or its salt wherein
$R^1$ to $R^{14}$, L, Q, X and Y are each as defined above,
$R^5S$ is hydrogen or lower alkyl,
$R^{16}$ is hydrogen, lower alkyl, arylsulfonyl, amino or a heterocyclic group,
   in addition to their significances above, when $R^{15}$ and $R^{16}$ taken together with the nitrogen atom to which they are attached, they form a heterocyclic group containing one or more heteroatom(s),
$R^{17}$ is lower alkyl optionally substituted with carboxy, protected carboxy or aryl optionally substituted with halogen, carboxy or protected carboxy,
$R^{18}$ is lower alkyl optionally substituted with aryl substituted with carboxy or protected carboxy,
$R^{30}$ is lower alkyl substituted with aryl, wherein aryl group is substituted with one or more of the same or different alkoxy group(s) optionally substituted with carboxy, protected carboxy, acyl, cyano, lower alkylene, a heterocyclic group optionally substituted with oxo, or amidino optionally substituted with hydroxy or lower alkoxy,
$R_a^1$ is lower alkyl,
$Q^1$ is a heterocyclic group substituted with one or more suitable substituent(s), and at least one of which is
  (1) protected carboxy,
  (2) lower alkyl substituted with protected carboxy or aryl substituted with protected carboxy, or
  (3) lower alkoxy substituted with protected carboxy or aryl substituted with protected carboxy; or
  lower alkoxy substituted with aryl, wherein aryl group is substituted with one or more suitable substituent(s) and at least one of which is lower alkoxy substituted with protected carboxy,
$Q^2$ is a heterocyclic group substituted with one or more suitable substituent(s), and at least one of which is
  (1) carboxy,
  (2) lower alkyl substituted with carboxy or aryl substituted with carboxy, or
  (3) lower alkoxy substituted with carboxy or aryl substituted with carboxy; or
  lower alkoxy substituted with aryl, wherein aryl group is substituted with one or more suitable substituent(s) and at least one of which is lower alkoxy substituted with carboxy,
$Q^3$ is a heterocyclic group substituted with one or more suitable substituent(s), and at least one of which is
  (1) carbamoyl optionally substituted with one or more lower alkyl, arylsulfonyl, amino or a heterocyclic group,
  (2) carbamoyl substituted with two substituents which form, with nitrogen atom to which they are attached, a heterocyclic group containing one or more heteroatom(s),
  (3) lower alkyl substituted with carbamoyl or aryl substituted with carbamoyl, in both of which carbamoyl is the same as specified in the above (1) and (2), or
  (4) lower alkoxy substituted with carbamoyl or aryl substituted with carbamoyl, in both of which carbamoyl is the same as specified in the above (1) and (2); or
  lower alkoxy substituted with aryl, wherein aryl group is substituted with one or more suitable substituent(s) and at least one of which is lower alkoxy substituted with carbamoyl, in which carbamoyl is the same as specified in the above (1) and (2),
$Q^4$ is a heterocyclic group substituted with one or more suitable substituent(s), and at least one of which is lower alkyl substituted with halogen,
$Q^5$ is a heterocyclic group substituted with one or more suitable substituent(s), and at least one of which is lower alkyl substituted with cyano,
$Q^6$ is a heterocyclic group substituted with one or more suitable substituent(s), and at least one of which is
  (1) carbamoyl,
  (2) lower alkyl substituted with carbamoyl or aryl substituted with carbamoyl, or
  (3) lower alkoxy substituted with carbamoyl or aryl substituted with carbamoyl; or
  lower alkoxy substituted with aryl, wherein aryl group is substituted with one or more suitable substituent(s) and at least one of which is lower alkoxy substituted with carbamoyl,
$Q^7$ is a heterocyclic group substituted with one or more suitable substituent(s), and at least one of which is
  (1) cyano,
  (2) lower alkyl substituted with cyano or aryl substituted with cyano, or
  (3) lower alkoxy substituted with cyano or aryl substituted with cyano; or
  lower alkoxy substituted with aryl, wherein aryl group is substituted with one or more suitable substituent(s) and at least one of which is lower alkoxy substituted with cyano,
$Q^8$ is a heterocyclic group substituted with one or more suitable substituent(s), and at least one of which is
  (1) tetrazolyl,
  (2) lower alkyl substituted with tetrazolyl or aryl substituted with tetrazolyl, or
  (3) lower alkoxy substituted with tetrazolyl or aryl substituted with tetrazolyl; or
  lower alkoxy substituted with aryl, wherein aryl group is substituted with one or more suitable substituent(s) and at least one of which is lower alkoxy substituted with tetrazolyl,
$Q^9$ is a heterocyclic group substituted with one or more suitable substituent(s), and at least one of which is benzyloxy,
$Q^{10}$ is a heterocyclic group substituted with one or more suitable substituent(s), and at least one of which is hydroxy,
$Q^{11}$ is a heterocyclic group substituted with one or more suitable substituent(s), and at least one of which is lower alkoxy optionally substituted with carboxy, protected carboxy or aryl substituted with halogen, carboxy or protected carboxy, $Q^{12}$ is a heterocyclic group substituted with one or more suitable substituent(s), and at least one of which is
  (1) tetrazolyl substituted with lower alkyl substituted with aryl optionally substituted with carboxy or protected carboxy,
  (2) lower alkyl substituted with tetrazolyl substituted with lower alkyl substituted with aryl optionally substituted with carboxy or protected carboxy; or aryl substituted with tetrazolyl substituted with lower alkyl substituted with aryl optionally substituted with carboxy or protected carboxy, or
  (3) lower alkoxy substituted with tetrazolyl substituted with lower alkyl substituted with aryl optionally substituted with carboxy or protected carboxy; or aryl substituted with tetrazolyl substituted with lower alkyl substituted with aryl optionally substituted with carboxy or protected carboxy, $Q^{13}$ is a heterocyclic group substituted with one or more suitable substituent(s), and at least one of which is nitro, $Q^{14}$ is a heterocyclic group substituted with one or more suitable substituent(s), and at least one of which is amino, $Q^{15}$ is a heterocyclic group substituted with one or more suitable substituent(s), $Q^{16}$ is a heterocyclic group substituted with one or more suitable substituent(s), and at least one of which is formyl, $Q^{17}$ is a heterocyclic group substituted with one or more suitable substituent(s), and at least one of which is carboxy, $Q^{18}$ is a heterocyclic group substituted with one or more suitable substituent(s), and at least one of which is protected carboxy, $Q^{19}$ is a heterocyclic group substituted with one or more suitable substituent(s), and at least one of which is hydroxymethyl, $Q^{20}$ is a heterocyclic group substituted with one or more suitable substituent(s), and at least one of which is lower alkyl substituted with hydroxy, $Q^{21}$ is a heterocyclic group substituted with one or more suitable substituent(s), and at least one of which is lower alkyl substituted with halogen, $Q^{22}$ is a heterocyclic group substituted with one or more suitable substituent(s), and at least one of which is lower alkyl substituted with —CH(COOR$_a^1$)$_2$, $Q^{23}$ is a heterocyclic group substituted with one or more suitable substituent(s), and at least one of which is lower alkyl substituted with —CH$_2$COOR$_a^1$, $Q^{24}$ is a heterocyclic group substituted with one or more suitable substituent(s), and at least one of which is vinyl substituted with carboxy, $Q^{25}$ is lower alkoxy substituted with aryl, wherein aryl group is substituted with one or more suitable substituent(s), and at least one of which is lower alkoxy substituted with cyano, $Q^{26}$ is lower alkoxy substituted with aryl, wherein aryl group is substituted with one or more suitable substituent(s), and at least one of which is lower alkoxy substituted with amidino substituted with hydroxy, $Q^{27}$ is lower alkoxy substituted with aryl, wherein aryl group is substituted with one or more suitable substituent(s), and at least one of which is lower alkoxy substituted with, 1,2,4-oxadiazolin-5-on-3-yl, $Q^{28}$ is lower alkoxy substituted with aryl, wherein aryl group is substituted with one or more of the same or different alkoxy group(s) optionally substituted with carboxy, protected carboxy, acyl, cyano, lower alkylene, a heterocyclic group optionally substituted with oxo, or amidino optionally substituted with hydroxy or lower alkoxy, $L^1$ is lower alkylene substituted with oxo, $L^2$ is lower alkylene substituted with hydroxy, $L^3$ is single bond, and $Z^1$, $Z^2$, $Z^3$, $Z^4$ and $Z^5$ are each a leaving group.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

The term "suitable substituent" is intended to mean acyl; carboxy; protected carboxy; cyano; halogen; nitro; amino; acylamino; lower alkyl(acyl)amino; lower alkylsulfonylamino; hydroxy; lower alkylthio; lower alkylsulfinyl; lower alkylsulfonyl; sulfamoyl; aryl; a heterocyclic group; lower alkenyl optionally substituted with acyl, carboxy or protected carboxy; lower cycloalkoxy; lower alkyl optionally substituted with acyl, carboxy, protected carboxy, halogen, hydroxy, lower alkylene, cyano, a heterocyclic group or aryl optionally substituted with acyl, carboxy or protected carboxy; lower alkoxy optionally substituted with cyano, acyl, carboxy, protected carboxy, lower alkylene, a heterocyclic group optionally substituted with oxo, amidino optionally substituted with hydroxy or lower alkoxy, or aryl optionally substituted with halogen, acyl, carboxy or protected carboxy; or the like.

Suitable "lower alkyl" and lower alkyl moiety in the terms "lower alkyl(acyl)amino", "lower alkylthio", "lower alkylsulfinyl" and "lower alkylsulfonyl" may be a straight or branched $C_1$–$C_6$ alkyl such as methyl, ethyl, propyl, isopropyl, butyl, isobutyl, tert-butyl, pentyl, hexyl or the like, in which preferable one is $C_1$–$C_4$ lower alkyl such as methyl, ethyl, propyl, butyl, isobutyl or tert-butyl.

Suitable "lower alkylene" may be a straight or branched $C_1$–$C_6$ alkylene such as methylene, ethylene, trimethylene, propylene, tetramethylene, pentamethylene, hexamethylene, ethylethylene, ethylidene, propylidene, or the like.

Suitable "lower alkenyl" may be a straight or branched $C_2$–$C_6$ alkenyl such as vinyl, ethenyl, propenyl, butenyl, isobutenyl, or the like.

Suitable "aryl" and aryl moiety in the terms "arylsulfonyl", may be phenyl, naphthyl, tolyl, xylyl, mesityl, cumenyl, di(tert-butyl)phenyl, or the like, in which preferable one is phenyl or tolyl.

Suitable "halogen" may be fluoro, chloro, bromo or iodo, in which preferable one is fluoro, chloro or bromo.

Suitable "lower alkoxy" may be a straight or branched $C_1$–$C_6$ alkoxy such as methoxy, ethoxy, propoxy, isopropoxy, isobutyloxy, butoxy, pentyloxy, or the like, in which preferable one is methoxy.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group, such as
  (1) unsaturated 3 to 7-membered, preferably 5- or 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2, 3-triazolyl, 2H-1,2,3-triazolyl, etc.], tetrazolyl [e.g., 1H-tetrazolyl, 2H-tetrazolyl, etc.], etc.;

(2) saturated 3 to 7-membered, preferably 5- or 6-membered heteromonocyclic group containing 1 to 4 nitrogen atoms [e.g., pyrrolidinyl, imidazolidinyl, piperidyl, piperazinyl, etc.];

(3) unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]-pyridazinyl, etc.], etc.;

(4) unsaturated 3 to 7-membered, preferably 5- or 6-membered heteromonocyclic group containing an oxygen atom, for example, pyranyl, furyl, etc.;

(5) unsaturated, 3 to 7-membered, preferably 5- or 6-membered heteromonocyclic group containing 1 to 2 sulfur atoms, for example, thienyl, etc.;

(6) unsaturated 3 to 7-membered, preferably 5- or 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,2,4-oxadiazolinyl, 1,3,4-oxadiazolyl, 1,2,5-oxadiazolyl, etc.], etc.;

(7) saturated 3 to 7-membered, preferably 5- or 6-membered heteromonocyclic group containing 1 to 2 oxygen atoms and 1 to 3 nitrogen atoms [e.g., morpholinyl, etc.];

(8) unsaturated condensed heterocyclic group containing 1 to 2 oxygen atoms and 1 to 3 nitrogen atoms [e.g., benzoxazolyl, benzoxadiazolyl, etc.];

(9) unsaturated 3 to 7-membered, preferably 5- or 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

(10) saturated 3 to 7-membered, preferably 5- or 6-membered heteromonocyclic group containing 1 to 2 sulfur atoms and 1 to 3 nitrogen atoms [e.g., thiomorpholinyl, thiazolidinyl, etc.];

(11) unsaturated condensed heterocyclic group containing 1 to 2 sulfur atoms and 1 to 3 nitrogen atoms [e.g., benzothiazolyl, benzothiadiazolyl, etc.]; or the like.

"Heterocyclic group" defined above may be substituted with suitable substituent(s) such as lower alkyl, cyclo(lower)alkyl, or the like, for example 4-methylpiperadino, 4-cyclohexylpiperadino, etc.

Among the above, more preferable heterocyclic group included in Q and $Q^1$ to $Q^{28}$ is above-mentioned (1), (3) or (9), in which the most preferable one is tetrazolyl, indolyl, indazolyl or thiazolyl; more preferable heterocyclic group included in $R^2$, $R^3$ and $R^9$ to $R^{14}$ is above-mentioned (1), in which the most preferable one is tetrazolyl; more preferable heterocyclic group formed by $R^{15}$ and $R^{16}$, and nitrogen atom to which they are attached, is above-mentioned (2), (7) or (10), in which the most preferable one is pyrrolidinyl, piperidyl, piperazinyl, morpholinyl or thiomorpholinyl; and more preferable heterocyclic group included in $R^{30}$ is above-mentioned (1) or (6), in which the most preferable one is tetrazolyl or oxadiazolyl.

Suitable "acyl" and acyl moiety in the terms "acylamino" and "lower alkyl(acyl)amino" may be aliphatic acyl, aromatic acyl or aliphatic acyl optionally substituted aryl, which are derived from carboxylic acid or carbamic acid.

The aliphatic acyl may include lower alkanoyl optionally substituted with one or more suitable substituent(s) such as carboxy or protected carboxy (e.g., formyl, acetyl, propionyl, butyryl, hexanoyl, oxalo, carboxyacetyl, protected oxalo (e.g., benzyloxyoxalyl, etc.), and so on); carbamoyl optionally substituted with one or more suitable substituent(s) such as lower alkyl, arylsulfonyl, or a heterocyclic group (e.g., N-methylcarbamoyl, N,N-dimethylcarbamoyl, N-ethylcarbamoyl, N,N-diethylcarbamoyl, N-propylcarbamoyl, N-tolenesulfonylcarbamoyl, N-(4-methylpiperazin-1-yl) carbamoyl, and so on); or carbamoyl substituted with two substituents on the nitrogen atom forming a 5- to 7-membered heterocyclic group, which contains one or more heteroatoms and is optionally substituted with lower alkyl or cyclo(lower)alkyl (e.g., 1-pyrolidinylcarbonyl, 1-piperidylcarbonyl, piperazinocarbonyl, 4-methylpiperazin-1-ylcarbonyl, 4-cyclohexylpiperazin-1-ylcarbonyl, morpholinocarbonyl, 1-thiomorpholinylcarbonyl, and so on); or the like.

The aromatic acyl may include aroyl optionally substituted with one or more suitable substituent(s) such as nitro (e.g., benzoyl, naphthoyl, nitrobenzoyl, and so on), or the like.

The aliphatic acyl substituted with aryl may include ar(lower)alkanoyl which may have one or more suitable substituent(s) such as lower alkoxy (e.g., phenylacetyl, 4-methoxyphenylacetyl, and so on) or the like.

Suitable "protected carboxy" may be a pharmaceutically acceptable and a common protected carboxy, such as an esterified carboxy, or the like, and concrete examples of the ester moiety in said esterified carboxy may be lower alkyl (e.g., methyl, ethyl, propyl, tert-butyl, and so on) optionally substituted with substituted or unsubstituted aryl (e.g., benzyl, 4-methoxybenzyl, 2,4,6-trichlorobenzyl, and so on) or the like.

Suitable "cyclo(lower)alkyl" and cyclo(lower)alkyl moiety in the term "lower cycloalkoxy" may be $C_3$-$C_6$ cycloalkyl such as cyclopropyl, cyclopentyl, cyclohexyl, or the like.

Suitable "leaving group" may be halogen [e.g., fluoro, chloro, bromo, iodo], arylsulfonyloxy [e.g., benzenesulfonyloxy, tosyloxy, etc.], alkylsulfonyloxy [e.g., mesyloxy, ethanesulfonyloxy, etc.], oxyphosphonium salt [e.g., —O—PPh$_3$, etc.], or the like, in which preferable one is halogen.

Suitable pharmaceutically acceptable salts of the object compound (I) are conventional ones and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylenediamine salt, etc.), an organic acid salt (e.g., acetate, trifluoroacetate, maleate, tartrate, fumalate, methanesulfonate, benzenesulfonate, formate, toluenesulfonate, etc.), an inorganic acid salt (e.g., hydrochloride, hydrobromide, hydriodide, sulfate, phosphate, etc.), a salt with an amino acid (e.g., arginine, aspartic acid, glutamic acid, etc.), or the like.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixture and separate individual isomers.

The compounds of formula (I) may also exist in tautomeric forms and the invention includes both mixtures and separate individual tautomers.

The compound of the formula (I) and its salt can be in the form of a solvate, which is included within the scope of the present invention. The solvate preferably include a hydrate and an ethanolate.

Also included in the scope of invention are radiolabelled derivatives of compounds of formula (I) which are suitable for biological studies.

The processes for preparing the object compound (I) are explained in detail in the following.

Process 1

The object compound (I) or its salt can be prepared by subjecting a compound (IV) or its salt to cyclization reaction.

This reaction is preferably carried out in the presence of a dehydrating agent [e.g., acetic anhydride, etc.] or a base such as alkali metal [e.g., lithium, sodium, potassium, etc.], alkaline earth metal [e.g., calcium, magnesium, etc.], alkali metal hydride [e.g., sodium hydride, etc.], alkaline earth metal hydride [e.g., calcium hydride, etc.], alkali metal alkoxide [e.g., sodium methoxide, sodium ethoxide, potassium tert-butoxide, etc.], alkaline earth metal alkoxide [e.g., magnesium methoxide, magnesium ethoxide, etc.], trialkylamine [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

The reaction is usually carried out in a conventional solvent such as dioxane, tetrahydrofuran, pyridine, aromatic hydrocarbon [e.g., benzene, toluene, xylene, etc.] or any other organic solvent which does not adversely influence the reaction.

The reaction temperature is not critical, and the reaction is usually carried out under cooling to heating.

Process 2

The object compound (II-1) or its salt can be prepared by reacting a compound (V) or its salt with a compound (VI) or its salt.

The reaction is usually carried out in a conventional solvent such as an alcohol [e.g., methanol, ethanol, propanol, isopropanol, etc.], aromatic hydrocarbon [e.g., benzene, toluene, xylene, etc.], ethyl acetate, acetonitrile, dioxane, chloroform, methylene chloride, N,N-dimethylformamide or any other organic solvent which does not adversely influence the reaction.

The reaction temperature is not critical, and the reaction is usually carried out under cooling to heating.

Process 3

The compound (III) or its salt can be prepared by reacting the compound (VII) or its salt with the compound (VIII) or its salt.

This reaction is usually carried out in the presence of an inorganic or an organic base.

Suitable inorganic base may include an alkali metal [e.g., sodium, potassium, etc.], an alkali metal hydroxide [e.g., sodium hydroxide, potassium hydroxide, etc.], alkali metal hydrogen carbonate [e.g., sodium hydrogen carbonate, potassium hydrogen carbonate, etc.], alkali metal carbonate [e.g., sodium carbonate, etc.], alkali earth metal carbonate [calcium carbonate, etc.], alkali metal hydride [e.g., sodium hydride, etc.], or the like.

Suitable organic base may include tri(lower)alkylamine [e.g., triethylamine, N,N-diisopropylethylamine, etc.], alkyl magnesium bromide [e.g., methyl magnesium bromide, ethyl magnesium bromide, etc.], alkyl lithium [e.g., methyl lithium, butyl lithium, etc.], lithium diisopropylamide, lithium hexamethyldisirazido, or the like.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

Process 4

The object compound (I-2) or its salt can be prepared by subjecting a compound (I-1) or its salt to deesterification reaction.

The reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g., lithium, sodium, potassium, etc.], an alkaline earth metal [e.g., magnesium, calcium, etc.], the hydroxide or carbonate or bicarbonate thereof, tri(lower)alkylamine [e.g., trimethylamine, triethylamine, diethylisopropylamine, etc.], picoline, 1,5-diazabicyclo[4.3.0]non-5-ene, 1,4-diazabicyclo[2.2.23octane, 1,8-diazabicyclo[5.4.0]undec-7-ene, or the like.

Suitable acid may include an organic acid [e.g., formic acid, acetic acid, propionic acid, trichloroacetic acid, trifluoroacetic acid, etc.], an inorganic acid [e.g., hydrochloric acid, hydrobromic acid, hydroiodic acid, sulfuric acid, etc.] and Lewis acid [e.g., boron tribromide, etc.].

The reaction is usually carried out in a solvent such as water, an alcohol [e.g., methanol, ethanol, etc.], xylene, diethylene glycol monomethyl ether, methylene chloride, tetrahydrofuran, a mixture thereof or any other solvent which does not adversely influence the reaction. A liquid base or acid can be also used as the solvent.

The reaction temperature is not critical and the reaction is usually carried out under cooling to warming.

The reduction can be applied preferably for elimination of the ester moiety such as 4-nitrobenzyl, 2-iodoethyl, 2,2,2-trichloroethyl, or the like. The reduction method applicable for the elimination reaction may include chemical reduction and catalytic reduction.

Suitable reducing agents to be used in chemical reduction are a combination of metal [e.g., tin, zinc, iron, etc.] or metallic compound [e.g., chromium chloride, chromium acetate, etc.] and an organic or inorganic acid [e.g., formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalyst [e.g., platinum plate, spongy platinum, platinum black, platinum oxide, etc.], palladium catalyst [e.g., spongy palladium, palladium black, palladium oxide, palladium on carbon, colloidal palladium, palladium hydroxide on carbon, palladium on barium sulfate, palladium on barium carbonate, etc.], nickel catalyst -(e.g., reduced nickel, nickel oxide, Raney nickel, etc.], cobalt catalyst [e.g., reduced cobalt, Raney cobalt, etc.], iron catalyst [e.g., reduced iron, Raney iron, etc.], copper catalyst [e.g., reduced copper, Raney copper, Ullman copper, etc.] or the like. The catalytic reduction may be carried out in the presence of hydrogen or hydrogen doner such as formic acid, ammonium formate, cyclohexen, or the like.

The reduction is usually carried out in a conventional solvent which does not adversely influence the reaction such as water, an alcohol [e.g., methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 5

The compound (I-3) or its salt can be prepared by reacting the compound (I-2) or its reactive derivative at the carboxy group, or its salt, with the compound (IX) or its reactive derivative at the amino group, or its salt.

Suitable reactive derivative at the amino group of the compound (IX) may include Schiff's base type imino or its tautomeric enamine type isomer formed by the reaction of the compound (IX) with a carbonyl compound such as aldehyde, ketone or the like; a silyl derivative formed by the reaction of the compound (IX) with a silylating reagent such as N,O-bis(trimethylsilyl)acetamide, N-trimethylsilylacetamide, or the like.

Suitable reactive derivative of the compound (I-2) may include an acid chloride, an acid anhydride, an activated amide, an activated ester, or the like.

Suitable acid anhydride may be a symmetric anhydride or a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfuric acid, thiosulfuric acid, alkanesulfonic acid (e.g., methanesulfonic acid, ethanesulfonic acid, etc.), alkylcarbonic acid, aliphatic carboxylic acid (e.g., pivalic acid, pentanoic acid, isopentanoic acid, etc.); aromatic carboxylic acid (e.g., benzoic acid, chlorobenzoic acid, fluorobenzoic acid, nitrobenzoic acid, etc.), or the like.

Suitable activated amide may be imidazolylamide, 4-substituted imidazolylamide, dimethylpyrazolylamide, triazolylamide, tetrazolylamide, or the like.

Suitable activated ester may be dimethyliminomethyl [(CH$_3$)$_2$N+e,sez +hu ++ee =CH—] ester, vinyl ester, propargyl ester, 4-nitrophenyl ester, 2,4-dinitrophenyl ester, trichlorophenyl ester, pentachlorophenyl ester, pentafluorophenyl ester, methanesulfonylphenyl ester, phenyl thioester, p-nitrophenyl thioester, carboxymethyl thioester, pyranyl ester, pyridyl ester, 8-quinolyl thioester, an activated ester with a N-hydroxy compound (e.g., N,N-dimethylhydroxylamine, 1-hydroxy-2H-pyridone, N-hydroxysuccinimido, N-hydroxybenzotriazole, N-hydroxyphthalimide, etc.), or the like.

These reactive derivatives can optionally be selected from them according to the kind of compound (I-2) to be used.

When the compound (I-2) is used in free acid form or its salt form in the reaction, the reaction is preferably carried out in the presence of condensing agent.

Suitable condensing agent may include a carbodiimide (e.g., N,N'-dicyclohexylcarbodiimido, N-cyclohexyl-N'-(4-diethylaminocyclohexyl)carbodiimido, N-ethyl-N'-(3-dimethylaminopropyl)carbodiimido or its hydrochloride) diphenylphosphinic azido, diphenylphosphinic chloride, diethylphosphoryl cyanide, bis(2-oxo-3-oxazolidinyl) phosphinic chloride, N,N'-carbonyldiimidazole, 2-ethoxy-1-ethoxycarbonyl-1,2-dihydroquinoline, cyanuric chloride, or the like.

The reaction may be also carried out in the presence of organic or inorganic base such as alkali metal carbonate, tri(lower)alkylamine, pyridine, N-(lower)alkylmorphorine, or the like.

The reaction is usually carried out in a conventional solvent such as water, acetone, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

Process 6

The object compound (I-5) can be prepared by reacting a compound (I-4) with a cyanide compound.

Suitable cyanide compound may be a metallic cyanide such as alkali metal cyanide [e.g., sodium cyanide, potassium cyanide, etc.], cuprous cyanide, or the like.

This reaction is preferably carried out in the presence of alkali metal iodide [e.g., sodium iodide, potassium iodide, etc.], phase transfer catalyst [e.g., Adogen 464 (Trademark : Aldrich), etc.], or the like.

The reaction is usually carried out in a conventional solvent such as water, an alcohol [e.g., methanol, ethanol, etc.], pyridine, quinoline, N,N-dimethylformamide, a mixture thereof or any other solvent which does not adversely influence the reaction.

The reaction temperature is not critical, and the reaction is usually carried out under warming to heating.

Process 7

The compound (I-7) or its salt can be prepared by subjecting the compound (I-6) or its salt to dehydration reaction at the carbamoyl group.

Dehydration is carried out in the conventional manner, which is capable dehydrating a carbamoyl group to cyano group, and suitable dehydrating agent may be phosphorus compound (e.g., phosphorous pentoxide, phosphorus pentachloride, phosphorous oxychloride, pyrocatechyl phosphorus trichloride, and so on); thionyl chloride; or a combination of triaryl phosphine (e.g., triphenyl phosphine, and so on) and chloroform or carbon tetrachloride.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

Process 8

The object compound (I-8) or its salt can be prepared by reacting a compound (I-7) or its salt with an azide compound.

Suitable azide compound may be alkali metal azide [e.g., sodium azide, potassium azide, etc.], alkaline earth metal azide [e.g., calcium azide, etc.], aluminum azide, hydrogen azide, trimethyltin azide, or the like.

The reaction is preferably carried out in the presence of ammonium halide [e.g., ammonium chloride, ammonium bromide, etc.], lower alkylammonium halide [e.g., trimethylammonium chloride, triethylammonium chloride, etc.] or the like.

The reaction is usually carried out in a conventional solvent such as tetrahydrofuran, dioxane, N,N-dimethylformamide or any other organic solvent which does not adversely influence the reaction.

The reaction temperature is not critical, and the reaction can be carried out under warming to heating.

Process 9

The compound (I-10) or its salt can be prepared by subjecting the compound (I-9) or its salt to removal of benzyl group.

The removal of benzyl group is carried out by using conventional manner, which is capable removing of benzyl group of benzyloxy group to hydroxy group, and suitable agent is ones such as boron tribromide; a combination of trifluoroacetic acid and sulfur compound (e.g., thioanisole, 1,2-ethanedithiol, and so on); a combination of Lewis acid (e.g., boron trifluoride, and so on) and Lewis base (e.g., ethanethiol and so on); trimethylsilyl iodide; and so on.

The removal of benzyl group is also carried out by catalytic reduction using catalyst, and hydrogen or hydrogen doner.

Suitable catalyst to be used in catalytic reduction are conventional ones such as platinum catalyst (e.g., platinum black, platinum on carbon, platinum oxide, and so on), palladium catalyst (e.g., palladium black, palladium on carbon, palladium oxide, and so on) and so on.

Suitable hydrogen donor may be cyclohexene, cyclohexadiene, ammonium formate, hydrazine, and so on.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide, or any other organic solvents which do not adversely affect the reaction, or the mixture thereof.

The reaction temperature is not critical and the reaction is usually carried out under cooling to warming.

Process 10

The compound (I--11) or its salt can be prepared by reacting the compound (I-10) or its salt with the compound (X) or its salt.

This reaction can be carried out in a substantially similar manner to that of the Process 3, and therefore the reagents to be used and the reaction conditions (e.g., solvent, reaction temperature, etc.) can be referred to those of the Process 3.

Process 11

The object compound (I-12) or its salt can be prepared by reacting a compound (I-8) or its salt with a compound (XI) or its salt.

The reaction is preferably carried out in the presence of a base such as an alkali metal [e.g., sodium, potassium, etc.], an alkaline earth metal [e.g., magnesium, calcium, etc.], the hydride or hydroxide or carbonate or bicarbonate thereof.

The reaction is usually carried out in a conventional solvent which does not adversely influence the reaction such as water, dioxane, an alcohol [e.g., methanol, ethanol, etc.], acetonitrile, tetrahydrofuran, N,N-dimethylformamide, acetone, 2-butanone, or a mixture thereof. Additionally, in case that the compound (XI) is in liquid, it can also be used as a solvent.

The reaction temperature is not critical and the reaction can be carried out under cooling to heating.

In this reaction, the compound(s) (I-12) substituted with $R^{18}$ on 1 or/and 2 position(s) may be obtained according to reaction conditions. This case is included within the scope of the present reaction.

Process 12

The compound (I-14) or its salt can be prepared by subjecting a compound (I-13) or its salt to reduction.

The present reduction is carried out by chemical reduction, catalytic reduction, or the like.

Suitable reducing agents to be used in chemical reduction are a combination of metal [e.g., tin, zinc, iron, etc.] or metallic compound [e.g., chromium chloride, chromium acetate, etc.] and an organic or inorganic acid [e.g., formic acid, acetic acid, propionic acid, trifluoroacetic acid, p-toluenesulfonic acid, hydrochloric acid, hydrobromic acid, etc.], or the like.

Suitable catalysts to be used in catalytic reduction are conventional ones such as platinum catalyst [e.g., platinum, platinum black, platinum oxide, etc.], palladium catalyst [e.g., palladium black, palladium oxide, palladium on carbon, etc.], nickel catalyst [e.g., reduced nickel, nickel oxide, Raney nickel, etc.], cobalt catalyst [e.g., reduced cobalt, Raney cobalt, etc.], iron catalyst [e.g., reduced iron, Raney iron, etc.], copper catalyst [e.g., reduced copper, Raney copper, Ullman copper, etc.] or the like.

The reduction is usually carried out in a conventional solvent which does not adversely influence the reaction such as water, an alcohol [e.g., methanol, ethanol, propanol, etc.], N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent and other conventional solvent such as diethyl ether, methylene chloride, dioxane, tetrahydrofuran, etc., or a mixture thereof.

The reaction temperature of this reduction is not critical and the reaction is usually carried out under cooling to warming.

Process 13

The object compound (I-16) or its salt can be prepared by reacting a compound (I-15) or its salt with a reducing agent.

Suitable reducing agent may be aluminum hydride compound [e.g., lithium aluminum hydride, lithium tri-t-butoxyaluminum hydride, etc.], borohydride compound [e.g., sodium borohydride, etc.], aluminum alkoxide [e.g., aluminum isopropoxide, etc.], or the like.

The reaction is usually carried out in a conventional solvent, such as water, an alcohol [e.g., methanol, ethanol, propanol, isopropanol, etc.], chloroform, diethyl ether, dioxane, or any other organic solvent which does not adversely influence the reaction, or a mixture thereof.

The reaction temperature is not critical, and the reaction is usually carried out under cooling to heating.

Process 14

The compound (I-18) or its salt can be prepared by reacting a compound (I-17) or its salt with a formylating agent.

Suitable formylating agent may be N,N-dimethylformamide; $(CH_3)_2N^+$=$CHCl.Cl_2PO_2$— (so-called Vilsmeier reagent prepared by the reaction of N,N-dimethylformamide with phosphorus oxychloride, phosgene, etc.); or the like.

When a formylating agent is N,N-dimethylformamide, the reaction is preferably carried out in the presence of a base such as lower alkyl metal [e.g., n-butyl lithium, ethyl magnesium bromide, etc.], or the like.

The reaction is usually carried out in a solvent such as dioxane, tetrahydrofuran, N,N-dimethylformamide, methylene chloride, chloroform, or any other organic solvent which does not adversely influence the reaction, or a mixture thereof.

The reaction temperature is not critical, and the reaction is usually carried out under cooling to heating.

Process 15

The compound (I-19) or its salt can be prepared by subjecting the compound (I-18) or its salt to oxidation reaction.

Oxidation is carried out in a conventional manner, which is capable of oxidizing formyl group to carboxy group, and suitable oxidizing reagent may be oxygen acid such as periodate (e.g., sodium periodate, potassium periodate, etc.), peroxy acid such as peroxybenzoic acid (e.g., peroxybenzoic acid, m-chloroperoxybenzoic acid, etc.), potassium permanganate, cromic acid, sodium hyprochlorite, or the like.

The reaction is usually carried out in a conventional solvent such as water, alcohol (e.g., methanol, ethanol, isopropyl alcohol, etc.), tetrahydrofuran, dioxane, dichloromethane, ethylene dichloride, chloroform, N,N-dimethylformamide, N,N-dimethylacetamide, or any other organic solvent which does not adversely affect the reaction, or a mixture thereof.

Among these solvents, hydrophilic solvents may be used in a mixture with water.

The reaction temperature is not critical and the reaction is usually carried out under cooling to heating.

Process 16

The compound (I-20) or its salt can be prepared by reacting a compound (I-19) or its reactive derivative at the carboxy group, or its salt, with a hydroxy compound.

Suitable reactive derivative at the carboxy group of the compound (I-19) may be acid halide [e.g., acid chloride, acid bromide, etc.], or the like.

Suitable hydroxy compound may be an alcohol [e.g., methanol, ethanol, propanol, benzyl alcohol, etc.], phenol, naphthol, or the like.

The reaction is usually carried out in a conventional solvent such as diethyl ether, tetrahydrofuran, dioxane or any other organic solvent which does not adversely influence the reaction, or a mixture thereof.

Additionally, in case that the above-mentioned hydroxy compound is in liquid, it can also be used as a solvent.

The reaction temperature is not critical and the reaction is usually carried out under cooling to heating.

When the compound (I-19) is used in a free acid form in the reaction, the reaction is preferably carried out in the presence of an inorganic acid, or condensing agent.

Suitable inorganic acid may be the one exemplified in the above-mentioned Process 4 and suitable condensing agent may be the one exemplified in the above-mentioned Process 5.

Process 17

The compound (I-21) or its salt can be prepared by reacting a compound (I-19) or its salt with a reducing agent.

Suitable reducing agent may be aluminum hydride compound [e.g., lithium aluminum hydride, lithium tri-t-butoxyaluminum hydride, etc.], borohydride compound [e.g., borane-dimethylsulfide complex, sodium borohydride, etc.], aluminum alkoxide [e.g., aluminum isopropoxide, etc.] and the like.

The reaction is usually carried out in a conventional solvent, such as water, an alcohol [e.g., methanol, ethanol, propanol, isopropanol, etc.], chloroform, diethyl ether, dioxane, or any other organic solvent which does not adversely influence the reaction, or a mixture thereof.

The reaction temperature is not critical, and the reaction can be carried out under cooling to heating.

Process 18

The compound (I-23) or its salt can be prepared by subjecting the compound (I-22) or its salt to halogenation.

This halogenation is usually carried out by using a conventional halogenating agent such as halogen (e.g., chlorine, bromine, etc.), phosphorus trihalide (e.g., phosphorus tribromide, phosphorus trichloride, etc.), phosphorus pentahalide (e.g., phosphorus pentachloride, phosphorus pentabromide, etc.), phosphorus oxychloride (e.g., phosphoryl trichloride, phosphoryl monochloride, etc.), thionyl halide (e.g., thionyl chloride, thionyl bromide, etc.), oxalyl halide (e.g., oxalyl chloride, oxalyl bromide, etc.), sulfuryl halide (e.g., sulfuryl chloride, etc.), pyridinium hydrobromide perbromide, or the like.

This reaction is usually carried out in a solvent such as water, alcohol (e.g., methanol, ethanol, isopropyl alcohol, etc.), benzene, dioxane, N,N-dimethylformamide, tetrahydrofuran, methylene chloride, ethylene dichloride, chloroform, diethyl ether, or any other solvent which does not adversely affect the reaction, or a mixture thereof.

The reaction temperature is not critical and the reaction is usually carried out under cooling to warming.

Process 19

The compound (I-24) or its salt can be prepared by reacting the compound (I-23) or its salt with malonic acid derivative (XII).

This reaction usually carried out in the presence of an inorganic or organic base exemplified in Process 3.

The reaction is usually carried out in a conventional solvent such as water, alcohol [e.g., methanol, ethanol, isopropyl alcohol, etc.], tetrahydrofuran, dioxane, toluene, N,N-dimethylformamide or any other organic solvent which does not adversely affect the reaction, or a mixture thereof.

The reaction temperature is not critical and the reaction is usually carried out under cooling to warming.

Process 20

The compound (I-25) or its salt can be prepared by subjecting the compound (I-24) or its salt to decarboxylation.

This reaction consists of a deesterification and an acid catalyzed decarboxylation. The deesterification can preferably be carried out in the presence of the inorganic base exemplified in Process 3 and the acid used in the acid catalyzed decarboxylation may be the inorganic or organic acid such as hydrochloric acid, sulfuric acid, phosphoric acid, acetic acid, or the like.

The reaction is usually carried out in a conventional solvent such as water, alcohol [e.g., methanol, ethanol, isopropyl alcohol, etc.], tetrahydrofuran, dioxane, toluene, xylene, methylene chloride, chloroform, N,N-dimethylformamide or any other organic solvent which does not adversely affect the reaction, or a mixture thereof.

The reaction temperature is not critical and the reaction is usually carried out under cooling to warming.

Process 21

The compound (I-26) or its salt can be prepared by reacting the compound (I-18) or its salt with malonic acid.

This reaction is carried out in the presence of organic base such as ammonia, primary or secondary amines (e.g., methylamine, dimethylamine, piperidine, etc.), pyridine, picoline, or the like.

The reaction is usually carried out in a conventional solvent such as water, alcohol [e.g., methanol, ethanol, isopropyl alcohol, etc.], tetrahydrofuran, dioxane, toluene, methylene chloride, chloroform, N,N-dimethylformamide, or any other organic solvents which do not adversely affect the reaction, or a mixture thereof.

The reaction temperature is not critical and the reaction is usually carried out under cooling to warming.

Process 22

The compound (I-28) or its salt can be prepared by reacting the compound (I-27) or its salt with a hydroxylamine or its salt.

This reaction can be carried out in the same manner disclosed in Example 117 or a similar manner thereto.

Process 23

The compound (I-29) or its salt can be prepared by reacting the compound (I-28) or its salt with the compound (XIV).

This reaction can be carried out in the same manner disclosed in Example 119 or a similar manner thereto.

Process 24

The object compound (I-31) or its salt can be prepared by condensing a compound (I-30) or its salt and a compound (XV) or its salt.

This reaction may be carried out in a manner such as the Mitunobu reaction or the modification thereof. This reaction can be preferably carried out in the presence of di(lower) alkyl azodicarboxylates (e.g., diethyl azodicarboxylate, etc.) and trialkyl- or triarylphosphines (e.g., triphenylphosphine, etc.).

The reaction is usually carried out in a conventional solvent such as tetrahydrofuran, dioxane, toluene, methylene chloride, chloroform, N,N-dimethylformamide or any other organic solvents which do not adversely affect the reaction, or the mixture thereof.

The reaction temperature is not critical and the reaction is usually carried out under cooling to warming.

The object compounds can be purified and isolated from the reaction mixture and converted to the desired salt in conventional manners, if necessary.

Suitable salts of the compound (I), (I-1) to (I-31), (II), (II-1) and (III) to (XV) may be the same as exemplified for the compound (I).

The object compound (I) or its pharmaceutically acceptable salts thereof possess strong activities as leukotriene and SRS-A antagonists or inhibitors, and are useful for the treatment and/or prevention of allergy or inflammation in human beings or animals, and more particularly for prevention and/or treatment of asthma, psoriasis, hepatitis, bronchitis, gastritis, esophagitis, pancreatitis, arthritis, nephritis, inflammatory bowel disease, shock [e.g., septic shock, anaphylactic shock, etc.], arteriosclerosis, myocardial infarction, cerebral vasospasm, rhinitis, conjunctivitis, eczema, ischemic cerebral disease, chronic obstructive lung disease, cerebral edema, adult respiratory distress syndrome, neonatal pulmonary hypertension, Chrohn's disease, dermatitis (e.g., atopic dermatitis, etc.), rheumatism, gastric ulcer, peptic ulcer, gout, or the like.

In order to illustrate the usefulness of the object compound (I), the pharmacological test data of the representative compound of the compound (I) are shown in the following.

$^3$H-Leukotriene $D_4$ receptor binding (i) Test Method:

(a) Membrane preparation

Human histiocytic lymphoma cells, U937, were homogenized in 5 mH Tris-HCl (pH 7.5) by using Polytoron (Kinematica). The homogenate was centrifuged (1000× g, 10 minutes) to remove tissue clumps and the supernatant was centrifuges (36000× g, 20 minutes) to yield pellets. The pellets were resuspended in buffer (5 mM Tris-HCl pH 7.5), homogenized with a teflon homogenizer and centrifuged (36000× g, 20 minutes) to yield pellets which were referred to as crude membrane fractions. The obtained pellets were stored at −70° C. until use.

(b) $^3$H-Leukotriene $D_4$ binding to preparation membrane

Frozen crude membrane fractions were thawed and resuspended in Medium 1 (10 mM Tris-HCl pH 7.5, 10 mM $CaCl_2$, 10 MM $MgCl_2$, 5 mM cysteine, 5 mM glycine). In binding assays, $^3$H-Leukotriene $D_4$ (0.3 nM) and drug were incubated with 100 μl of the membrane preparation (100 μg protein/tube) in Medium 1 at 25° C. for 30 minutes in a final volume of 500 μl. Separation of receptor-bound from free $^3$H-Leukotriene $D_4$ is achieved by immediate filtration through Whatman GF/B filters under vacuum and washed three times with 5 ml of ice-cold buffer (10 mM Tris-HCl pH 7.5). Non-specific binding was defined as binding in the presence of 1 μM Leukotriene $D_4$. The radioactivity retained on rinsed filters was determined by a liquid-scintillation counter (Packerd TRI-CARB 4530).

(ii) Test Result

| Test Compound (Example No.) | $IC_{50}$ (nM) |
|---|---|
| 21 | <5 |
| 22-2 | <5 |
| 22-16 | <5 |
| 22-23 | <5 |
| 22-24 | <5 |
| 22-27 | <5 |
| 28-3 | <5 |
| 34-3 | <5 |
| 34-5 | <5 |
| 34-8 | <5 |
| 34-10 | <5 |
| 34-11 | <5 |
| 105-1 | <5 |

For therapeutic purpose, the compound (I) and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral or external (topical) administration. The pharmaceutical preparations may be capsules, tablets, dragees, granules, suppositories, solution, lotion, inhalant, ophthalmic preparations, collunarium, suspension, emulsion, ointment, gel, or the like. If desired, there may be included in these preparations, auxiliary substances, stabilizing agents, wetting or emulsifying agents, buffers and other commonly used additives.

While the dosage of the compound (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating the above-mentioned diseases.

In general, amounts between 0.1 mg/body and about 1,000 mg/body may be administered per day.

The following abbreviations have the indicated meanings

Me=methyl
Et=ethyl
nPr=propyl
iPr=isopropyl
nBu=butyl
tBu=tert-butyl
cPen=cyclopentyl
Bzl=benzyl
Bzh=diphenylmethyl
Tet=1H-tetrazol-5-yl
Ph=phenyl The following Preparations and Examples are given for the purpose of illustrating this invention.

PREPARATION 1

A mixture of 3-formyl-5-methylindole (0.50 g), hydroxylamine hydrochloride (0.44 g) and sodium acetate (0.52 g) in acetic acid (5 ml) was stirred for 2 hours, then acetic anhydride (2.5 ml) was added to the mixture and allowed to react under reflux for 0.5 hour. After cooling, the reaction mixture was poured into ice-water and extracted with ethyl acetate. After filtration of insoluble materials, the filtrate was washed with water and brine, dried over magnesium sulfate and evaporated under reduced pressure. The resulting residue was subjected to column chromatography on silica gel and eluted with a mixture of ethyl acetate and chloroform.

The fractions containing the objective compounds were combined and concentrated under reduced pressure to give 3-cyano-5-methylindole (109 mg).

IR (Nujol): 3250, 2200, 1520 cm$^{-1}$

NMR (CDCl$_3$, δ): 2.48 (3H, s), 7.15 (1H, d, J=8.4 Hz), 7.37 (1H, d, J=8.4 Hz), 7.56 (1H, s), 7.69 (1H, d, J=2.9 Hz), 8.79 (1H, br s)

MASS: 157 (M+H)$^+$

PREPARATION 2

The following compounds were prepared by a similar manner to that of Preparation 1.

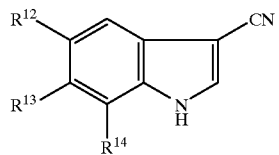

| Preparation | R$^{12}$ | R$^{13}$ | R$^{14}$ | Physical data |
|---|---|---|---|---|
| 2-1 | Cl | H | H | IR (Nujol): 3250, 2200, 1520 cm$^{-1}$<br>NMR (CDCl$_3$, δ): 7.30(1H, dd, J=8.7, 1.9Hz), 7.41(1H, d, J=8.7Hz), 7.70–7.80 (2H, m), 8.77(1H, br s)<br>MASS: 176(M$^+$) |
| 2-2 | F | H | H | IR (Nujol): 3250, 2200, 1170 cm$^{-1}$<br>NMR (DMSO-d$_6$, δ): 7.15(1H, ddd, J=9.2, 9.1, 1.9Hz), 7.42(1H, dd, J=9.2, 2.5Hz), 7.58 (1H, dd, J=9.1, 4.5Hz), 8.32(1H, s), 12.31(1H, br s)<br>MASS: 161(M+H)$^+$ |
| 2-3 | H | Cl | H | IR (Nujol): 3250, 2210, 1170 cm$^{-1}$<br>NMR (DMSO-d$_6$, δ): 7.26(1H, dd, J=8.5, 1.9Hz), 7.63(1H, d, J=1.9Hz), 7.66(1H, d, J=8.5Hz), 8.31(1H, δ), 12.31 (1H, br s)<br>MASS: 176(M)$^+$ |

PREPARATION 3

4-tert-Butylphenylhydrazine hydrochloride (5.0 g) was added to an aqueous sodium hydrogen carbonate solution and the mixture was extracted with ethyl acetate. The extract was dried over magnesium sulfate and evaporated under reduced pressure to give 4-tert-butylphenylhydrazine. A mixture of the hydrazine (4.2 g) obtained above procedure and ethyl pyruvate (3.2 g) in benzene (70 ml) was stirred under reflux azeotropically for 2 hours. After cooling, a solution of p-toluenesulfonic acid in benzene (70 ml) was added to the above mixture, and the mixture was stirred under reflux azeotropically for 2 hours. After cooling, the reaction mixture was filtered and the filtrate was concentrated under reduced pressure. The residue was partitioned between aqueous sodium hydrogen carbonate solution and ethyl acetate. The ethyl acetate layer was washed with brine, dried over magnesium sulfate and evaporated under reduced pressure. The resulting residue was subjected to column chromatography on silica gel and eluted with a mixture of ethyl acetate and n-hexane. The fractions containing the objective compound were combined and concentrated under reduced pressure to give ethyl 5-tert-butylindole-2-carboxylate (4.00 g).

mp: 109–110° C.

IR (Nujol): 3230, 1690, 1530, 1520, 1460, 1320, 1250 cm$^{-1}$

NMR (CDCl$_3$, δ): 1.41 (9H, s), 1.45 (3H, t, J=7.1 Hz), 4.40 (2H, q, J=7.1 Hz), 7.18 (1H, m), 7.24–7.45 (2H, m), 7.65 (1H, d, J=0.8 Hz), 8.94 (1H, br s)

MASS: 246 (M+H)$^+$

PREPARATION 4

A solution of ethyl 5-tert-butylindole-2-carboxylate (3.0 g) and 1N sodium hydroxide solution into a mixed solvent of tetrahydrofuran (20 ml) and methanol (10 ml) was stirred at 40° C. for 5 hours. After removal of solvent, the resulting aqueous solution was made acidic with diluted hydrochloric acid. The resulting precipitates were collected by filtration and washed with water to give 5-tert-butylindole-2-carboxylic acid (2.47 g).

IR (Nujol): 3350, 3100, 1660, 1520, 1460, 1320, 1250 cm$^{-1}$

NMR (CDCl$_3$, δ): 1.41 (9H, s), 7.04 (1H, d, J=2.0 Hz), 7.30–7.40 (2H, m), 7.58 (1H, s), 11.56 (1H, s), 12.80 (1H, br s)

MASS: 218 (M+H)$^+$

PREPARATION 5

A mixture of 5-tert-butylindole-2-carboxylic acid (2.3 g) and cupper powder (0.46 g) in quinoline (20 ml) was stirred at 220° C. for 1 hour. After cooling, the reaction mixture was partitioned between diluted hydrochloric acid and diethyl ether. The ether layer was washed successively with diluted hydrochloric acid 3 times, sodium hydrogen carbonate solution and brine, and dried over magnesium sulfate and evaporated under reduced pressure to give 5-tert-butylindole (2.10 g).

IR (Nujol): 3400, 1720, 1575, 1470, 1415, 1360, 1315 cm$^{-1}$

NMR (CDCl$_3$, δ): 1.39 (9H, s), 6.49–6.52 (1H, m), 7.14–7.17 (1H, m), 7.24–7.34 (2H, m), 7.64 (1H, s), 8.02 (1H, br s)

MASS: 174 (M+H)$^+$

PREPARATION 6

Chlorosulfonyl isocyanate (1 ml) was added dropwise to a suspension of 5-tert-butylindole (2.1 g) in acetonitrile (15 ml) over 10 minutes under ice-cooling. After being stirred for 1 hour at same temperature, a solution of N,N-dimethylformamide (1 ml) in acetonitrile (20 ml) was added to the mixture and then the mixture was stirred at 50° C. for 1 hour. The reaction mixture was poured into ice-water and extracted with ethyl acetate. The extract was washed with brine, dried over magnesium sulfate and evaporated under reduced pressure. The resulting residue was subjected to column chromatography on silica gel and eluted with a mixture of ethyl acetate and n-hexane. The fractions containing the objective compound were combined and concentrated under reduced pressure to give 5-tert-butyl-3-cyanoindole (1.20 g).

mp: 185–187° C.

IR (Nujol): 3250, 2200, 1520 cm$^{-1}$

NMR (CDCl$_3$, δ) 1.49 (9H, s), 7.42 (2H, s), 7.71 (1H, d, J=3.0 Hz), 7.74 (1H, d, J=0.7 Hz), 8.88 (1H, br s)

MASS: 199 (M+H)$^+$

PREPARATION 7

The following compounds were prepared by a similar manner to that of Preparation 6 using appropriate indole.

[Structure: indole/indazole-like ring with R12 at 5-position, R13 at 6-position, R14 at 7-position, and CN at 3-position on an NH-containing bicyclic aromatic]

| Preparation | R$^{12}$ | R$^{13}$ | R$^{14}$ | Physical data |
|---|---|---|---|---|
| 7-1 | ipr | H | H | mp: 160–161° C.<br>IR (Nujol): 3250, 2200, 1520, 1460, 1420, 1380, 1240 cm$^{-1}$<br>NMR (CDCl$_3$, δ):<br>1.32(6H, d, J=7.0Hz), 3.05(1H, sept, J=7.0Hz), 7.22(1H, dd, J=1.6, 8.6Hz), 7.40(1H, d, J=8.6Hz), 7.61(1H, d, J=0.8Hz), 7.70 (1H, d, J=1.8Hz), 8.67(1H, br s)<br>MASS: 185(M+H)$^+$ |
| 7-2 | H | H | Me | mp.: 175–176° C.<br>IR (Nujol):<br>3250, 2200, 1525, 1460, 1440, 1380, 1340, 1330, 1230 cm$^{-1}$<br>NMR (DMSO-d$_6$, δ):<br>2.51(3H, s), 7.06–7.18(2H, m), 7.46(1H, d, J=7.1Hz), 8.26(1H, d, J=3.1Hz), 12.22(1H, br s)<br>MASS: 157(M+H)$^+$ |
| 7-3 | H | Me | H | mp: 149–150° C.<br>IR (Nujol):<br>3250, 2200, 1530, 1500, 1450, 1410, 1360 cm$^{-1}$<br>NMR (DMSO-d$_6$, δ):<br>2.42(3H, s), 7.07(1H, dd, J=1.0, 8.1Hz), 7.34(1H, d, J=1.0Hz), 7.52(1H, d, J=8.1Hz), 8.16 (1H, d, J=2.8Hz), 12.05(1H, br s)<br>MASS: 157 (M+H)$^+$ |
| 7-4 | CF$_3$ | H | H | mp: 163–164° C.<br>IR (Nujol):<br>3200, 2210, 1620, 1600, 1510, 1450, 1430, 1370, 1355, 1340 cm$^{-1}$<br>NMR (CDCl$_3$, δ):<br>7.59(2H, s), 7.86(1H, d, J=3.0Hz), 8.09(1H, s), 9.06(1H, br s)<br>MASS: 210, 211, 212 |
| 7-5 | OBzl | H | H | mp: 158–163° C.<br>IR (Nujol):<br>3200, 2200, 1620, 1580 cm$^{-1}$<br>NMR (DMSO-d$_6$, δ):<br>5.16(2H, s), 6.99(1H, dd, J=2.6, 8.8Hz), 7.18(1H, d, J=2.6Hz), 7.32–7.51 (6H, m), 8.17(1H, d, J=3.0Hz), 12.07(1H, br s)<br>MASS: 249(M+H)$^+$ |
| 7-6 | H | OMe | H | mp: 189–190° C.<br>IR (Nujol):<br>3250, 3100, 2200, 1630, 1580, 1530 cm$^{-1}$<br>NMR (DMSO-d$_6$, δ):<br>3.80(3H, s), 6.88(1H, dd, J=2.2, 8.9Hz), 7.02(1H, d, J=2.2Hz), 7.50 (1H, d, J=8.9Hz), 8.10(1H, d, J=2.9Hz), 11.97(1H, br s)<br>MASS: 173(M+H)$^+$ |

PREPARATION 8

A mixture of 5-benzyloxy-2-nitrophenylacetic acid (4.0 g) and conc. sulphuric acid (0.6 ml) in isopropyl alcohol (40 ml) was stirred under reflux for 1 day. After removal of solvent by evaporation, the resulting residue was dissolved with ethyl acetate. The ethyl acetate extract was washed successively with aqueous sodium hydrogen carbonate solution, water, and brine, and was dried over magnesium sulfate, and concentrated under reduced pressure to give isopropyl 5-benzyloxy-2-nitrophenylacetate (4.20 g).

mp: 143.0–147.8° C.

IR (Nujol): 1740, 1620, 1600, 1510 cm$^{-1}$

NMR (CDCl$_3$, δ): 1.23 (6H, d, J=6.9 Hz), 3.96 (2H, s), 5.00 (1H, sept, J=6.9 Hz), 5.13 (2H, s), 6.87 (1H, d, J=2.8 Hz), 6.96 (1H, dd, J=9.0, 2.8 Hz), 7.34–7.43 (5H, m), 8.18 (1H, d, j=2.8 Hz), 13.68 (1H, br s)

MASS: 330 (M+H)$^+$, 288, 270

PREPARATION 9

A mixture of isopropyl 5-benzyloxy-2-nitrophenylacetate (4.2 g), ammonium chloride (0.42 g) and iron powder (4.2 g) in a mixed solvent of ethanol (20 ml) and water (10 ml) was stirred at 80° C. for 1.2 hours. After cooling, the reaction mixture was filtered and the filtrate was concentrated under reduced pressure. The residue was partitioned between water and ethyl acetate and the ethyl acetate layer was washed with brine, dried over magnesium sulfate and evaporated under reduced pressure to give isopropyl 2-amino-5-benzyloxyphenylacetate (3.9 g).

PREPARATION 10

A mixture of potassium acetate (1.34 g), isopropyl 2-amino-5-benzyloxyphenylacetate (3.9 g) and acetic anhydride (4.0 g) in benzene (40 ml) was stirred at 80° C. After 30 minutes, isopentylnitrite (2.3 g) was added dropwise to the mixture over 15 minutes and then the mixture was stirred at same temperature for 4 hours. After cooling, insoluble mass was filtered off and the filtrate was concentrated under reduced pressure. The residue was dissolved in isopropyl alcohol (30 ml) containing conc. sulphuric acid (0.5 ml) and the mixture was stirred at 80° C. for 3 hours. After cooling to room temperatures the resulting crystals were collected by filtration and washed with isopropyl ether to give isopropyl 5-benzyloxy-1H-indazole-3-carboxylate (2.4 g).

IR (Nujol): 1740, 1620, 1600, 1510 cm$^{-1}$

NMR (DMSO-d$_6$, δ): 1.35 (6H, d, J=6.9 Hz), 5.18 (2H, s), 5.20 (1H, sept, J=6.9 Hz), 7.17 (1H, dd, J=2.4, 9.0 Hz), 7.32–7.50 (1H, m), 7.58 (1H, d, J=9.0 Hz), 13.77 (1H, br s)

MASS: 311 (M+H)$^+$, 269

PREPARATION 11

1-Ethyl-3-(3'-dimethylamino-propyl)carbodiimide (5.87 ml) was added to a mixture of 4-isopropylphenylhydrazine hydrochloride (5.0 g), acetic acid (1.84 ml), triethylamine (3.73 ml) and 1-hydroxybenzotriazole hydrate (40.4 mg) in dichloromethane (50 ml) under ice-cooling and then the mixture was stirred overnight at room temperature. After removal of solvent by evaporation, the resulting residue was partitioned between diluted hydrochloric acid and ethyl acetate. The organic layer was washed successively with aqueous sodium hydrogen carbonate solution, water, and brine, and was dried over magnesium sulfate, and concentrated under reduced pressure. The residue was subjected to column chromatography on silica gel and eluted with a mixture of dichloromethane and methanol. The fractions containing the objective compound were combined and concentrated under reduced pressure to give 1-acetyl-2-(4-iso-propylphenyl)-hydrazine (3.00 g).

mp: 118.7–119.7° C.

IR (Nujol): 3350–3000, 1650 cm$^{-1}$

NMR (CDCl$_3$, δ): 1.20 and 1.22 (6H, d, J=6.9 Hz), 2.05 and 2.11 (3H, s), 2.83 (1H, sept, J=6.9 Hz), 5.74 and 6.10 (6H, br s), 6.69–7.40 (5H, m)

MASS 193 (M+H)$^+$

PREPARATION 12

A suspension of 1-acetyl-2-(4-isopropylphenyl)hydrazine (2.95 g), hydroxylamine hydrochloride (3.49 g) and sodium sulphate (14.32 g) in water (50 ml) containing 1N aqueous hydrochloric acid (15.6 ml) was heated to 100° C. To the homogeneous solution, a solution of chloral hydrate (3.04 g) was rapidly dropped into the reaction mixture and allowed to react at 100° C. for 10 minutes. After cooling at room temperature, the solvent was evaporated to half volume. The resulting residue was extracted with ethyl acetate. The organic layer was washed successively with water, brine, and was dried over magnesium sulfate, and concentrated under reduced pressure. The residue was subjected to column chromatography on silica gel and eluted with a mixture of dichloromethane and methanol. The fractions containing the objective compound were combined and concentrated under reduced pressure to give N-acetylamino-4-isopropyl-isonitrosoacetanilide (2.89 g).

mp: 113.5–115.5° C.

IR (Nujol): 3600–2500 cm$^{-1}$

NMR (CDCl$_3$, δ): 1.20 (6H, d, J=6.9 Hz), 1.96 (3H, s), 2.87 (1H, br s), 7.10–7.40 (4H, m), 7.50 and 8.04 (1H, br s), 9.08 and 10.03 (1H, br s)

MASS: 264 (M+H)$^+$

PREPARATION 13

N-Acetylamino-4-isopropyl-isonitrosoacetanilide (1.87 g) was added portionwise to conc. sulphuric acid at 55° C. The reaction mixture was warmed at 85° C. and reacted at the temperature for 15 minutes. After cooling, the solution was poured into ice (20 g) and the resulting suspension was refluxed for 3.5 hours. The precipitates were filtered, washed with water and a mixture of isopropyl ether and dichloromethane to give 5-isopropyl-1H-indazole-3-carboxylic acid.

mp: >230° C.

IR (Nujol): 3400–2300, 1700 cm$^{-1}$

NMR (CDCl$_3$, δ): 1.26 (6H, d, J=6.9 Hz), 3.04 (1H, sept, J=6.9 Hz), 7.36 (1H, d, J=8.7 Hz), 7.57 (1H, d, J=8.7 Hz), 7.89 (1H, s), 13.68 (1H, br s)

MASS: 205 (M+H)$^+$

Elemental Analysis Calcd. for C$_{11}$H$_{12}$N$_2$O$_2$: C, 64.69, H, 5.92, N, 13.72. Found C, 64.46, H, 5.99, N, 13.62.

PREPARATION 14

A mixture of 5-isopropyl-1H-indazole-3-carboxylic acid (1.44 g) and conc. sulphuric acid (2 drops) in methanol (20 ml) was stirred under reflux for 1 day. After removal of solvent by evaporation, the resulting residue was dissolved with ethyl acetate. The ethyl acetate extract was washed successively with aqueous sodium hydrogen carbonate solution, water, and brine, and was dried over magnesium sulfate, and concentrated under reduced pressure to give methyl 5-isopropyl-1H-indazole-3-carboxylate (1.39 g).

mp: 143.0–147.8° C.

IR (Nujol): 3400–3000, 1720 cm$^{-1}$

NMR (CDCl$_3$, δ): 1.34 (6H, d, J=6.9 Hz), 3.09 (1H, sept, J=6.9 Hz), 3.07 (3H, s), 7.38 (1H, dd, J=8.7, 1.6 Hz), 7.66 (1H, d, J=8.7 Hz), 8.03 (1H, d, J=1.6 Hz), 13.68 (1H, br s)

MASS: 219 (M+H)$^+$

PREPARATION 15

The following compound was obtained according to a similar manner to that of Preparation 14.

Benzyl 1H-indazole-3-carboxylate

IR (Nujol): 3230, 1680, 1585, 1450 cm$^{-1}$

NMR (CDCl$_3$, δ): 5.54 (2H, s), 7.25–7.50 (7H, m), 7.72 (1H, d, J=8.4 Hz), 8.17 (1H, d, J=8.4 Hz)

PREPARATION 16

A mixture of 3-formylindole-5-carboxylic acid (3.47 g), hydroxylamine hydrochloride (1.97 g) and sodium acetate (2.41 g) in acetic acid (30 ml) was stirred for 12 hours, then acetic anhydride (15 ml) was added to the mixture and allowed to react under reflux for 5 hours. After cooling, the reaction mixture was filtered and the filtrate was evaporated under reduced pressure. Methanol was added to the residue and the mixture was reevaporated under reduced pressure. Thionyl chloride (8 ml) and small amounts of N,N-dimethylformamide was added to the residue obtained above in dichloromethane (20 ml). After being stirred for 2 hours at room temperature, the reaction mixture was evaporated under reduced pressure, and the residue was treated with methanol and concentrated under reduced pressure. The residue was partitioned between aqueous sodium hydrogen carbonate solution and ethyl acetate. The ethyl acetate layer was washed with brine, dried over magnesium sulfate and evaporated under reduced pressure. The resulting residue was subjected to column chromatography on silica gel and eluted with a mixture of ethyl acetate and chloroform. The fractions containing the objective compounds were combined and concentrated under reduced pressure to give methyl 3-cyanoindole-5-carboxylate (2.87 g).

IR (Nujol): 3250, 2200, 1720, 1690, 1620, 1520 cm$^{-1}$

NMR (CDCl$_3$, δ): 3.89 (3H, s), 7.66 (1H, d, J=8.6 Hz), 7.90 (1H, dd, J=8.6, 1.6 Hz), 8.26 (1H, d, J=1.6 Hz), 8.42 (1H, s), 12.60 (1H, br s)

MASS : 200 (M)$^+$, 169, 141

PREPARATION 17

A mixture of 4-tert-butyl-2-(5-formylbenzofuran-2-yl) thiazole (1.83 g) and triethyl phosphonoacetate (1.53 ml) in the mixed solvent of tetrahydrofuran (10 ml) and N,N-dimethylformamide (10 ml) was stirred under ice-cooling. After several minutes, potassium tert-butoxide was added to the mixture, which was stirred for 1 hour at same temperature. The resulting mixture was poured into ice-water and extracted with ethyl acetate. The organic layer was washed with brine, dried over magnesium sulfate and concentrated under reduced pressure to give a syrup. The syrup was subjected to column chromatography on silica gel and eluted with a mixture of n-hexane and ethyl acetate. The fractions containing the objective compound were combined and concentrated under reduced pressure to give ethyl (E)-3-[2-(4-tert-butylthiazol-2-yl)benzofuran-5-yl]propenoate (0.68 g).

IR (Nujol): 1705, 1625, 1580, 1500, 1280 cm$^{-1}$

NMR (CDCl$_3$, δ): 1.35 (3H, t, J=7.1 Hz), 1.41 (9H, s), 4.28 (2H, q, J=7.1 Hz), 6.45 (1H, d, J=16.0 Hz), 7.00 (1H, s), 7.34 (1H, s), 7.54 (2H, s), 7.78 (1H, d, J=16.0 Hz), 7.77 (1H, s)

MASS: 356 (M+H)$^+$

PREPARATION 18

A solution of ethyl (E)-3-[2-(4-tert-butylthiazol-2-yl)-benzofuran-5-yl-]propenoate (0.65 g) in tetrahydrofuran (10 ml) was hydrogenated over 10% Pd—C (0.1 g) at room temperature under atmospheric pressure. After removal of the catalyst by filtration the filtrate was concentrated under reduced pressure to give ethyl 3-[2-(4-tert-butylthiazol-2-yl) benzofuran-5-yl]propionate (0.65 g).

IR (Neat): 1725, 1630, 1585, 1500, 1400 cm$^{-1}$

NMR (CDCl$_3$, δ): 1.23 (3H, t, J=6.8 Hz), 1.41 (9H, s), 2.66 (2H, t, J=7.8 Hz), 3.04 (2H, t, J=7.8 Hz), 4.13 (2H, q, J=6.8 Hz), 7.00 (1H, s), 7.23 (1H, dd, J=1.4, 8.0 Hz), 7.30–7.55 (2H, m), 7.75 (1H, d, J=1.4 Hz)

MASS: 358 (M+H)$^+$

PREPARATION 19

Lithium aluminium hydride (0.14 g) was added to a solution of ethyl 3-[2-(4-tert-butylthiazol-2-yl)benzofuran-5-yl]propionate (0.65 g) in tetrahydrofuran (10 ml) at room temperature under an inert atmosphere. After the mixture was stirred for 2 hours, water was added to the mixture. The resulting precipitates were filtered off and the filtrate was extracted with ethyl acetate. The organic layer was washed with brine, dried over magnesium sulfate and concentrated under reduced pressure to give 3-[2-(4-tert-butylthiazol-2-yl)benzofuran-5-yl]propanol (0.42 g).

IR (Nujol): 3250, 3100, 1500, 1460 cm$^{-1}$

NMR (CDCl$_3$, δ): 1.41 (9H, s), 1.80–2.05 (2H, m), 2.81 (2H, t, J=7.4 Hz), 3.69 (2H, t, J=6.2 Hz), 6.96 (1H, s), 7.17 (1H, dd, J=1.8 and 8.4 Hz), 7.28 (1H, s), 7.42 (1H, d, J=1.8 Hz), 7.44 (1H, d, J=8.4 Hz)

MASS: 316 (M+H)$^+$

PREPARATION 20

A mixture of 3-[2-(4-tert-butylthiazol-2-yl)benzofuran-5-yl]propanol (0.40 g) and thionyl chloride (0.4 ml) in dichloromethane (5 ml) was stirred under reflux for 5 hours. After being cooled to room temperature, the solution was concentrated under reduced pressure. The resulting residue -was partitioned between aqueous sodium hydrogencarbonate solution and ethyl acetate. The organic layer was washed with brine, dried over magnesium sulfate and concentrated under reduced pressure to give a 4-tert-butyl-2-[5-(3-chloropropyl)benzofuran-2-yl]thiazole (0.28 g).

IR (Neat): 1585, 1500, 1460 cm$^{-1}$

NMR (CDCl$_3$, δ): 1.41 (9H, s), 2.06–2.20 (2H, m), 2.88 (2H, t, J=7.4 Hz), 3.54 (2H, t, J=6.4 Hz), 6.97 (1H, s), 7.16 (1H, dd, J=2.2, 8.4 Hz), 7.27 (1H, s), 7.43 (1H, d, J=2.2 Hz), 7.45 (1H, d, J=8.4 Hz)

MASS: 334 (M+H)$^+$

PREPARATION 21

Sodium chloride (0.47 g) was added to a mixture of 4-tert-butyl-2-(5-formylbenzofuran-2-yl)thiazole (0.41 g), sodium hydrogenphosphate 12 water (0.23 g) and 2-methyl-2-butane (0.69 ml) in a mixed solvent of water (3 ml), tetrahydrofuran (7.5 ml) and tert-butanol (12.6 ml). After 4 hours, aqueous sodium hydrogensulfide solution was added to the mixture. The resulting mixture was extracted with ethyl acetate. The organic layer was washed with brine, dried over magnesium sulfate and concentrated under reduced pressure. The residue was dissolved in 1N-sodium hydroxide and the solution was treated with carbon powder and acidified with diluted hydrochloric acid. The resulting precipitates were collected and washed with water to give 2-(4-tert-butylthiazol-2-yl)benzofuran-5-carboxylic acid (0.38 g).

IR (Nujol): 2500–2700, 1680, 1610, 1585 cm$^{-1}$ NMR (DMSO-d$_6$, δ): 1.37 (9H, s), 7.53 (1H, s), 7.65 (1H, s), 7.80 (1H, d, J=8.7 Hz), 8.00 (1H, dd, J=1.7 and 8.7 Hz), 8.37 (1H, d, J=1.7 Hz)

MASS: 302 (M+H)$^+$

PREPARATION 22

A solution of 2-(4-tert-butylthiazol-2-yl)benzofuran-5-carboxylic acid (5.0 g) and thionyl chloride (12.1 ml) in tetrahydrofuran (50 ml) was stirred at 50° C. for 2 hours. After the solution was cooled to room temperature, the resulting precipitates were collected by filtration and washed with diisopropyl ether to give 2-(4-tert-butylthiazol-2-yl) benzofuran-5-carbonyl chloride hydrochloride (5.57 g).

IR (Nujol): 2500–2200, 1830, 1790, 1770, 1740, 1600, 1585, 1560 cm$^{-1}$

PREPARATION 23

A solution of 5-benzyloxyindole (0.50 g) in tetrahydrofuran (10 ml) was hydrogenated over 10% Pd—C (0.1 g) at room temperature under 2–3 atoms. After removal of the catalyst by filtration the filtrate was concentrated under reduced pressure. Ethyl 4-bromobutylate (0.475 ml), potassium carbonate (0.443 g) and methylethylketone (10 ml) were added to the residue and the mixture was stirred under reflux for 1 day. After removal of solvent, the resulting residue was subjected to column chromatography on silica gel and eluted with a mixture of ethyl acetate and toluene. The fractions containing the objective compound were combined and concentrated under reduced pressure to give ethyl 4-[(5-indolyl)oxy]butylate (0.39 g).

IR (Neat): 3400, 1720, 1620, 1580, 1470, 1455, 1420 cm$^{-1}$

NMR (CDCl$_3$, δ): 1.26 (3H, t, J=7.1 Hz), 2.13 (2H, quint, J=7.3 Hz), 2.55 (2H, t, J=7.3 Hz), 4.04 (2H, t, J=7.3 Hz), 4.15 (2H, q, J=7.1 Hz), 6.44–6.47 (1H, m), 6.84 (1H, dd, J=2.4, 8.8 Hz), 7.09 (1H, d, J=2.4 Hz), 7.15–7.17 (1H, m), 7.27 (1H, d, J=8.8 Hz), 8.02 (1H, br s)

MASS: 287 (M+H)$^+$, 115

PREPARATION 24

A mixture of 5-acetyl-2-hydroxybenzaldehyde (1.68 g), 2-bromomethyl-4-tert-butylthiazole, potassium carbonate (1.24 g) and potassium iodide (0.59 g) in N,N-dimethylformamide (10 ml) was stirred at room temperature for 5 hours. The resulting mixture was poured into ice-water and extracted with ethyl acetate. The organic layer was washed with brine, dried over magnesium sulfate and concentrated under reduced pressure. A mixture of the resulting syrup and acetic anhydride in xylene was stirred under reflux for 1 day. After being cooled to room temperature, the reaction mixture was concentrated under reduced -pressure. The resulting syrup was subjected to column chromatography on silica gel and eluted with a mixture of toluene and ethyl acetate. The fractions containing the objective compound were combined and concentrated under reduced pressure to give 4-tert-butyl-2-(5-acetylbenzofuran-2-yl)thiazole (1.83 g).

IR (Nujol): 1680, 1600, 1500 cm$^{-1}$ NMR (CDCl$_3$, δ): 1.41 (9H, s), 2.68 (3H, s), 7.02 (1H, s), 7.41 (1H, d, J=0.8 Hz), 7.59 (1H, d, J=8.6 Hz), 8.01 (1H, dd, J=1.8 and 8.6 Hz), 8.27 (1H, d, J=1.8 Hz)

MASS 300 (M-+H)$^+$

PREPARATION 25

A solution of 4-tert-butyl-2-(5-acetylbenzofuran-2 -yl) thiazole (0.6 g) in dichloromethane (5 ml) was added dropwise to a suspension of copper bromide(II) (0.89 g) in ethyl acetate (7 ml) under reflux over 20 minutes. The mixture was stirred under reflux for 9 hours. After being cooled to room temperature, the reaction mixture was poured into water and the mixture was neutralized with aqueous sodium hydrogen carbonate solution. After an insolble mass was filtered off, the filtrate was extracted with ethyl acetate. The extract was washed with brine, dried over magnesium sulfate and concentrated under reduced pressure. The residue was subjected to column chromatography on silica gel and eluted with a mixture of toluene and ethyl acetate. The fractions containing the objective compound were combined and concentrated under reduced pressure to give 4-tert-butyl-2-[5-(bromoacetyl)benzofuran-2-yl]thiazole (0.445 g).

IR (Nujol): 3100, 1685, 1605, 1500, 1430 cm$^{-1}$

NMR (CDCl$_3$, δ): 1.42 (9H, s), 4.52 (2H, s), 7.04 (1H, s), 7.43 (1H, s), 7.63 (1H, d, J=8.7 Hz), 8.02 (1H, dd, J=1.7, 8.7 Hz), 8.30 (1H, d, J=1.7 Hz)

MASS: 380 (M+H)$^+$, 378 (M+H)$^+$

PREPARATION 26

Methyl magnesium bromide (1M) in tetrahydrofuran (12.6 ml) was added dropwise over 30 minutes to a solution of 4-tert-butyl-2-(5-formylbenzofuran-2-yl)thiazole (3.0 g) in tetrahydrofuran (30 ml) under ice-cooling. After being stirred at same temperature for 15 minutes, the reaction mixture was poured into ice-water. The mixture was neutralized with diluted hydrochloric acid and extracted with ethyl acetate. The extract was washed with water and brine, dried over magnesium sulfate and evaporated under reduced pressure. The residue was subjected to column chromatography on silica gel and eluted with a mixture of n-hexane and ethyl acetate. The fractions containing the object compounds were combined and concentrated under recused pressure to give 4 -tert-butyl-2-[5-(1-hydroxyethyl) benzofuran-2-yl] thiazole (2.04 g).

IR (Nujol): 3500–3000 cm$^{-1}$

NMR (CDCl$_{3, δ}$): 1.41 (9H, s), 1.56 (3H, d, J=6.4 Hz), 5.01 (1H, q, J=6.4 Hz), 6.98 (1H, s), 7.31 (1H, s), 7.36 (1H, dd, J=8.6, 1.7 Hz), 7.51 (1H, d, J=8.6 Hz), 7.62 (1H, d, J=1.7 Hz)

MASS: 302 (M+H)$^+$

PREPARATION 27

The following compounds were prepared by a similar manner to that of Preparation 26.

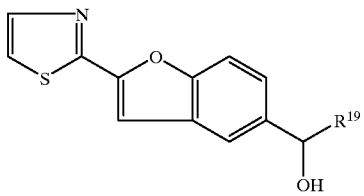

| Preparation | R$^{19}$ | Physical Data |
|---|---|---|
| 27-1 | Et | IR (Nujol): 3500–3000 cm$^{-1}$<br>NMR (CDCl$_3$, δ):<br>0.93(3H, t, J=7.0Hz), 1.42(9H, s),<br>1.81(2H, quint, J=7.0Hz),4.70(1H, t,<br>J=7.0Hz), 6.98(1H, s), 7.33(1H, dd,<br>J=8.5, 1.6Hz), 7.34(1H, s), 7.51(1H, d, |
| 27-2 | Ph | J=8.5Hz), 7.59(1H, d, J=1.6Hz)<br>MASS: 316(M+H)$^+$<br>IR (Nujol): 3500–3000 cm$^{-1}$<br>NMR (CDCl$_3$, δ):<br>1.41(9H, s), 5.96(1H, s), 6.97(1H, s),<br>7.25–7.50(8H, m), 7.65(1H, d, J=1.6Hz)<br>MASS: 364(M+H)$^+$ |

PREPARATION 28

A mixture of 4-tert-butyl-2-[5-(1-hydroxyethyl)-benzofuran-2-yl]thiazole (1.5 g) and thionyl chloride (0.44 ml) in 1,2 dichloroethane (35 ml) was stirred under reflux for 2 hours. After cooling, the resulting mixture was adjusted to pH 7 with aqueous sodium hydrogen carbonate solution. The organic layer was separated, washed with brine, dried over magnesium sulfate and evaporated under reduced pressure to give 4-tert-butyl-2-[5-(1-chloroethyl)-benzofuran-2-yl]thiazole (1.31 g).

IR (Nujol): 1300 cm$^{-1}$

NMR (CDCl$_3$, δ): 1.41 (9H, s), 1.92 (3H, d, J=6.8 Hz), 5.24 (1H, q, J=6.8 Hz), 6.99 (1H, s), 7.31 (1H, s), 7.42 (1H, dd, J=8.6, 1.8 Hz), 7.53 (1H, d, J=8.6 Hz), 7.65 (1H, d, J=1.8 Hz)

MASS: 320 (M+H)$^+$

PREPARATION 29

The following compounds were prepared in a similar manner to that of Preparation 28.

| Preparation | R$^{19}$ | Physical Data |
|---|---|---|
| 29-1 | Et | IR (Nujol): 1250 cm$^{-1}$<br>NMR (CDCl$_3$, δ):<br>1.02(3H, t, J=7.2Hz), 2.19(2H, quint,<br>J=7.2Hz), 4.90(1H, t, J=7.2Hz), 6.98<br>(1H, s), 7.29(1H, s), 7.37(1H, dd, J=8.6,<br>1.8Hz), 7.52(1H, d, J=8.6Hz), 7.61(1H,<br>d, J=1.8Hz)<br>MASS: 334(M+H)$^+$ |
| 29-2 | Ph | NMR (CDCl$_3$, δ):<br>1.55(9H, s), 6.25(1H, s), 7.08–7.50<br>(9H, m), 7.73(1H, s)<br>MASS: 378(M+H)$^+$ |

PREPARATION 30

A mixture of 2-hydroxy-3-methoxybenzaldehyde (3.04 g), ethyl 2-bromopropionate (5.85 g), and potassium carbonate (4.14 g) in dimethylsulfoxide (20 ml) was stirred at 70° C. for 5 hours. The mixture was diluted with water, neutralized with 1N hydrochloric acid, and was extracted with ethyl acetate. The organic layer was separated, washed with brine, dried over magnesium sulfate, and concentrated. The crude product (0.93 g) was purified on a silica gel column (60 g) eluting with a mixed solvent of n-hexane and toluene (from 6:1 to 5:1) to give ethyl 2-(2-formyl-6-methoxyphenoxy)-propionate (5.25 g).

IR (Film): 1735, 1685, 1580 cm$^{-1}$

NMR (CDCl$_3$, δ): 1.23 (3H, t, J=7 Hz), 1.64 (3H, d, J=7 Hz), 3.88 (3H, s), 4.13 (2H, q, J=7 Hz), 5.05 (1H, dd, j=7 Hz), 7.14 (2H, m), 7.47 (1H, m), 10.61 (1H, s)

PREPARATION 31

The following compounds were prepared by a similar manner to that of Preparation 30.

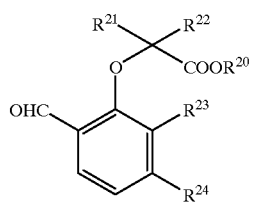

| Preparation | R$^{20}$ | R$^{21}$ | R$^{22}$ | R$^{23}$ | R$^{24}$ | Physical Data |
|---|---|---|---|---|---|---|
| 31-1 | Me | Me | H | OMe | H | [α]$_D^{25}$=−45.43° (c=1.0, CHCl$_3$) <br> ((S)-isomer) <br> IR (Film): 1740, 1685, 1250 cm$^{-1}$ <br> NMR (CDCl$_3$, δ): 1.64(3H, d, J=6.9Hz), 3.72 (3H, s), 3.88(3H, s), 5.05 (1H, s, J=6.9Hz), 7.12(2H, d, J=4.6Hz), 7.44(1H, t, J=4.6Hz), 10.60(1H, s) <br> MASS: 239(M+H)$^+$ |
| 31-2 | Bzh | nPr | H | OMe | H | IR (Film): 1740, 1686, 1580 cm$^{-1}$ <br> NMR (CDCl$_3$, δ): 0.94(3H, t, J=7Hz), 1.3–1.6 (2H, m), 2.0(2H, m), 3.63 (3H, s), 5.17(1H, t, J=6Hz), 6.88(1H, s), 7.0–7.4(13H, m), 10.58(1H, s) |
| 31-3 | Me | Et | H | OMe | H | IR (Film): 1742, 1690, 1585 cm$^{-1}$ <br> NMR (CDCl$_3$, δ): 1.10(3H, t, J=7Hz), 2.04 (2H, m), 3.69(3H, s), 3.86 (3H, s), 5.00(1H, t, J=6Hz), 7.1(2H, m), 7.4(1H, m), 10.63(1H, s) |
| 31-4 | Et | Me | Me | OMe | H | IR (Film): 1730, 1685, 1580 cm$^{-1}$ <br> NMR (CDCl$_3$, δ): 1.34(3H, t, J=7Hz), 1.59 (6H, s), 3.78(3H, s), 4.28 (2H, q, J=7Hz), 7.0–7.2 (2H, m), 7.43(1H, m), 10.48(1H, s) |
| 31-5 | tBu | H | H | OMe | H | NMR (CDCl$_3$, δ): 1.46(9H, s), 3.89(3H, s), 4.72(2H, s), 7.11–7.16 (2H, m), 7.4–7.5 (1H, m), 10.65(1H, s) |
| 31-6 | Me | H | Me | OMe | H | [α]$_D^{25}$=+44.39° (c=0.9, CHCl$_3$) <br> ((R)-isomer) <br> IR (Film): 1740, 1680, 1580, 1470 cm$^{-1}$ |
| 31-7 | Bzh | nPr | H | H | OMe | NMR (CDCl$_3$, δ): 1.64(3H, d, J=6.9Hz), 3.72 (3H, s), 3.88(3H, s), 5.05 (1H, q, J=6.9Hz), 7.09–7.18(2H, m), 7.40–7.49 (1H, m), 10.60(1H, s) <br> MASS: 239(M+H)$^+$ <br> IR (Film): 1750, 1732, 1675, 1600, 1496 cm$^{-1}$ <br> NMR (CDCl$_3$, δ): 0.96(3H, t, J=7Hz), 1.55 (2H, m), 2.0(2H, m), 3.58 (3H, s), 4.81(1H, dd, J=5.2, 7.2Hz), 6.13(1H, d, J=2.2Hz), 6.52(1H, dd, J=2.2, 8.8Hz), 6.92(1H, s), 7.1–7.38(10H, m), 7.82(1H, d, J=8.8Hz), 10.43(1H, s) |

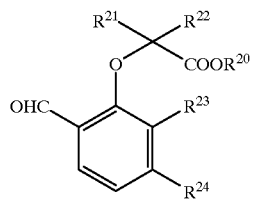

PREPARATION 32

2,4-Dihydroxybenzaldehyde (6.12 g), potassium hydroxide (3.0 g), potassium iodide (2.0 g) were mixed in N,N-dimethylformamide (60 ml). To the mixture was added ethyl 4-bromobutyrate (8.65 g), and the mixture was stirred at room temperature overnight. The reaction mixture was poured into diluted hydrochloric acid and was extracted with ethyl acetate. The organic layer was washed with brine and dried over magnesium sulfate. After concentratration, the crude product was purified on a silica gel column eluting with a mixed solvent of toluene and ethyl acetate (20:1) to give ethyl 4-(4-formyl-3-hydroxyphenoxy)butylate (3.8 g) as an oil.

IR (Neat): 1720, 1625, 1575 cm$^{-1}$

NMR (CDCl$_3$, δ): 1.26 (3H, d, J=7.1 Hz), 2.13 (2H, m), 2.51 (2H, t, J=7 Hz), 4.07 (2H, t, J=6 Hz), 4.15 (2H, q, J=7.1 Hz), 6.41 (1H, d, J=2.2 Hz), 6.52 (1H, dd, J=2.2, 8.6 Hz), 7.42 (1H, d, J=8.6 Hz), 9.71 (1H, s), 11.46 (1H, s)

PREPARATION 33

The following compounds were prepared by a similar manner to that of Preparation 32.

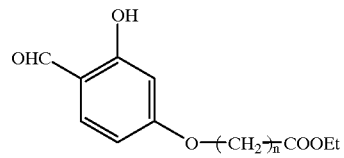

| Preparation | n | Physical Data |
|---|---|---|
| 33-1 | 4 | IR (Nujol): 1725, 1660, 1640, 1615, 1570, 1500, 1460, 1415 cm$^{-1}$ <br> NMR (CDCl$_3$, δ): |

-continued

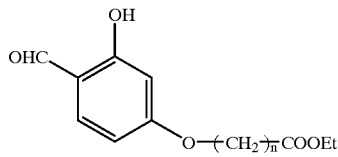

| Preparation | n | Physical Data |
|---|---|---|
| 33-2 | 5 | 1.26(3H, t, J=7.0Hz), 1.80–1.85(4H, m), 2.35–2.42(2H, m), 4.00–4.08(2H, m), 4.14(2H, q, J=7.0Hz), 6.41(1H, d, J=2.2Hz), 6.52(2H, dd, J=2.2, 8.6Hz), 7.42 (1H, d, J=8.6Hz), 9.71(1H, s), 11.47(1H, s) MASS: 267(M+H)$^+$ NMR (CDCl$_3$, δ): 1.26 (3H, t, J=7.0Hz), 1.42–1.95(6H, m), 2.28–2.37(2H, m), 4.00–4.19(4H, m), 6.40 (1H, d, j=2.2Hz), 6.53(1H, dd, J=2.2, 8.6Hz), 7.42(1H, d, J=8.6Hz), 9.71(1H, s), 11.47(1H, s) MASS: 281(M+H)$^+$ |

PREPARATION 34

A mixture of 2-hydroxybenzaldehyde (2.44 g), diphenyl-methyl 2-bromopentanoate (7.26 g), and potassium carbonate (3.45 g) in dimethylsulfoxide (20 ml) was stirred at room temperature for 5 hours. The mixture was diluted with water, neutralized with 1N hydrochloric acid, and was extracted with ethyl acetate. The organic layer was separated, washed with brine, dried over magnesium sulfate, and concentrated to give diphenylmethyl 2-(2-formylphenoxy)-pentanoate (8.04 g).

IR (Film): 1740, 1682, 1590 cm$^{-1}$

NMR (CDCl$_3$, δ): 0.96 (3H, t, J=7.7 Hz), 1.52 (2H, m), 2.03 (2H, m), 4.86 (1H, dt, J=2, 8 Hz), 6.68 (1H, d, J=8 Hz), 6.91 (1H, s), 7.0–7.4 (12H, m), 7.85 (1H, dd, J=2, 8 Hz), 10.59 (1H, s)

PREPARATION 35

The following compounds were prepared by a similar manner to that of Preparation 34.

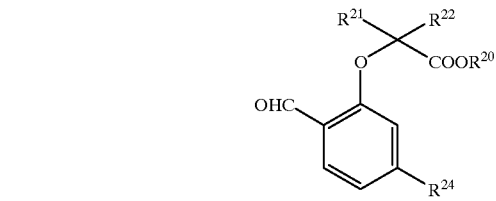

| Preparation | R$^{20}$ | R$^{21}$ | R$^{22}$ | R$^{24}$ | Physical Data |
|---|---|---|---|---|---|
| 35-1 | Bzh | nPr | H | —O—(CH$_2$)$_3$COOEt | IR(Nujol): 1750, 1730, 1675, 1600, 1575, 1500, 1430 cm$^{-1}$ NMR (CDCl$_3$, δ): 0.96 (3H, t, J=7.3Hz), 1.26(3H, t, J=7.2Hz), 1.43–1.60(2H, m), 1.93–2.13(4H, m), 2.46(2H, t, J=7.2Hz), 3.61–3.90(2H, m), 4.15(2H, q, J=7.2Hz), 4.81(1H, dd, J=5.2, 7.2Hz), 6.12(1H, d, J=2.2Hz), 6.50(1H, dd, J=1.4, 8.7Hz), 6.94 (1H, s), 7.10–7.33 (10H, m), 7.82 (1H, d, J=8.7Hz), 10.42 (1H, s) |
| 35-2 | Bzh | nPr | H | —O—(CH$_2$)$_4$COOEt | IR(Nujol): 1750, 1730, 1670, 1600, 1570, 1490 cm$^{-1}$ NMR(CDCl$_3$, δ): 0.95(3H, t, J=7.8Hz), 1.26(3H, t, J=7.0Hz), 1.50–1.60(2H, m), 1.60–1.80(4H, m), 2.00–2.20(2H, m), 2.30–2.50 (2H, m), 3.60–3.90(2H, m), 4.12 (2H, g, J=7.0Hz), 4.75–4.65(1H, m), 6.11(1H, s), 6.50–6.66(1H, m), 6.90(1H, s), 7.10–7.40(10H, m), 7.85(1H, d, J=8.7Hz), 10.42 (1H; s) |
| 35-3 | Bzh | nPr | H | —O—(CH$_2$)$_5$COOEt | IR(Nujol): 1750, 1730, 1675, 1600, 1585, 1490 cm$^{-1}$ NMR(CDCl$_3$, δ): 0.95(3H, t, J=7.4Hz), 1.26(3H, t, J=7.1Hz), 1.40–1.80(8H, m), 1.90–2.20(2H, |

-continued

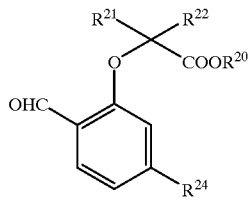

| Preparation | R20 | R21 | R22 | R24 | Physical Data |
|---|---|---|---|---|---|
| | | | | | m), 2.28–2.36(2H, m), 3.60–3.80 (2H, m), 4.09–4.20(2H, m), 4.81 (1H, t, J=7.0Hz), 6.12(1H, s), 6.52(1H, d, J=9.0Hz), 6.91(1H, s), 7.10–7.35(10H, m), 7.82(1H, d, J=8.8Hz), 10.42(1H, s) |
| 35-4 | Bzl | H | H | —O-(CH₂)₃-COOEt | IR(Nujol): 1750, 1730, 1670, 1600, 1540 cm⁻¹ NMR(CDCl₃, δ): 1.26(3H, t, J=7.2Hz), 2.10(2H, quint, J=7.4Hz), 2.49 (2H, t, J=7.4Hz), 3.99(2H, t, J=7.4Hz), 4.15(2H, q, J=7.2Hz), 4.76(2H, 5), 5.25(2H, s), 6.28 (1H, d, J=2Hz), 6.59(1H, dd, J=2, 8.4Hz), 7.35(5H, s), 7.82(1H, d, J=8.4Hz), 10.37(1H, 5) MASS: 401(M + H)⁺ |
| 35-5 | Me | Et | H | —O-(CH₂)₃-COOEt | IR(Nujol): 1750, 1730, 1675, 1600, 1580, 1540, 1440, 1400 cm⁻¹ NMR(CDCl₃, δ): 1.10(3H, t, J=7.4Hz), 1.26(3H, t, J=7.2Hz), 2.00–2.17 (4H, m), 2.50(2H, t, J=7.4Hz), 3.77(3H, s), 4.04(2H, t, J=6.2Hz), 4.15(2H, q, J=7.2Hz), 4.69(1H, t, J=6.0Hz), 6.28(1H, d, J=2.0Hz), 6.55(1H, dd, J=2.0, 8.9Hz), 7.83(1H, d, J=8.9Hz), 10.41(1H, d, J=0.7Hz) MASS: 353(M + H)⁺ |
| 35-6 | Et | Me | Me | H | IR(Film): 1730, 1680, 1660, 1595 cm⁻¹ NMR(CDCl₃, δ): 1.23(3H, t, J=7Hz), 1.69(6H, s), 4.24(2H, q, J=7Hz), 6.78(1H, d, J=8Hz), 7.02(1H, t, J=7.5Hz), 7.45(1H, dt, J=2, 7.5Hz), 7.85(1H, dd, J=2, 8Hz), 10.52(1H, s) |
| 35-7 | Bzh | nBu | H | H | IR(Film): 1750, 1685, 1595 cm⁻¹ NNR(CDCl₃, δ): 0.87(3H, t, J=7.7Hz), 1.4(4H, m), 2.07(2H, m), 4.85(1H, t, J=6Hz), 6.68(1H, d, J=8Hz), 6.92(1H, s), 7.0–7.4 (12H, m), 7.85(1H, dd, J=2, 8Hz), 10.59(1H, s) |
| 35-8 | Et | -(CH₂)₅- | | H | IR(Film): 1725, 1685, 1595 cm⁻¹ |
| 35-9 | Ne | Et | H | H | IR(Film): 1745, 1685, 1598 cm⁻¹ NMR(CDCl₃, δ): 1.06(3H, t, J=7.7Hz), 2.08(2H, dt, J=6, 7Hz), 3.76(3H, s), 4.74(1H, t, J=6Hz), 6.81(1H, d, J=8Hz), 7.06(1H, t, J=8Hz), 7.51(1H, t, J=8Hz), 7.87 (1H, dd, J=2, 8Hz), 10.59(1H, s) |

EXAMPLE 36

The following compound was prepared by a similar manner to that of Preparation 34.

Ethyl 4-(4-formyl-3-methoxyphenoxy)butyrate

IR (Neat): 1730, 1670, 1600, 1575, 1500, 1460, 1430, 1390 cm⁻¹

NMR (CDCl₃, δ): 1.26 (3H, t, J=7.2 Hz), 2.14 (2H, quint, J=7.2 Hz), 3.90 (3H, s), 4.15 (2H, a, J=7.2 Hz), 4.10 (2H, q, J=7.2 Hz), 6.45 (1H, d, J=2.2 Hz), 6.53 (1H, dd, J=2.2, 8.6 Hz), 7.79 (1H, d, J=8.6 Hz), 10.28 (1H, s)

PREPARATION 37 tert-Butyl bromoacetate (1.95 g), and 2,5-dihydroxybenzaldehyde (1.38 g) were dissolved in dimethylsulfoxide (15 ml) and powdered potassium carbonate (2.07 g) was added into it. The mixture was stirred at room temperature for two hours. The mixture was poured into water and acidified with 1N hydrochloric acid and extracted with ethyl acetate. The organic layer was washed with brine and dried over magnesium sulfate. After concentration, the crude product was purified on a silica gel column (40 g) eluting with a mixed solvent of toluene and ethyl acetate (9:1).

From the first fractions, 2,5-bis(tert-butoxycarbonylmethoxy)benzaldehyde (0.58 g) was obtained mp: 89–90° C.

IR (Nujol): 1740, 1680 cm$^{-1}$

NMR (CDCl$_3$, δ): 1.47 (9H, s), 1.49 (9H, s), 4.51 (2H, 5), 4.60 (2H, s), 6.83 (1H, d, J=9 Hz), 7.17 (1H, dd, J=3, 9 Hz), 7.27 (1H, d, J=3 Hz)

From the second fractions, 2-(tert-butoxycarbonylmethoxy)-5-hydroxybenzaldehyde (1.60 g) was obtained:

NMR (CDCl$_3$, δ): 1.49 (9H, s), 4.61 (2H, 5), 6.56 (1H, br s), 6.75 (1H, d, J=9 Hz), 7.03 (1H, dd, J=2.5, 9 Hz), 7.26 (1H, d, J=3 Hz), 10.46 (1H, s)

PREPARATION 38

Ethyl 4-bromobutyrate (1.48 g) and 2-(tert-butoxycarbonylmethoxy)-5-hydroxybenzaldehyde (1.28 g) were dissolved in methyl ethyl ketone (20 ml). To the solution was added powdered potassium carbonate (1.05 g), and the mixture was stirred in an oil bath at 100° C. for seven hours. The reaction mixture was concentrated, diluted with water, and was extracted with ethyl acetate. The organic layer was washed with brine and dried over magnesium sulfate. After concentration, the crude product was purified by a silica gel column (35 g) eluting with a mixed solvent of toluene and ethyl acetate (from 19:1 to 4:1) to give ethyl 4-(4-tert-butoxycarbonylmethoxy-3-formylphenoxy) butyrate as an oil (0.55 g)

IR (Nujol): 1730, 1675 cm$^{-1}$

NMR (CDCl$_3$, δ): 1.25 (3H, d, J=7 Hz), 1.47 (9H, s), 2.01 (2H, m), 2.50 (2H, t, J=7 Hz), 4.00 (2H, t, J=6 Hz), 4.15 (2H, q, J=7 Hz), 4.60 (2H, s), 6.81 (1H, d, J=3 Hz), 7.09 (1H, dd, J=3, 9 Hz), 7.33 (1H, d, J=3 Hz), 10.53 (1H, s)

PREPARATION 39

A solution ethyl 2-(2-formyl-6-methoxyphenoxy) propionate (2.60 g) in tetrahydrofuran-water (9:1) was ice-cooled and sodium borohydride (185 mg) was added. The mixture was stirred at the same temperature for two hours. Diluted hydrochloric acid (1N, 5 ml) was added to the solution and the mixture was stirred for an hour. The mixture was diluted with water and was extracted with ethyl acetate. The organic layer was separated and washed with brine and dried over magnesium sulfate. After concentration, the crude product was purified on a column of silica gel (29 g) eluting with a mixed solvent of toluene and ethyl acetate (7:1) to give ethyl 2-(2-hydroxymethyl-6-methoxyphenoxy) propionate (1.85 g).

IR (Film): 3420, 1730, 1585 cm$^{-1}$

NMR (CDCl$_3$, δ): 1.25 (3H, t, J=7 Hz), 1.60 (3H, d, J=7 Hz), 3.59 (1H, dd, J=5, 8.4 Hz), 3.83 (3H, s), 4.2 (2H, a, J=7 Hz), 4.53 (1H, dd, J=8.4, 12.2 Hz), 4.89 (1H, dd, J=5.0, 12.2 Hz), 5.11 (1H, q, J—7 Hz), 6.82–7.06 (3H, m)

PREPARATION 40

The following compounds were prepared by a similar manner to that of Preparation 39.

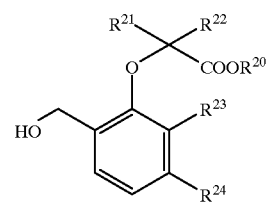

| Preparation | R$^{20}$ | R$^{21}$ | R$^{22}$ | R$^{23}$ | R$^{24}$ | Physical Data |
|---|---|---|---|---|---|---|
| 40-1 | Me | Me ((S)-isomer) | H | OMe | H | [α]$_{25}$$^D$ = 57.69° (c = 0.93, CHCl$_3$)<br>IR(Film): 3600–3000, 1730, 1265 cm$^{-1}$<br>NMR(CDCl$_3$, δ): 1.60(3H, d, J=6.9Hz), 3.73(3H, s), 3.83(3H, s), 3.38(1H, dd, J=5.1, 8.4Hz), 4.55(1H, dd, J=5.1, 8.4Hz), 4.89 (1H, dd, J=5.1, 12.2Hz), 5.12(1H, q, J=6.9Hz), 6.83–7.06(3H, m) |
| 40-2 | Bzh | nPr | H | OMe | H | IR(Film): 3400, 1730, 1582 cm$^{-1}$<br>NMR(CDCl$_3$, δ): 0.93(3H, t, J=7Hz), 1.50(2H, m), 2.0(2H, m), 3.68(3H, s), 4.47(1H, d, J=12Hz), 4.84(1H, d, J=12Hz), 5.30(1H, t, J=6Hz), 6.8–7.0(3H, m), 7.2–7.3(10H, m) |
| 40-3 | Me | Et | H | OMe | H | IR(Film): 3410, 1735, 1585 cm$^{-1}$<br>NMR(CDCl$_3$, δ): 1.08(3H, t, J=7.6Hz), 2.0(2H, m), 3.70(3H, s), 3.82(3H, s), 4.51(1H, d, J=12.1Hz), 4.95(1H, d, J=12.1Hz), 5.73(1H, t, J=6Hz), 6.82–7.26 (3H, m) |
| 40-4 | Et | Me | Me | OMe | H | IR(Film): 3400, 1720, 1582 cm$^{-1}$<br>NMR(CDCl$_3$, δ): 1.34(3H, t, J=7Hz), 1.50(6H, t, J=7Hz), 2.60(1H, br s), 3.74(3H, s), 4.28(2H, q, J=7Hz), 4.65(2H, s), 6.8–7.1(3H, |

-continued

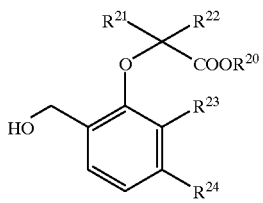

| Preparation | R20 | R21 | R22 | R23 | R24 | Physical Data |
|---|---|---|---|---|---|---|
| 40-5 | tBu | H | H | OMe | H | m)<br>IR(Film): 3400, 1725, 1585 cm⁻¹<br>NMR(CDCl₃, δ): 1.48(9H, s), 3.85 (3H, s), 4.68(2H, s), 4.70(2H, s), 4.2(1H, br s), 6.8–7.1(3H, m) |
| 40-6 | Me | H | Me<br>((R)-isomer) | OMe | H | [α]₂₅^D = +52.43°(c = 1.05, CHCl₃)<br>IR(Film): 3300–3000, 1730, 1580, 1480 cm⁻¹<br>NMR(CDCl₃, δ): 1.60(3H, d, J=6.9Hz), 3.74(3H, s), 3.83(3H, 5), 4.54(1H, d, J=12.2Hz), 4.88 (1H, d, J=12.2Hz), 5.12(1H, d, J=6.9Hz), 6.85(1H, dd, J=2.0, 7.8Hz), 6.88–7.06(2H, m) |
| 40-7 | Bzh | nPr | H | H | OMe | IR(Film): 3400, 1734, 1610, 1588, 1500 cm⁻¹<br>NMR(CDCl₃, δ): 0.95(3H, t, J=7Hz), 1.47(2H, m), 1.97(2H, m), 2.72(1H, dd, J=4.1, 8.4Hz), 3.63(3H, s), 4.47(1H, dd, J=8.2, 12.0Hz), 4.79(1H, dd, J=4.1, 12.0Hz), 4.87(1H, t, J=6.2Hz), 6.29(1H, d, J=2.2Hz), 6.46(1H, dd, J=2.2, 8.2Hz), 6.88(1H, s), 7.1–7.3(11H, m) |

PREPARATION 41

A solution diphenylmethyl 2-(2-formylphenoxy) pentanoate (8.0 g) in tetrahydrofuran-water (9:1, 80 ml) was ice-cooled and sodiumborohydride (380 mg) was added. The mixture was stirred at the same temperature for two hours. To the solution was added 1N hydrochloric acid (20 ml) and the mixture was stirred for an hour. The mixture was diluted with water and was extracted with ethyl acetate. The organic layer was separated and washed with brine and dried over magnesium sulfate. After concentration, the crude product was purified on a column of silica gel (29 g) eluting with a mixed solvent of toluene and ethyl acetate (9:1) to give diphenylmethyl 2-[2-(hydroxymethyl) phenoxy]pentanoate (6.81 g)

IR (Film): 3420, 1730, 1600, 1585 cm⁻¹

NMR (CDCl₃, δ): 0.94 (3H, t, J=7 Hz), 1.5 (2H, m), 2.0 (2H, m), 2.53 (1H, br s), 4.54 (1H, d, J=12.4 Hz), 4.86 (1H, d, J=12.4 Hz), 4.9 (1H, m), 6.70 (1H, d, J=8 Hz), 6.88 (1H, s), 6.96 (1H, d, J=8 Hz), 7.1–7.4 (12H, m)

PREPARATION 42

The following compounds were prepared by a similar manner to that of Preparation 41.

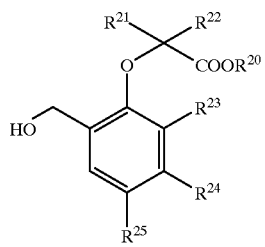

| Preparation | R20 | R21 | R22 | R24 | R25 | |
|---|---|---|---|---|---|---|
| 42-1 | Bzh | nPr | H | —O—(CH₂)₃COOEt | H | IR(Nujol): 3400, 1750, 1730, 1610, 1585, 1500 cm⁻¹<br>NMR(CDCl₃, δ): 0.95(3H, t, J=7.4Hz), |

-continued

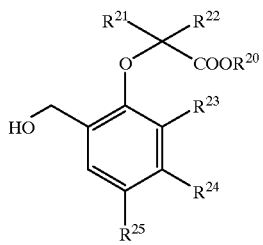

| Preparation | R²⁰ | R²¹ | R²² | R²⁴ | R²⁵ | |
|---|---|---|---|---|---|---|
| | | | | | | 1.26(3H, t, J=7.1Hz), 1.29–1.60(2H, m), 1.90–2.10(4H, m), 2.44(2H, t, J=7.4Hz), 2.70(1H, dd, J=4.6, 8.4Hz), 3.70–3.92(2H, m), 4.14(2H, q, J=7.4Hz), 4.43(1H, d, J=8.4Hz), 4.49 (1H, d, J=8.4Hz), 4.74–4.90(2H, m), 6.28(1H, d, J=2.2Hz), 6.43(1H, dd, J=2.2, 8.4Hz), 6.89(1H, s), 7.11–7.36 (10H, m) |
| 42-2 | Bzh | nPr | H | —O―(CH₂)₄COOEt | H | IR(Nujol): 3400, 1740, 1725, 1610, 1585, 1500, 1450 cm⁻¹ NMR(CDCl₃, δ): 0.95(3H, t, J=7.4Hz), 1.26(3H, t, J=7.1Hz), 1.44–1.54(2H, m), 1.71–1.75(4H, m), 1.93–2.04(2H, m), 2.31–2.38(2H, m), 2.76–2.80(1H, m), 3.65–3.85(2H, m), 4.13(2H, q, J=7.1Hz), 4.4–4.51(1H, m), 4.76–4.90 (2H, m), 6.28(1H, d, J=2.2Hz), 6.43 (1H, dd, J=2.2, 8.6Hz), 6.68(1H, S) 7.11–7.34(10H, m) |
| 42-3 | Bzh | nPr | H | —O―(CH₂)₅COOEt | H | IR(Nujol): 3400, 1740, 1730, 1610, 1585, 1500 cm⁻¹ NMR(CDCl₃, δ): 0.95(3H, t, J=7.4Hz), 1.26(3H, t, J=7.1Hz), 1.4–1.8(8H, m), 1.9–2.1(2H, m), 2.32(2H, t, J=7.4Hz), 2.7–2.8(1H, m), 3.66–3.80(2H, m), 4.13(2H, q, J=7.1Hz), 4.40–4.51(1H, m), 4.75–4.90(2H, m), 6.29(1H, d, J=2.2Hz), 6.44(1H, dd, J=2.2, 8.2Hz), 6.68(1H, s), 7.11–7.32(10H, m) |
| 42-4 | Bzl | H | H | —O―(CH₂)₃COOEt | H | IR(Nujol): 3400, 1720, 1610, 1590, 1500 cm⁻¹ NMR(CDCl₃, δ): 1.26(3H, t, J=7.2Hz), 2.08(2H, quint, J=7.4Hz), 2.49(2H, t, J=7.4Hz), 3.95(2H, t, J=7.4Hz), 4.14 (2H, q, J=7.2Hz), 4.64(2H, s), 4.72 (2H, s), 5.22(2H, s), 6.36(1H, d, J=2.2Hz), 6.48(1H, dd, J=2.2, 8.2Hz), 7.18(1H, d, J=8.2Hz), 7.36(5H, s) |
| 42-5 | Me | Et | H | —O―(CH₂)₃COOEt | H | IR(Nujol): 3400, 1725, 1610, 1585, 1500, 1430 cm⁻¹ NMR(CDCl₃, δ): 1.09(3H, t, J=7.4Hz), 1.26(3H, t, J=7.2Hz), 2.00–2.17(4H, m), 2.49(2H, t, J=7.4Hz), 3.04(1H, br s), 3.74(3H, 3), 3.96(2H, t, J=6.0Hz), 4.14(2H, q, J=7.4Hz), 4.43 (1H, d, J=10.8Hz), 4.75(1H, t, J=6.0Hz), 4.85(1H, d, J=10.8Hz), 6.36 (1H, d, J=2.2Hz), 6.46(1H, dd, J=2.2, 8.2Hz), 7.18(1H, d, J=8.2Hz) |
| 42-6 | Et | Me | Me | H | H | IR(Film): 3400, 1720, 1598 cm⁻¹ NMR(CDCl₃, δ): 1.22(3H, t, J=7Hz), 1.65(6H, s), 4.22(2H, d, J=7Hz), 4.66 (2H, s), 6.73(1H, dd, J=1, 8Hz), 6.96 (1H, m), 7.16(1H, m), 7.30(1H, m) |
| 42-7 | Bzh | nBu | H | H | H | IR(Film): 3400, 1730, 1600, 1585 cm⁻¹ NMR(CDCl₃, δ): 0.87(3H, t, J=7Hz), 1.4(4H, m), 2.0(2H, m), 2.72(1H, br s), 4.54(1H, d, J=12.4Hz), 4.85(1H, d, J=12.4Hz), 4.9(1H, m), 6.70(1H, d, J=8Hz), 6.95(1H, s), 6.96(1H, d, J=8Hz), 7.1–7.4(12H, m) |
| 42-8 | Et | ―(CH₂)₃― | H | H | H | NMR(CDCl₃, δ): 1.11(3H, t, J=7Hz), 1.98–2.1(2H, m), 2.45–2.85(5H, m), |

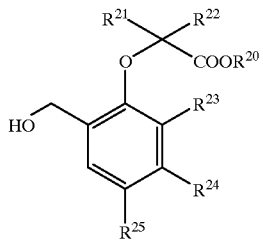

| Preparation | R²⁰ | R²¹ | R²² | R²⁴ | R²⁵ | |
|---|---|---|---|---|---|---|
| 42-9 | Me | Et | H | H | H | 4.15(2H, q, J=7Hz), 4.71(2H, d, J=6.3Hz), 6.44(1H, d, J=8Hz), 6.93 (1H, m), 7.14(1H, m), 7.29(1H, m) IR(Film): 3400, 1730, 1600, 1590 cm⁻¹ NMR(CDCl₃, δ): 1.10(3H, t, J=7Hz), 2.04(2H, m), 3.76(3H, s), 4.52(1H, d, J=12Hz), 4.79(1H, t, J=6Hz), 4.92 (1H, d, J=12Hz), 6.77(1H, d, J=9Hz), 6.96(1H, m), 7.1–7.3(2H, m) |
| 42-10 | tBu | H | H | H | —O—(CH₂)₃—COOEt | IR(Nujol): 3400, 1720 cm⁻¹ NMR(CDCl₃, δ): 1.26(3H, d, J=7Hz), 1.47(9H, s), 2.08(2H, m), 2.50(2H, t, J=7Hz), 2.86(1H, br s), 3.96(2H, t, J=6Hz), 4.14(2H, q, J=7Hz), 4.51 (2H, s), 4.67(2H, s), 6.7(2H, m), 6.8 (1H, m) |
| 42-11 | tBu | H | H | H | —O—CH₂—COOtBt | IR(Nujol): 3430, 1745 cm⁻¹ NMR(CDCl₃, δ): 1.47(9H, s), 1.48(9H, S), 3.45(1H, t, J=7Hz), 4.62(2H, s), 4.54(2H, s), 4.67(2H, d, J=7Hz), 6.7–6.9(3H, m) |

PREPARATION 43

The following compound was prepared by a similar manner to that of Preparation 41.

Ethyl 4-(4-hydroxymethyl-3-methoxyphenoxy)butyrate

IR (Neat): 3400, 1720, 1605, 1585, 1500, 1460, 1420 cm⁻¹

NMR (CDCl₃, δ): 1.26 (3H, t, J=7.2 Hz), 2.03–2.17 (3H, m), 2.51 (2H, t, J=7.3 Hz), 3.84 (3H, s), 4.00 (2H, t, J=6.1 Hz), 4.15 (2H, q, J=7.1 Hz), 4.60 (2H, d, J=5.3 Hz), 6.41 (1H, d, J=2.3 Hz), 6.43–6.50 (2H, m), 7.14 (1H, d, J=8.0 Hz)

PREPARATION 44

Trifluoromethanesulfonic anhydride (0.74 ml) was added dropwise to an ice-cooled mixture of 2-(5-hydroxybenzofuran-2-yl)-4-tert-butylthiazole (1.0 g), N,N-dimethylaminopyridine (67 mg) and 2,6-lutidine (0.52 ml, 4.39 mmol) in dry dichloromethane (10 ml) below 10° C. After being stirred at room temperature for 2 hours, the reaction mixture was washed with diluted hydrochloric acid, then dried over magnesium sulfate and evaporated under reduced pressure. The residue was purified by column chromatography on silica gel using n-hexane-ethyl acetate (4:1) as eluent to give 2-(4-tert-butylthiazol-2-yl)-benzofuran-5-yl trifluoromethanesulfonate as a colorless oil (1.39 g).

IR (Neat): 3100, 2950, 1615, 1585, 1500, 1460, 1430 cm⁻¹

NMR (CDCl₃, δ): 1.41 (9H, s), 7.04 (1H, s), 7.24 (1H, dd, J=2.4 and 7.9 Hz), 7.35 (1H, d, J=0.8 Hz), 7.54 (1H, d, J=2.4 Hz), 7.58 (1H, d, J=7.9 Hz)

MASS: 406 (M+H)⁺

PREPARATION 45

Carbon monoxide was introduced by bubbling to a mixture of 2-(4-tert-butylthiazol-2-yl)benzofuran-5-yl trifluoromethanesulfonate (6.0 g), palladium acetate (99.7 mg), 1,3-bis(diphenylphosphono)propane (183 mg, 0.44 mmol) and triethylamine (4.13 ml) in a mixed solvent of methanol (15 ml) and N,N-dimethylformamide (30 ml) at room temperature for 1 hour. The mixture was warmed to 70° C. and stirred under carbon monoxide balloon for 3 hours. The resulting mixture was filtered through celite and the residue was washed with ethyl acetate. The filtrate and washing solution was combined and evaporated under reduced pressure. The residue was purified by column chromatography on silica gel using ethyl acetate-n-hexane as eluent to give methyl 2-(4-tert-butylthiazol-2-yl)benzofuran-5-carboxylate (3.92 g) as a colorless powder.

IR (Nujol): 3200, 1720, 1610 cm⁻¹

NMR (CDCl₃, δ): 1.42 (9H, s), 3.95 (3H, s), 7.02 (1H, s), 7.39 (1H, s), 7.57 (1H, d, J=8.7 Hz), 8.09 (1H, dd, J=1.7 and 8.7 Hz), 8.36 (1H, d, J=1.7 Hz)

MASS: 316 (M+H)⁺

Example 1

A mixture of crude 4-tert-butyl-2-[5-(thiocarbamoylmethyl)benzofuran-2-yl]thiazole (0.73 g) and ethyl 4-chloroacetoacetate (0.92 g) in ethyl acetate (30 ml) was stirred under reflux for 18 hours. After being cooled, the resulting mixture was poured into aqueous sodium hydrogen carbonate solution and extracted with ethyl acetate. The organic layer was washed with brine, dried over magnesium sulfate and concentrated in reduced pressure. The residue was subjected to column chromatography on silica gel and eluted with ethyl acetate. The fractions containing object compound were combined and concentrated under reduced pressure to give 4-tert-butyl-2-{5-{[4-(ethoxycarbonylmethyl)thiazol-2-yl]methyl}benzofuran-2-yl}thiazole (0.61 g).

IR (Film): 3130, 1740, 1630, 1590, 1520, 1500 cm$^{-1}$

NMR (CDCl$_3$, δ): 1.28 (3H, t, J=7.1 Hz), 1.41 (9H, s), 3.82 (2H, d, J=0.6 Hz), 4.20 (2H, q, J=7.1 Hz), 4.41 (2H, s), 6.98 (1H, s), 7.06 (1H, t, J=0.6 Hz), 7.28 (1H, dd, J=8.5, 1.8 Hz), 7.30 (1H, d, J=0.9 Hz), 7.50 (1H, d, J=8.5 Hz), 7.56 (1H, dd, J=1.8, 0.9 Hz)

MASS: 440 (M$^+$), 425, 368, 270, 254

Example 2

A solution of 4-tert-butyl-2-[5-(thiocarbamoylmethyl)-benzofuran-2-yl]thiazole (740 mg) and 3-bromo-4-oxo-4-phenylbutanoic acid (600 mg) in ethyl acetate (8.0 ml) was heated under reflux for 13.5 hours. After being cooled, the resulting precipitates were collected by filtration and washed with ethyl acetate. The precipitates were dissolved in ethyl acetate, washed with aqueous sodium hydrogen carbonate solution and brine, dried over magnesium sulfate and concentrated under reduced pressure to give a mixture. The mixture was subjected to column chromatography on silica gel and eluted with a mixture of chloroform, methanol and ethyl acetate (20:1:1 to 20:1:2). The fractions containing object compound were combined and concentrated under reduced pressure to give 4-tert-butyl-2-{5-[(5-carboxymethyl-4-phenylthiazol-2-yl)methyl]benzofuran-2-yl}thiazole (72 mg).

mp: 174–180° C.

IR (Nujol): 1710, 1500, 1223, 1182 cm$^{-1}$

NMR (DMSO-d$_6$, δ): 1.36 (9H, s), 3.48 (2H, s), 4.44 (2H, s), 7.35–7.75 (10H, m)

MASS: 488 (M$^+$), 444

Example 3

A mixture of 4-tert-butyl-2-[5-(cyanomethyl)benzofuran-2-yl]thiazole (1.31 g) and thioacetamide in a mixture of 4N-hydrogen chloride of 1,4-dioxane (4 ml) and chloroform was stirred under reflux for 30 minutes and removed the solvent at the same temperature. The residue was washed with water to give crude 4-tert-butyl-2-[5-(thiocarbamoylmethyl)-benzofuran-2-yl]thiazole (1.23 g).

NMR (DMSO-d$_6$, δ): 1.36 (9H, s), 3.93 (2H, s), 7.41 (1H, dd, J=8.5, 1.8 Hz), 7.47 (1H, s), 7.53 (1H, d, J=0.9 Hz), 7.58 (1H, d, J=8.5 Hz), 7.65 (1H, dd, J=1.8, 0.9 Hz)

A mixture of crude 4-tert-butyl-2-[5-(thiocarbamoyl) benzofuran-2-yl]thiazole (1.23 g) and ethyl bromopyruvate (0.86 g) in N,N-dimethylformamide (14 ml) was stirred at 50° C. for 9 hours. The resulting mixture was poured into aqueous sodium hydrogen carbonate solution, extracted with ethyl acetate, washed with brine, dried over magnesium sulfate and concentrated under reduced pressure. The resulting precipitates were washed with diisopropyl ether to give 4-tert-butyl-2-{5-{[4-(ethoxycarbonyl)thiazol-2-yl]methyl}benzofuran-2-yl}thiazole (0.79 g).

IR (Nujol): 3100, 1720, 1590, 1500 cm$^{-1}$

NMR (DMSO-d$_6$, δ) 1.30 (3H, t, J=7.1 Hz), 1.36 (9H, s), 4.29 (2H, q, J=7.1 Hz), 4.50 (2H, s), 7.40 (1H, dd, J=8.6, 1.7 Hz), 7.49 (1H, s), 7.53 (1H, d, J=0.7 Hz), 7.69 (1H, d, J=8.6 Hz), 7.70 (1H, dd, J=1.7, 0.7 Hz), 8.40 (1H, s)

MASS: 426 (M$^+$), 255

Example 4

The following compound was obtained according to a similar manner to that of Example 3.

4-tert-Butyl-2-{5-{[4-(chloromethyl)thiazol-2-yl]methyl}benzofuran-2-yl}thiazole IR (Film): 3140, 1590, 1500 cm$^{-1}$ NMR (CDCl$_3$, δ) 1.41 (9H, s), 4.41 (2H, s), 4.69 (2H, s), 6.98 (1H, s), 7.17 (1H, s), 7.28 (1H, br d, J=8.4 Hz), 7.31 (1H, br s), 7.51 (1H, d, J=8.4 Hz), 7.56 (1H, br s)

MASS: 402 (M$^+$), 301, 270, 254

Example 5

A mixture of 4-tert-butyl-2-{5-{[4-(ethoxycarbonyl)-thiazol-2-yl]methyl}benzofuran-2-yl}thiazole (0.79 g) and sodium hydroxide (0.17 g) in a mixture of water (2 ml) and methanol (6 ml) was stirred under reflux for 3 hours. After being cooled, the resulting solution was concentrated under reduced pressure. The residue was dissolved in water and neutralized with diluted hydrochloric acid. The resulting mixture was extracted with ethyl acetate. The organic layer was washed with brine, dried over magnesium sulfate and concentrated in reduced pressure. The residue was washed with a small amount of ethyl acetate to give 4-tert-butyl-2-{5-{[4-carboxythiazol-2-yl]methyl}benzofuran-2-yl}thiazole (0.69 g).

mp: 227–230° C.

IR (Nujol): 3120, 2600, 1680, 1590, 1490 cm$^{-1}$

NMR (DMSO-d$_6$, δ): 1.36 (9H, s), 4.48 (2H, s), 7.40 (1H, dd, J=8.6, 1.7 Hz), 7.49 (1H, s), 7.53 (1H, d, J=0.7 Hz), 7.69 (1H, d, J=8.6 Hz), 7.70 (1H, dd, J=1.7, 0.7 Hz), 8.32 (1H, s)

MASS: 398 (M$^+$), 255

Example 6

The following compounds were obtained according to a similar manner to that of Example 5.

1) 4-tert-Butyl-2-{5-{[4-(carboxymethyl)thiazol-2-yl]methyl}benzofuran-2-yl}thiazole IR (Nujol): 3140, 2700, 2600, 1730, 1590, 1530, 1500 cm$^{-1}$ NMR (CDCl$_3$, δ): 1.41 (9H, s), 3.87 (2H, d, J=0.8 Hz), 4.43 (2H, s), 6.99 (1H, s), 7.03 (1H, t, J=0.8 Hz), 7.27 (1H, dd, J=8.5, 1.5 Hz), 7.31 (1H, d, J=0.9 Hz), 7.51 (1H, d, J=8.5 Hz), 7.55 (1H, dd, J=1.8, 0.9 Hz)

MASS (m/z): 412 (M$^+$), 368, 270, 254

2) 5-[2-(4-tert-Butylthiazol-2-yl)benzofuran-5-yl]-1-(2-carboxyphenylmethyl)-1H-tetrazole NMR (CDCl$_3$, δ): 1.40 (9H, s), 6.16 (2H, s), 6.93 (1H, d, J=7.2 Hz), 7.02 (1H, s), 7.34 (1H, s), 7.41–7.62 (4H, m), 7.85 (1H, br s), 8.18 (1H, dd, J=7.7, 1.4 Hz)

MASS (m/z): 459 (M$^+$), 325, 297, 282, 267

Example 7

A mixture of 5-[2-(4-tert-butylthiazol-2-yl)benzofuran-5-yl]-2-[2-(ethoxycarbonyl)phenylmethyl]-2H-tetrazole (2.04 g) and 5N aqueous sodium hydroxide (1.5 ml) in a mixture of methanol (20 ml) and tetrahydrofuran (15 ml) was stirred at ambient temperature for one day. The resulting mixture was concentrated under reduced pressure and dissolved with methanol (2 ml). The mixture was allowed to stand until there were no further precipitates separated out. The precipitate were collected by filtration and washed with ethyl acetate to give sodium salt of 5-[2-(4-tert-butylthiazol-2-yl) benzofuran-5-yl]-2-(2-carboxyphenylmethyl)-2H-tetrazole (1.28 g).

mp: 150–151° C.

IR (Nujol): 1610, 1590, 1570, 1530, 1500 cm$^{-1}$

NMR (DMSO-d$_6$, δ): 1.37 (9H, s), 6.52 (2H, s), 6.79 (1H, dd, J=6.8, 2.0 Hz), 7.19–7.29 (2H, m), 7.53 (1H, s), 7.65 (1H, br s), 7.82 (1H, dd, J=6.8, 1.7 Hz), 7.87 (1H, d, J=8.6 Hz), 8.10 (1H, dd, J=8.6, 1.7 Hz), 8.45 (1H, br d, J=1.7 Hz)

MASS (m/z): 282, 267

Example 8

The following compound was obtained according to a similar manner to that of Example 7.

Sodium salt of 5-[2-(4-tert-butylthiazol-2-yl)benzofuran-5-yl]-1-(2-carboxyphenylmethyl)-1H-tetrazole IR (Nujol): 1610, 1590, 1560, 1500 cm$^{-1}$ NMR (DMSO-d$_6$, δ): 1.39 (9H, s), 6.28 (2H, br m), 6.62 (1H, m), 7.18–7.29 (2H, m), 7.53 (1H, s), 7.60 (1H, s), 7.77 (1H, dd, J=8.7, 1.8 Hz), 7.87 (1H, d, J=8.7 Hz), 7.87 (1H, m), 8.21 (1H, br d, J=1.8 Hz)

MASS (m/z): 282, 267

Example 9

A solution of 4-tert-butyl-2-{5-[(4-carboxythiazol-2-yl)methyl]benzofuran-2-yl}thiazole (0.20 g), 2-methylbenzenesulfonamide (0.10 g), 4-dimethylaminopyridine (0.12 g) and 1-(3-dimethylaminopropyl)-3-ethylcarbodiimide hydrochloride (0.19 g) in N,N-dimethylformamide (6 ml) was stirred at ambient temperature for 2 days. The resulting mixture was poured into ice-water and extracted with ethyl acetate. The organic layer was washed with brine, dried over magnesium sulfate and concentrated in reduced pressure. The residue was subjected to column chromatography on silica gel and eluted with ethyl acetate. The fractions containing object compound were combined and concentrated under reduced pressure. The residue was crystallized from diethyl ether and filtered to give 4-tert-butyl-2-{5-{{4-[N-(2-methylphenylsulfonyl)carbamoyl]thiazol-2-yl}methyl}-benzofuran-2-yl}thiazole (0.18 g).

mp: 201–203° C.

IR (Nujol): 1550, 1500 cm$^{-1}$

NMR (DMSO-d$_6$, δ): 1.36 (9H, s), 2.55 (3H, s), 4.41 (2H, s), 7.14–7.38 (4H, m), 7.48 (1H, s), 7.50 (1H, d, J=0.7 Hz), 7.63–7.67 (2H, m), 7.84 (1H, s), 7.87 (1H, dd, J=7.3, 1.5 Hz)

Example 10

A mixture of 4-tert-butyl-2-{5-{[4-(chloromethyl)thiazol-2-yl]methyl}benzofuran-2-yl}thiazole (0.46 g), sodium cyanide (0.22 g) and potassium iodide (0.19 g) in methanol (10 ml) was stirred under reflux for 21 hours. After being cooled, the mixture poured into ice-water and extracted with ethyl acetate. The organic layer was washed with brine, dried over magnesium sulfate and concentrated in reduced pressure to give a syrup. The syrup was subjected to column chromatography on silica gel and eluted with a mixture of ethyl acetate and toluene (1:20). The fractions containing object compound were combined and concentrated under reduced pressure to give 4-tert-butyl-2-{5-{[4-(cyanomethy)thiazol-2-yl]methyl}benzofuran-2-yl}thiazole (0.19 g).

IR (Nujol): 3100, 2250, 1590, 1530, 1500 cm$^{-1}$

NMR (CDCl$_3$, δ): 1.41 (9H, s), 3.89 (2H, d, J=1.0 Hz), 4.39 (2H, s), 6.99 (1H, s), 7.18 (1H, t, J=1.0 Hz), 7.27 (1H, dd, J=8.4, 1.9 Hz), 7.31 (1H, d, J=0.9 Hz), 7.52 (1H, d, J=8.4 Hz), 7.55 (1H, dd, J=1.9, 0.9 Hz)

MASS (m/z): 393 (M$^+$), 254

Example 11

A mixture of 4-tert-butyl-2-{5-{[4-(cyanomethyl)thiazol-2-yl]methyl}benzofuran-2-yl}thiazole (0.19 g), sodium azide (0.43 g) and ammonium chloride (0.36 g) in N,N-dimethylformamide (3 ml) was stirred at 120° C. for 3 days. After being cooled, the mixture was poured into ice-water and extracted with ethyl acetate. The organic layer was washed with brine, dried over magnesium sulfate, and concentrated under reduced pressure to give a syrup. The syrup was subjected to column chromatography on silica gel and eluted with a mixture of chloroform and methanol (50:1), successively with a mixture of chloroform and methanol (10:1). The fractions containing object compound were combined and concentrated under reduced pressure to give 5-{2-{[2-(4-tert-butylthiazol-2-yl)benzofuran-5-yl]methyl}thiazol-4-ylmethyl}-1H-tetrazole (0.12 g).

IR (Nujol): 2740, 1500 cm$^{-1}$

NMR (CDCl$_3$, δ): 1.41 (9H, s), 4.40 (2H, s), 4.44 (2H, s), 6.99 (1H, s), 7.09 (1H, s), 7.24 (1H, br d, J=8.5 Hz), 7.28 (1H, s), 7.50 (1H, d, J=8.5 Hz), 7.51 (1H, br s)

MASS: 436 (M$^+$), 254

Example 12

The following compound was obtained according to a similar manner to that of Example 11.

5-[2-(4-tert-Butylthiazol-2-yl)benzofuran-5-yl]-1H-tetrazole

IR (Nujol): 2700, 1620, 1600, 1570, 1500 cm$^{-1}$

NMR (CDCl$_3$, δ): 1.38 (9H, s), 7.54 (1H, s), 7.71 (1H, d, J=1.0 Hz), 7.95 (1H, d, J=8.7 Hz), 8.08 (1H, dd, J=8.7, 1.7 Hz), 8.45 (1H, dd, J=1.7, 1.0 Hz)

MASS: 325 (M$^+$), 297, 282, 267

Example 13

A mixture of 5-[2-(4-tert-butylthiazol-2-yl)benzofuran-5-yl]-1H-tetrazole (1.55 g), ethyl 2-iodomethylbenzoate (1.67 g) and potassium carbonate (1.80 g) in 2-butanone (15 ml) was stirred under reflux for 5 hours. After being cooled, the resulting mixture was poured into water and extracted with ethyl acetate. The organic layer was washed with brine, dried over magnesium sulfate, and concentrated under reduced pressure. The residue was subjected to column chromatography on silica gel and eluted with a mixture of toluene and ethyl acetate. The fractions containing object compound were combined and concentrated under reduced pressure to give 5-[2-(4-tert-butylthiazol-2-yl)benzofuran-5-yl]-2-[2-(ethoxycarbonyl)phenylmethyl]-2H-tetrazole (2.05 g) and 5-[2-(4-tert-butylthiazol-2-yl)benzofuran-5-yl]-1-[2-(ethoxycarbonyl)phenylmethyl]-1H-tetrazole (0.24 g).

5-[2-(4-tert-Butylthiazol-2-yl)benzofuran-5-yl]-2-[2-(ethoxycarbonyl)phenylmethyl]-2H-tetrazole IR (Film): 3140, 1770, 1720, 1620, 1600, 1580, 1530, 1500 cm$^{-1}$ NMR (CDCl$_3$, δ): 1.42 (9H, s), 1.43 (3H, t, J=7.1 Hz), 4.43 (2H, q, J=7.1 Hz), 6.35 (2H, s), 6.98 (1H, br d, J=7 Hz), 7.01 (1H, s), 7.2 (1H, m), 7.40 (1H, d, J=0.9 Hz), 7.46 (1H, m), 7.63 (1H, d, J=8.6 Hz), 8.10 (1H, br d, J=7 Hz), 8.16 (1H, dd, J=8.6, 1.7 Hz), 8.43 (1H, dd, J=1.7, 0.9 Hz)

MASS (m/z): 487 (M$^+$), 430, 414, 386, 353, 325, 310, 282, 267

5-[2-(4-tert-Butylthiazol-2-yl)benzofuran-5-yl]-1-[2-(ethoxycarbonyl)phenylmethyl]-1H-tetrazole IR (Film): 3120, 1730, 1710, 1600, 1580, 1530, 1500 cm$^{-1}$ NMR (CDCl$_3$, δ): 1.38 (3H, t, J=7.1 Hz), 1.41 (9H, s), 4.33 (2H, q, J=7.1 Hz), 6.18 (2H, s), 6.83 (1H, br d, J=6.2 Hz), 7.03 (1H, s), 7.2 (1H, m), 7.34 (1H, d, J=0.7 Hz), 7.48

(1H, m), 7.55 (1H, dd, J=8.6, 1.7 Hz), 7.62 (1H, d, J=8.6 Hz), 7.83 (1H, dd, J=1.7, 0.7 Hz), 8.14 (1H, br d, J=7.5 Hz)

MASS (m/z): 487 (M$^+$), 458, 414, 386, 353, 324, 310, 287, 267

Example 14

A mixture of 4-tert-butyl-2-[5-(chloromethyl)benzofuran-2-yl]thiazole (0.30 g), benzyl indole-3-acetate (0.25 g), sodium hydroxide (0.24 g) and small amount of cetyl trymethylammonium chloride in dichloromethane (10 ml) was stirred under reflux for 3 hours. After water was added to the reaction mixture, the mixture was neutralized with diluted hydrochloric acid and the resulting mixture was concentrated under reduced pressure. The residue was subjected to column chromatography on silica gel and eluted with a mixture of dichloromethane and methanol. The fractions containing the objective compound were combined and concentrated under reduced pressure to give 1-{[2-(4-tert-butylthiazol-2-yl)benzofuran-5-yl]methyl}indole-3-acetic acid (0.18 g).

mp: 111–115° C. (dec.)

IR (Nujol): 2500–2700, 1710, 1610 cm$^{-1}$

NMR (CDCl$_3$, δ): 1.39 (9H, s), 3.77 (2H, s), 5.28 (2H, s), 6.95 (1H, s), 7.04–7.29 (7H, m), 7.40 (1H, d, J=8.5 Hz), 7.61 (1H, d, J=7.2 Hz)

MASS: 444 (M)$^+$, 400, 270

Example 15

Sodium hydride (60% in mineral oil, 30 mg) was added into a solution of 3-cyano-6-methylindole (73 mg) in N,N-dimethylformamide (2 ml) at room temperature. After 30 minutes, 4-tert-butyl-2-[5-(chloromethyl)benzofuran-2-yl]thiazole (150 mg) and small amount of potassium iodide were added to the solution. After being stirred continuously for 3 hours, the resulting mixture was poured into ice-water and the mixture was acidified with diluted hydrochloric acid and extracted with ethyl acetate. The organic layer was washed with brine, dried over magnesium sulfate and concentrated under reduced pressure to give a syrup. The syrup was subjected to column chromatography on silica gel and eluted with a mixture of toluene and ethyl acetate. The fractions containing the objective compound were combined and concentrated under reduced pressure to give 4-tert-butyl-2-{5-[(3-cyano-6-methylindol-1-yl)methyl]benzofuran-2-yl}thiazole (0.2 g).

mp: 103–105° C.

IR (Nujol): 2200, 1530, 1450, 1350 cm$^{-1}$

NMR (CDCl$_3$, δ): 1.40 (9H, s), 2.75 (3H, s), 5.39 (2H, s), 6.99 (1H, s), 7.09–7.19 (3H, m), 7.27 (1H, d, J=0.9 Hz), 7.37 (1H, d, J=1.4 Hz), 7.52 (1H, d, J=8.5 Hz), 7.56 (1H, s), 7.66 (1H, d, J=8.2 Hz)

MASS: 426 (M+H)$^+$

Example 16

The following compounds were prepared by a similar manner to that of Example 15.

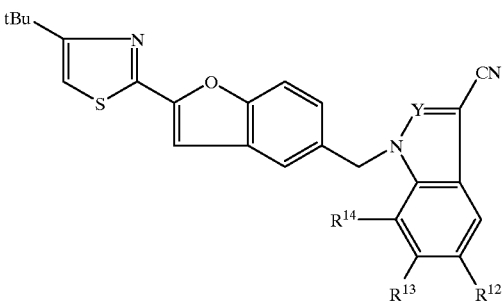

| Example | R$^{12}$ | R$^{13}$ | R$^{14}$ | Y | Physical data |
|---|---|---|---|---|---|
| 16-1 | Me | H | H | CH | IR(Nujol): 2200 cm$^{-1}$<br>NMR(DMSO-d$_6$, δ):<br>1.34(9H, s), 2.40(3H, s), 5.60 (2H, s), 7.12(1H, d, J=7.9Hz), 7.35(1H, d, J=8.2Hz), 7.44–7.69(6H, m), 8.46(1H, s)<br>MASS: 426(M + H)$^+$ |
| 16-2 | H | H | Me | CH | mp: 50–56° C.<br>IR(Nujol): 2200 cm$^{-1}$<br>NMR(CDCl$_3$, δ): 1.40(9H, s), 2.56(3H, s), 5.69 (2H, s), 6.94–7.03(2H, m), 7.00(1H, 3), 7.12 (1H, d, J=1.1Hz), 7.17 (1H, d, J=7.8Hz), 7.23 (1H, d, J=0.9Hz), 7.50 (1H, d, J=8.5Hz), 7.58 (1H, s), 7.65(1H, d, J=7.8Hz)<br>MASS: 426(M + H)$^+$ |
| 16-3 | iPr | H | H | CH | IR(Neat):<br>2950, 2200, 1530, 1480, 1440, 1390, 1350 cm$^{-1}$<br>NMR(CDCl$_3$, δ):<br>1.30(6H, d, J=7.0Hz), 1.40(9H, s), 3.04(1H, hept, J=7.0Hz), 5.40(2H, s), 6.99(1H, s), 7.13(1H, dd, J=1.8, 8.4Hz), 7.18(1H, dd, J=1.6, 8.2Hz), 7.26–7.32 (2H, m), 7.39(1H, s), 7.51(1H, d, J=8.4Hz), 7.60(1H, s), 7.62(1H, s)<br>MASS: 454(M + H)$^+$ |
| 16-4 | tBu | H | H | CH | IR(Neat):<br>2200, 1530, 1480, 1440, 1390, 1355 cm$^{-1}$<br>NMR(CDCl$_3$, δ): 1.39(9H, s), 1.40(9H, s), 5.40 (2H, s), 6.99(1H, s), 7.14(1H, dd, J=1.9, 8.6Hz), 7.27–7.41(4H, m) , 7.51(1H, d, J=8.6Hz), 7.61(1H, s), 7.60(1H, d, J=1.1Hz)<br>MASS: 468(M + H)$^+$ |
| 16-5 | CF$_3$ | H | H | CH | mp: 101–102° C.<br>IR(Nujol): 2210, 1460, 1375, 1320 cm$^{-1}$<br>NMR(CDCl$_3$, δ): 1.40(9H, s), 5.47(2H, s), 7.00 (1H, s), 7.13(1H, dd, J=1.9, 8.6Hz), 7.29(1H, d, J=0.8Hz), 7.40(1H, d, J=1.2Hz), 7.50–7.58(3H, |

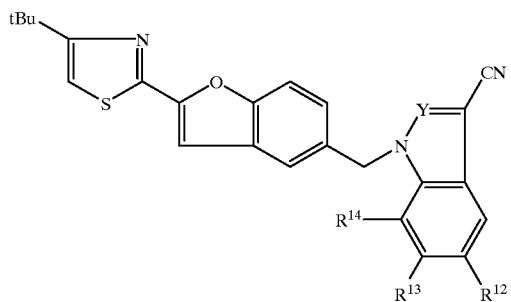

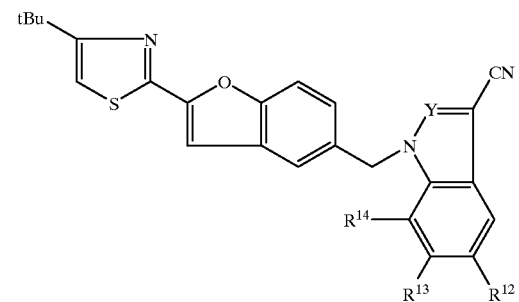

| Example | R$^{12}$ | R$^{13}$ | R$^{14}$ | Y | Physical data |
|---|---|---|---|---|---|
| 16-6 | F | H | H | CH | m), 7.75(1H, s), 8.10 (1H, s) MASS: 480(M + H)$^+$ IR(Nujol): 2200, 1190 cm$^{-1}$ NMR(CDCl$_3$, δ): 1.42(9H, s), 5.42(2H, s), 7.01 (1H, s), 7.01–7.15(2H, m), 7.30(1H, dd, J=9.0, 4.2Hz), 7.40–7.55(4H, m), 7.67(1H, s) MASS: 430(M + H)$^+$ |
| 16-7 | Cl | H | H | CH | IR(Nujol): 3150, 2230, 1530, 1500, 1490 cm$^{-1}$ NMR(CDCl$_3$, δ): 1.40(9H, s), 5.41(2H, s), 7.00 (1H, s), 7.10(1H, dd, J=1.9, 8.5Hz), 7.18–7.32 (3H, m), 7.38(1H, d, J=1.2Hz), 7.52(1H, d, J=8.5Hz), 7.64(1H, s), 7.76(1H, d, J=1.7Hz) MASS: 445(M$^+$), 270 |
| 16-8 | H | Cl | H | CH | IR(Nujol): 2230, 1610, 1535, 1500, 1350 cm$^{-1}$ NMR(CDCl$_3$, δ): 1.40(9H, s), 5.37(2H, s), 7.00 (1H, s), 7.11(1H, dd, J=1.9, 8.5Hz), 7.24–7.29 (2H, m), 7.39(2H, d, J=1.9Hz), 7.52(1H, d, J=8.5Hz), 7.61(1H, s), 7.68(1H, d, J=8.4Hz) MASS: 445(M$^+$), 270 |
| 16-9 | NO$_2$ | H | H | CH | IR(Nujol): 2230, 1620, 1515, 1340 cm$^{-1}$ NMR(CDCl$_3$, δ): 1.40(9H, s), 5.50(2H, s), 7.10(1H, s), 7.14(1H, dd, J=1.9, 8.5Hz), 7.28(1H, d, J=0.9Hz), 7.42(1H, d, J=1.3Hz), 7.49(1H, d, J=9.2Hz), 7.55(1H, d, J=8.5Hz), 7.80(1H, s), 8.20(1H, d, J=9.2, 2.2Hz), 8.72(1H, d, J=2.2Hz) MASS: 456(M$^+$), 426, 270, 255 |
| 16-10 | COOMe | H | H | CH | IR(Nujol): 2200, 1710, 1615, 1530, 1500 cm$^{-1}$ NMR(DMSO-d$_6$, δ): 1.35(9H, s), 3.57(3H, s), 5.68 (2H, s), 7.39(1H, dd, J=1.6, 8.6Hz), 7.46(1H, s), 7.49(1H, s), 7.66–7.75(2H, m), 7.81(1H, d, J=8.6Hz), 7.87–7.94 (1H, m), 8.26(1H, s), 8.71(1H, s) MASS: 469(M$^+$), 438, 286, 270 |
| 16-11 | H | OMe | H | CH | mp: 175–176° C. IR(Nujol): 2200, 1625, 1530, 1495 cm$^{-1}$ NMR(CDCl$_3$, δ): 1.40(9H, s), 3.80(3H, s), 5.37(2H, s), 6.80(1H, d, J=2.2Hz), 6.95(1H, dd, J=2.2, 8.8Hz), 6.99(1H, S), 7.13(1H, dd, J=1.8, 8.5Hz), 7.27(1H, s), 7.38(1H, s), 7.52(1H, d, J=8.5Hz), 7.53(1H, s), 7.65(1H, d, J=8.8Hz) MASS: 442(M + H)$^+$ |
| 16-12 | OBzl | H | H | CH | IR(Nujol): 2200, 1220 cm$^{-1}$ NMR(CDCl$_3$, δ): 1.40(9H, s), 5.12(2H, s), 5.39(2H, s), 6.99(1H, s), 7.01 (1H, dd, J=2.3, 9.0Hz), 7.09–7.53(11H, m), 7.59 (1H, s) MASS: 518(M + H)$^+$ |
| 16-13 | Me | H | H | N | IR(Nujol): 2200 cm$^{-1}$ NMR(CDCl$_3$, δ): 1.40(9H, s), 2.48(3H, s), 5.71(2H, s), 6.98(1H, s), 7.19–7.30(3H, m), 7.36(1H, d, J=8.7Hz), 7.46–7.50 (2H, m), 7.61(1H, s) MASS: 427(M + H)$^+$ |

Example 17

Sodium hydride (60% in mineral oil, 0.15 g) was added into a solution of methyl indole-2-carboxylate (0.56 g) in N,N-dimethylformamide (5 ml) under ice-cooling. After 30 minutes, 4-tert-butyl-2-[5-(chloromethyl)benzofuran-2-yl]thiazole (0.975 g) was added to the solution and then, the mixture was stirred at 50–60° C. for several hours. The resulting mixture was poured into ice-water and extracted with ethyl acetate. The organic layer was washed with brine, dried over magnesium sulfate and concentrated under reduced pressure to give a syrup. The syrup was subjected to column chromatography on silica gel and eluted with a mixture of toluene and ethyl acetate. The fractions containing the objective compound were combined and concentrated under reduced pressure to give methyl 1-{[2-(4-tert-butylthiazol-2-yl)benzofuran-5-yl]methyl}indole-2-carboxyrate (0.87 g).

mp: 108–109° C. (from diisopropyl ether)

IR (Nujol): 1710, 1610, 1590, 1515 cm$^{-1}$

NMR (CDCl$_3$, δ): 1.39 (9H, s), 3.87 (3H, s), 5.93 (2H, s), 6.94 (1H, s), 7.08 (1H, dd, J=1.8, 8.5 Hz), 7.12–7.43 (7H, m), 7.72 (1H, d, J=8.0 Hz)

MASS: 444 (M)$^+$, 286, 270, 254

Example 18

A solution of methyl 1-{[2-(4-tert-butylthiazol-2-yl)benzofuran-5-yl]methyl}indole-2-carboxylate (0.86 g) and sodium hydroxide (0.77 g) in a mixture of water (10 ml) and ethanol (20 ml) was stirred under reflux for 2 hours. After removal of solvents, the residue was dissolved into water and the solution was acidified with diluted hydrochloric acid to pH 3. The resulting precipitates were collected by filtration and dried in vacuo to give 1-{[2-(4-tert-butylthiazol-2-yl)benzofuran-5-yl]methyl}indole-2-carboxylic acid (0.80 g).

mp: 160° C. (dec.)

IR (Nujol): 2500–2700, 1690, 1515, 1500 cm$^{-1}$

NMR (CDCl$_3$, δ) 1.38 (9H, s), 4.0 (1H, br s), 5.92 (2H, s), 6.94 (1H, s), 7.08 (1H, dd, J=1.8, 8.5 Hz), 7.13–7.41 (6H, m), 7.54 (1H, s), 7.73 (1H, d, J=8.0 Hz)

MASS: 430 (M)$^+$, 386, 270, 255

Example 19

A mixture of 1-{[2-(4-tert-butylthiazol-2-yl)benzofuran-5-yl]methyl}indole-2-carboxylic acid (0.46 g) and thionyl chloride (0.16 ml) in benzene (10 ml) was stirred under reflux for 2 hours. After being cooled, the resulting solution was concentrated. The residue was treated with conc. aqueous ammonia solution and extracted with ethyl acetate. The organic layer was washed with brine, dried over magnesium sulfate and evaporated to give 1-{[2-(4-tert-butylthiazol-2-yl)benzofuran-5-yl]methyl}indole-2-carboxamide (0.40 g)

mp: 151–151.5° C.

IR (Nujol): 3350, 3150, 1630, 1600 cm$^{-1}$

NMR (CDCl$_3$, δ): 1.39 (9H, s), 5.80–6.00 (2H, br s), 5.94 (2H, s), 6.94 (1H, s), 7.10–7.34 (6H, m), 7.40 (1H, d, J=8.0 Hz), 7.68 (1H, d, J=7.8 Hz)

MASS: 429 (M$^+$), 411, 385, 270

Example 20

Phosphorus oxychloride (0.14 ml) was added into N,N-dimethylformamide (0.86 ml) under ice-cooling. After 10 minutes, solution of 1-{[2-(4-tert-butylthiazol-2-yl)benzofuran-5-yl]methyl}indole-2-carboxamide (0.43 g) in N,N-dimethylformamide (5 ml) was added to the solution. And then the solution was stirred for several minutes at room temperature and poured into saturated sodium hydrogen carbonate aqueous solution. The resulting precipitates were collected by filtration and washed with water and air-dried to give 4-tert-butyl-2-{5-[(2-cyanoindol-1-yl)methyl]benzofuran-2-yl}thiazol (0.43 g).

IR (Nujol): 2200, 1600, 1500 cm$^{-1}$

NMR (CDCl$_3$, δ): 1.39 (9H, s), 5.58 (2H, s), 6.97 (1H, s), 7.13–7.40 (7H, m), 7.47 (1H, d, J=8.5 Hz), 7.68 (1H, d, J=8.0 Hz)

MASS: 411 (M$^+$), 296, 270, 255

Example 21

The mixture of 4-tert-butyl-2-{5-[(3-cyano-6-methylindol-1-yl)methyl]benzofuran-2-yl}thiazole (0.19 g), sodium azide (0.32 g) and ammonium chloride (0.30 g) in N,N-dimethylformamide (2 ml) was stirred at 120° C. for 72 hours. After being cooled to room temperature, the reaction mixture was poured into ice-water and the mixture was acidified with diluted hydrochloric acid. The resulting precipitates were collected by filtration and air-dried. The precipitates were subjected to column chromatography on silica gel and eluted with a mixture of dichloromethane and methanol. The fractions containing the objective compound were combined and concentrated under reduced pressure to give 5-{1-{[2-(4-tert-butylthiazol-2-yl)benzofuran-5-yl]methyl}-6-methylindol-3-yl}-1H-tetrazole (0.04 g).

mp: 240–245° C.

IR (Nujol): 2500–2700, 1620, 1600, 1490, 1450, 1410 cm$^{-1}$

NMR (DMSO-d$_6$, δ): 1.34 (9H, s), 2.44 (3H, s), 5.64 (2H, s), 7.10 (1H, d, J=8.4 Hz), 7.36 (1H, dd, J=1.7, 8.5 Hz), 7.47 (1H, s), 7.51 (1H, d, J=1.7 Hz), 7.51 (1H, s), 7.63 (1H, s), 7.69 (1H, d, J=8.5 Hz), 8.12 (1H, d, J=8.4 Hz), 8.14 (1H, s)

MASS: 469 (M+H)$^+$

Example 22

The following compounds were prepared by a similar manner to that of Example 21.

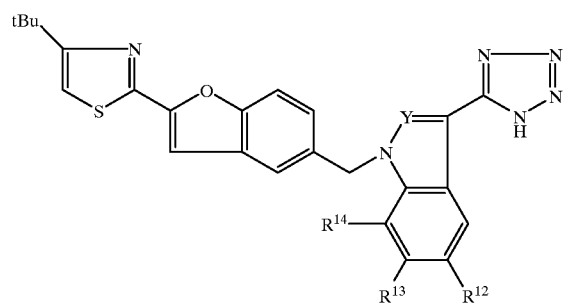

| Example | R$^{12}$ | R$^{13}$ | R$^{14}$ | Y |
|---|---|---|---|---|
| 22-1 | Me | H | H | CH |
| | IR (Nujol): 3500–2500 cm$^{-1}$ | | | |
| | NMR (DMSO-d$_6$, δ): 1.34(9H, s), 2.45 (3H, s), 5.65(2H, s), 7.12(1H, d, J=8.3Hz), 7.35(1H, d, J=8.6Hz), 7.47–7.71(5H, m), 8.05 (1H, s), 8.18(1H, s) | | | |
| | MASS: 469 (M+H)$^+$ | | | |

-continued

[Structure: benzofuran with tBu-thiazole substituent connected via CH2 to an indazole bearing a tetrazole, with R12, R13, R14 substituents]

| Example | R¹² | R¹³ | R¹⁴ | Y |
|---------|-----|-----|-----|---|
| 22-2 | H | H | Me | CH | mp: 165–185° C. (dec.)
IR (Nujol): 3300, 2500–3000, 1610, 1590, 1500, 1450, 1360 cm⁻¹
NMR (CDCl₃, δ): 1.41(9H, s), 2.49(3H, s), 5.52(2H, s), 6.83–7.12(5H, m), 6.95(1H, s), 7.22(1H, d, J=8.6Hz), 7.89(1H, s), 8.17(1H, d, J=8.0Hz)
MASS: 469 (M+H)⁺
Elemental Analysis Calcd. for C₂₆H₂₄N₆OS·¼CH₂Cl₂:
　　　　C 64.37, H 5.04, N 17.16
Found:　C 64.23, H 5.12, N 17.21

| Example | R¹² | R¹³ | R¹⁴ | Y |
|---------|-----|-----|-----|---|
| 22-3 | iPr | H | H | CH | mp: 153–159° C.
IR (Nujol): 3400, 2700, 1620, 1600, 1490, 1400 cm⁻¹
NMR (DMSO-d₆, δ): 1.28(6H, d, J=7.0Hz), 1.34(9H, s), 3.03(1H, hept, J=7.0Hz), 5.65(2H, s), 7.19 (1H, dd, J=2.2, 8.5Hz), 7.37(1H, dd, J=2.1, 8.6Hz), 7.47(1H, s), 7.51(1H, s), 7.59(1H, d, J=8.5Hz), 7.66(1H, d, J=2.2Hz), 7.68(1H, d, J=8.6Hz), 8.10(1H, s), 8.21(1H, s)
MASS: 497 (M+H)⁺
Elemental Analysis Calcd. for C₂₈H₂₈N₆OS·H₂O:
　　　　C 66.04, H 5.82, N 16.50
Found:　C 65.97, H 6.18, N 15.85

| Example | R¹² | R¹³ | R¹⁴ | Y |
|---------|-----|-----|-----|---|
| 22-4 | tBu | H | H | CH | mp: 162–169° C.
IR (Nujol): 3300, 2700–2500, 1620, 1600, 1460, 1380 cm⁻¹
NMR (DMSO-d₆, δ): 1.34(9H, s), 1.36 (9H, s), 5.65(2H, s), 7.37(2H, dd, J=2.2, 8.9Hz), 7.47(1H, s), 7.51(1H, s), 7.59(1H, d, J=8.9Hz), 7.60(1H, d, J=1.8Hz), 7.68(1H, d, J=8.9Hz), 8.20(1H, s), 8.24(1H, d, J=1.8Hz)
MASS: 511 (M+H)⁺

| Example | R¹² | R¹³ | R¹⁴ | Y |
|---------|-----|-----|-----|---|
| 22-5 | CF₃ | H | H | CH | mp: 190–200° C.
IR (Nujol): 3300, 2500–2700, 1630, 1600, 1490, 1460, 1410, 1380, 1340 cm⁻¹
NMR (DMSO-d₆, δ): 1.34(9H, s), 5.78 (2H, s), 7.39(1H, dd, J=2.2, 8.6Hz), 7.48(1H, s), 7.52(1H, s), 7.62(1H, dd, J=1.8, 8.4Hz), 7.69(1H, s), 7.71(1H, d, J=8.4Hz), 7.96(1H, d, J=8.6Hz), 8.42(1H, s), 8.62(1H, s)
MASS: 523 (M+H)⁺
Elemental Analysis Calcd. for C₂₆H₂₁F₃N₆OS·H₂O:
　　　　C 57.80, H 4.29, N 15.55
Found:　C 58.34, H 4.58, N 14.96

| Example | R¹² | R¹³ | R¹⁴ | Y |
|---------|-----|-----|-----|---|
| 22-6 | F | H | H | CH |

-continued

| Example | R¹² | R¹³ | R¹⁴ | Y |
|---|---|---|---|---|
| | | IR (Nujol): 3600–3000, 1180 cm⁻¹ NMR (DMSO-d₆, δ): 1.34(9H, s), 5.69 (2H, s), 7.17(1H, t, J=9.3Hz), 7.38(1H, d, J=8.6Hz), 7.47(1H, s), 7.51(1H, s), 7.67–7.77(3H, m), 7.93(1H, d, J=9.7Hz), 8.31 (1H, s) MASS: 473 (M+H)⁺ | | |
| 22-7 | Cl | H mp: 238° C. (dec.) IR (Nujol): 3300–3500, 3100, 1630, 1600, 1500, 1410 cm⁻¹ NMR (DMSO-d₆, δ): 1.35(9H, s), 5.71 (2H, s), 7.30–7.40(2H, m), 7.47 (1H, s), 7.51(1H, s), 7.67(1H, s), 7.70(1H, d, J=9.5Hz), 7.76 (1H, d, J=8.8Hz), 8.27(1H, d, J=2.0Hz), 8.32(1H, s) MASS: 488 (M⁺), 455, 270, 255 | H | CH |
| 22-8 | H | Cl mp: 245° C. (dec.) IR (Nujol): 2500–3000, 1625, 1600, 1500 cm⁻¹ NMR (DMSO-d₆, δ): 1.36(9H, s), 5.69 (2H, s), 7.30(1H, dd, J=1.8, 8.5Hz), 7.38(1H, dd, J=1.8, 8.5Hz), 7.47(1H, s), 7.53(1H, s), 7.69(1H, s), 7.71(1H, d, J=8.5Hz), 7.89(1H, d, J=1.8Hz), 8.25(1H, d, J=8.5Hz), 8.25(1H, s) MASS: 488 (M⁺), 455, 270, 255 | H | CH |
| 22-9 | NO₂ | H mp: 162° C. (dec.) IR (Nujol): 3300–3000, 1630, 1600, 1510, 1410, 1430 cm⁻¹ NMR (DMSO-d₆, δ): 1.46(9H, s), 5.79 (2H, s), 7.42(1H, dd, J=1.6, 8.6Hz), 7.46(1H, s), 7.51(1H, s), 7.70–7.74(2H, m), 7.96(1H, d, J=9.2Hz), 8.19(1H, dd, J=2.3, 9.2Hz), 8.47(1H, s), 9.18(1H, d, J=2.3Hz) MASS: 500 (M+H)⁺ | H | CH |
| 22-10 | COOMe | H mp: 218° C. (dec.) IR (Nujol): 3200, 2500–2700, 1710, 1650, 1630, 1600, 1500, 1400, 1390 cm⁻¹ NMR (DMSO-d₆, δ): 1.40(9H, s), 3.90 (3H, s), 5.74(2H, s), 7.39(1H, dd, J=1.8, 8.5Hz), 7.47(1H, s), 7.51(1H, s), 7.68(1H, s), 7.70 (1H, d, J=8.5Hz), 7.83(1H, d, J=8.7Hz), 7.91(1H, dd, J=1.5, 8.7Hz), 8.32(1H, s), 8.98(1H, s) MASS: 511 (M−H)⁺ | H | CH |
| 22-11 | H | OMe mp: 239–242° C. IR (Nujol): 3200, 2500–2700, 1620, 1600, 1590, 1460 cm⁻¹ NMR (DMSO-d₆, δ): 1.34(9H, s), 3.82 (3H, s), 5.64(2H, s), 6.92(1H, | H | CH |

-continued

| Example | R¹² | R¹³ | R¹⁴ | Y |
|---------|-----|-----|-----|---|
| | | dd, J=2.2, 8.6Hz), 7.27(1H, d, J=2.2Hz), 7.39(1H, dd, J=1.8, 9.0Hz), 7.47(1H, s), 7.53(1H, s), 7.68(1H, s), 7.69(1H, d, J=8.6Hz), 8.07(1H, s), 8.11(1H, d, J=9.0Hz) MASS: 485 (M+H)⁺ Elemental Analysis Calcd. for $C_{26}H_{24}N_6O_2S \cdot H_2O$: C 62.13, H 5.21, N 16.72 Found: C 62.30, H 5.28, N 16.43 | | |
| 22-12 | OiPr | H | H | CH |
| | | IR (Nujol): 3100–2500, 1200 cm⁻¹ NMR (DMSO-d₆, δ): 1.30(6H, d, J=6.0Hz), 1.34(9H, s), 4.63(1H, hept, J=6.0Hz), 5.63(2H, s), 6.90 (1H, dd, J=8.9, 2.4Hz), 7.37(1H, dd, J=8.5, 1.8Hz), 7.47(1H, s), 7.51(1H, s), 7.56(1H, d, J=8.5Hz), 7.66(1H, s), 7.69(1H, d, J=8.9Hz), 7.72(1H, d, J=2.4Hz), 8.19(1H, s) MASS: 513 (M+H)⁺ | | |
| 22-13 | O.cPen | H | H | CH |
| | | IR (Nujol): 3600–2500, 1200 cm⁻¹ NMR (CDCl₃, δ): 1.39(9H, s), 1.40–2.00(8H, m), 4.82(1H, br s), 5.23(2H, s), 6.88(1H, dd, J=8.9, 2.3Hz), 6.99(1H, s), 7.01(1H, d, J=8.5Hz), 7.07(1H, s), 7.18–7.30 (3H, m), 7.79(1H, d, J=2.3Hz), 7.86(1H, s) MASS: 539 (M+H)⁺ | | |
| 22-14 | OMe | H | H | CH |
| | | mp: 166–170° C. (dec.) IR (Nujol): 3300, 2500–2700, 1630, 1610, 1480, 1460, 1380, 1220 cm⁻¹ NMR (DMSO-d₆, δ): 1.34(9H, s), 3.83 (3H, s), 5.64(2H, s), 6.92(1H, dd, J=2.4, 9.0Hz), 7.36(1H, br d, J=8.5Hz), 7.47(1H, s), 7.51(1H, s), 7.59(1H, d, J=9.0Hz), 7.60–7.72(3H, m), 8.19(1H, s) MASS: 485 (M+H)⁺, 286 | | |
| 22-15 | OH | H | H | CH |
| | | mp: 242° C. (dec.) IR (Nujol): 3600–3000 cm⁻¹ NMR (DMSO-d₆, δ): 1.34(9H, s), 3.35 (1H, br s), 5.59(2H, s), 6.78 (1H, dd, J=2.2, 8.8Hz), 7.36(1H, d, J=8.5Hz), 7.46(1H, s), 7.47 (1H, d, J=8.8Hz), 7.50(1H, s), 7.65(1H, d, J=2.2Hz), 7.69(1H, d, J=8.5Hz) | | |
| 22-16 | —OCH₂—Tet | H | H | CH |
| | | mp: 192–196° C. IR (Nujol): 3700–3000, 1250 cm⁻¹ NMR (DMSO-d₆, δ): 1.34(9H, s), 5.04 (2H, br s), 5.28(2H, s), 5.62 (2H, s), 6.99(1H, dd, J=2.4, 8.9Hz), 7.36(1H, dd, J=1.7, 8.5Hz), 7.47(1H, s), 7.50(1H, | | |

-continued

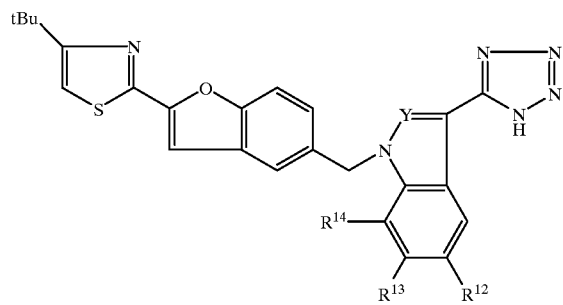

| Example | R¹² | R¹³ | R¹⁴ | Y |
|---|---|---|---|---|
| | | s), 7.58(1H, d, J=8.9Hz), 7.65 (1H, s), 7.68(1H, d, J=8.5Hz), 7.88(1H, d, J=2.4Hz), 8.19(1H, s) | | |
| 22-17 | —OCH₂COOMe | H | H | CH |
| | | mp: 137–139° C. IR (Nujol): 3300–1750, 1630, 1610, 1470, 1380 cm⁻¹ NMR (DMSO-d₆, δ): 1.34(9H, s), 3.72 (3H, s), 4.85(2H, s), 5.65(2H, s), 6.98(1H, dd, J=9.0, 2.5Hz), 7.34(1H, dd, J=1.8, 8.5Hz), 7.47 (1H, s), 7.51(1H, d, J=0.8Hz), 7.61(1H, d, J=9.0Hz), 7.63–7.71 (3H, m), 8.23(1H, s) MASS: 542 (M⁺), 528, 499, 270 | | |
| 22-18 | —OC(Me)₂COOEt | H | H | CH |
| | | mp: 136.8–137.8° C. IR (Nujol): 3200–2300, 1720 cm⁻¹ NMR (CDCl₃, δ): 1.32(3H, t, J=7.12Hz), 1.39(9H, s), 1.57(6H, s), 4.30(2H, q, J=7.12Hz), 5.22 (2H, s), 6.86(1H, dd, J=2.2, 8.9Hz), 6.98(1H, s), 7.01(1H, dd, J=1.8, 8.5Hz), 7.11(1H, s), 7.12(1H, d, J=8.9Hz), 7.23–7.27 (2H, m), 7.81–7.84(2H, m) MASS: 585 (M+H)⁺ | | |
| 22-19 | —OCH₂C(Me)₂COOMe | H | H | CH |
| | | mp: 160° C. (dec.) IR (Nujol): 3200–2300, 1720 cm⁻¹ NMR (DMSO-d₆, δ): 1.28(6H, s), 1.34(9H, s), 3.62(3H, s), 4.05 (2H, s), 5.64(2H, s), 6.90(1H, dd, J=2.3, 9.0Hz), 7.34(1H, d, J=8.5Hz), 7.47(1H, s), 7.50(1H, s), 7.57(1H, d, J=9.0Hz), 7.62–7.71(3H, m), 8.20(1H, s) MASS: 585 (M+H)⁺ | | |
| 22-20 | H | H | H | CMe |
| | | mp: 225–228° C. (dec.) IR (Nujol): 2600, 1620, 1600, 1500 cm⁻¹ NMR (DMSO-d₆, δ): 1.34(9H, s), 2.74(3H, s), 5.70(2H, s), 7.13–7.25(3H, m), 7.42(1H, br s), 7.46(1H, s), 7.47(1H, d, J=0.6Hz), 7.60–7.68(1H, m), 7.66(1H, d, J=8.5Hz), 7.9–8.02 (1H, m) MASS: 469 (M+H)⁺, 307, 270 | | |
| 22-21 | H | H | H | CH |
| | | mp: 143–145° C. (dec.) IR (Nujol): 3400, 3120, 1625, 1600, 1500 cm⁻¹ NMR (DMSO-d₆, δ): 1.34(9H, s), 5.69 (2H, s), 7.26–7.31(2H, m), 7.38 (1H, dd, J=1.8, 8.5Hz), 7.47(1H, s), 7.51(1H, s), 7.67–7.71(3H, m), 8.23–8.27(1H, m), 8.25(1H, s) MASS: 455 (M+H)⁺, 427, 412, 270 | | |
| 22-22 | H | H | H | N |
| | | IR (Nujol): 3300–3000, 1590, | | |

-continued

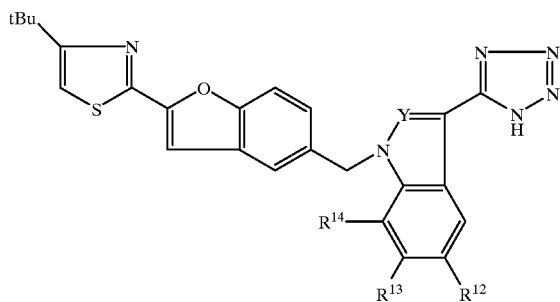

| Example | R¹² | R¹³ | R¹⁴ | Y |
|---------|-----|-----|-----|---|
|  |  | 1490 cm⁻¹<br>NMR (DMSO-d₆, δ): 1.34(9H, s),<br>5.91(2H, s), 7.29–7.40(2H, m),<br>7.46(1H, s), 7.51(1H, s), 7.46–<br>7.54(1H, m), 7.63–7.68(2H, m),<br>7.88(1H, d, J=8.6Hz), 8.35(1H,<br>d, J=8.1Hz)<br>MASS: 456 (M+H)⁺, 413 |  |  |
| 22-23 | OMe | H<br>mp: 140–145° C. (dec.)<br>IR (Nujol): 3300, 3100, 1625,<br>1600, 1500 cm⁻¹<br>NMR (DMSO-d₆, δ): 1.34(9H, s),<br>3.88(3H, s), 5.92(2H, s), 7.21<br>(1H, dd, J=2.3, 9.2Hz), 7.36(1H,<br>d, J=8.6Hz), 7.46(1H, s), 7.50<br>(1H, s), 7.60–7.70(3H, m), 7.86<br>(1H, d, J=9.2Hz)<br>MASS: 486 (M+H)⁺, 460, 270<br>Elemental Analysis Calcd. for<br>C₂₅H₂₃N₇O₂S.½H₂O:<br>    C 60.71, H 4.89, N 19.84<br>observed: C 60.75, H 4.99, N 18.94 | H | N |
| 22-24 | —OH | H<br>IR (Nujol): 3300–3000, 2500–2700,<br>1590 cm⁻¹<br>NMR (DMSO-d₆, δ): 1.34(9H, s),<br>5.88(2H, s), 7.07(1H, dd, J=2.3,<br>9.0Hz), 7.35(1H, dd, J=1.8,<br>8.5Hz), 7.47(1H, s), 7.51(1H,<br>s), 7.61–7.69(3H, m), 7.75(1H,<br>d, J=9.0Hz), 9.65(1H, s)<br>MASS: 472 (M+H)⁺ | H | N |
| 22-25 | —OCH₂COOEt | H<br>mp: 120–121° C.<br>IR (Nujol): 3500, 3100, 2500–2700,<br>1750, 1730, 1605, 1500 cm⁻¹<br>NMR (DMSO-d₆, δ): 1.24(3H, t,<br>J=7.1Hz), 1.34(9H, s), 4.20(2H,<br>q, J=7.1Hz), 4.90(2H, s), 5.93<br>(2H, s), 7.28(1H, dd, J=2.4,<br>9.1Hz), 7.36(1H, d, J=2.4Hz),<br>7.47(1H, s), 7.51(1H, s), 7.60–<br>7.69(3H, m), 7.89(1H, d,<br>J=9.2Hz)<br>MASS: 558 (M+H)⁺<br>Elemental Analysis Calcd. for<br>C₂₈H₂₇N₇O₄S.1.2H₂O:<br>    C 58.06, H 5.12, N 16.93<br>Found: C 58.04, H 4.96, N 16.74 | H | N |
| 22-26 | iPr | H<br>mp: 132.5° C. (dec.)<br>IR (Nujol): 3600–2300 cm⁻¹<br>NMR (DMSO-d₆, δ): 1.29(6H, d,<br>J=6.9Hz), 3.10(1H, hept,<br>J=6.9Hz), 5.93(2H, s), 7.37(1H,<br>dd, J=1.7, 8.6Hz), 7.46(1H, s),<br>7.49(1H, d, J=8.8Hz), 7.51(1H,<br>s), 7.65(1H, s), 7.67(1H, d,<br>J=8.6Hz), 7.86(1H, d, J=8.8Hz),<br>8.14(1H, s)<br>MASS: 498 (M+H)⁺ | H | N |

-continued

| Example | R$^{12}$ | R$^{13}$ | R$^{14}$ | Y |
|---|---|---|---|---|
| 22-27 | Me | H | H | N |
| | mp: 134° C. (dec.) | | | |
| | IR (Nujol): 3600–3000 cm$^{-1}$ | | | |
| | NMR (CDCl$_3$, δ): 1.41(9H, s), 1.72 (3H, s), 5.57(2H, s), 6.94–7.02 (3H, m), 7.13(1H, s), 7.22–7.26 (3H, m), 7.36(1H, d, J=8.7Hz), 8.17(1H, br s) | | | |
| | MASS: 470 (M+H)$^+$ | | | |
| 22-28 | H | —COOMe | H | CH |
| | mp: 143.0–147.8° C. | | | |
| | IR (Nujol): 3300, 3100, 2500–2700, 1715, 1630, 1600, 1500, 1235 cm$^{-1}$ | | | |
| | NMR (DMSO-d$_6$, δ): 1.34(9H, s), 3.87(3H, s), 5.81(2H, s), 7.37 (1H, dd, J=1.9, 8.5Hz), 7.47(1H, s), 7.52(1H, s), 7.65(1H, s), 7.71(1H, d, J=8.5Hz), 7.89(1H, dd, J=1.4, 8.4Hz), 8.33(1H, br s), 8.35(1H, d, J=8.4Hz), 8.43 (1H, s) | | | |
| | MASS: 531 (M+H)$^+$ | | | |
| 22-29 | H | -(CH$_2$)$_4$COOEt | H | CH |
| | IR (Nujol): 3300, 3100, 2500–2700, 1735, 1630, 1605, 1500, 1250 cm$^{-1}$ | | | |
| | NMR (DMSO-d$_6$, δ): 1.13(3H, t, J=7.1Hz), 1.34(9H, s), 1.40–1.70 (4H, m), 2.67(2H, t, J=7.1Hz), 2.60–2.75(2H, m), 4.01(2H, q, J=7.1Hz), 5.65(2H, s), 7.11(1H, d, J=8.3Hz), 7.35(1H, d, J=8.5Hz), 7.47(1H, s), 7.51(2H, s), 7.66(1H, br s), 7.68(1H, d, J=8.5Hz), 8.13(1H, d, J=8.5Hz), 8.15(1H, s) | | | |
| | MASS: 531 (M+H)$^+$ | | | |
| 22-30 | —CH$_2$OH | H | H | CH |
| | mp: 196–198° C. (dec.) | | | |
| | IR (Nujol): 3300–3100, 2500–2700, 1630, 1605, 1500, 1250 cm$^{-1}$ | | | |
| | NMR (DMSO-d$_6$, δ): 1.41(9H, s), 4.61 (2H, s), 5.17(1H, br s), 5.66 (2H, s), 7.25(1H, d, J=8.4Hz), 7.35(1H, d, J=8.6Hz), 7.47(1H, s), 7.51(1H, s), 7.65–7.70(3H, m), 8.13(1H, d, J=8.5Hz), 8.15 (1H, s) | | | |
| | MASS: 485 (M+H)$^+$, 440 | | | |
| 22-31 | -(CH$_2$)$_2$COOH | H | H | CH |
| | mp: 217° C. (dec.) | | | |
| | IR (Nujol): 3300–3100, 2500–2700, 1700, 1620, 1600, 1250 cm$^{-1}$ | | | |
| | NMR (DMSO-d$_6$, δ): 1.34(9H, s), 2.52–2.60(2H, m), 2.90–3.00(2H, m), 5.64(2H, s), 7.17(1H, d, J=8.5Hz), 7.37(1H, d, J=8.5Hz), 7.47(1H, s), 7.51(1H, s), 7.60 (1H, d, J=8.5Hz), 7.66(1H, s), 7.68(1H, d, J=8.6Hz), 8.08(1H, s), 8.20(1H, s) | | | |
| | MASS: 527 (M+H)$^+$ | | | |
| 22-32 | H | H | —OCH$_2$COOMe | CH |

-continued

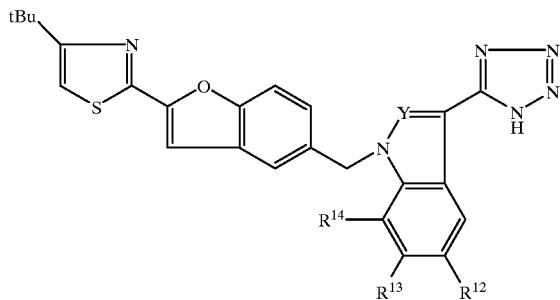

| Example | R$^{12}$ | R$^{13}$ | R$^{14}$ | Y |
|---------|----------|----------|----------|---|
| | mp: 217° C. (dec.) IR (Nujol): 3100, 2500–2700, 1760, 1625, 1600, 1580, 1500, 1450, 1290, 1200, 1180, 1100 cm$^{-1}$ NMR (DMSO$_6$, δ): 1.34(9H, s), 3.33 (3H, s), 4.98(2H, s), 5.95(2H, s), 6.83(1H, s, J=7.7Hz), 7.15 (1H, t, J=7.7Hz), 7.38(1H, dd, J=1.7, 8.6Hz), 7.46(1H, s), 7.49(1H, d, J=0.7Hz), 7.65(1H, d, J=8.6Hz), 7.66(1H, dd, J=0.7, 1.7Hz), 7.86(1H, d, J=7.5Hz), 8.17(1H, s) MASS: 543 (M+H)$^+$, 286 | | | |

Example 23

Sodium hydride (60% in mineral oil, 0.81 g) was added into a solution of 5-benzyloxyindole-3-acetic acid (2.5 g) in N,N-dimethylformamide (40 ml) at room temperature. After 30 minutes, 4-tert-butyl-2-[5-(chloromethyl)benzofuran-2-yl]thiazole (2.71 g) was added to the solution. After being stirred continuously for 4 hours, the resulting mixture was poured into ice-water and the mixture was acidified with diluted hydrochloric acid. The resulting precipitates were collected by filtration and subjected to column chromatography on silica gel and eluted with a mixture of dichloromethane and methanol. The fractions containing the objective compound were combined and concentrated under reduced pressure. The residue was crystallized with aqueous ethanol and the crystals were collected by filtration and washed with aqueous ethanol to give 5-benzyloxy-1-{[2-(4-tert-butylthiazol-2-yl)benzofuran-5-yl]methyl}indole-3-acetic. acid (4.15 g).

IR (Nujol): 2500–2700, 1700, 1480 cm$^{-1}$

NMR (CDCl$_3$, δ): 1.40 (9H, s), 3.78 (2H, s), 5.08 (2H, s), 5.31 (2H, s), 6.91 (1H, dd, J=1.8, 8.9 Hz), 6.96 (1H, s), 7.06–7.47 (12H, m)

MASS: 551 (M+H)$^+$, 286

Example 24

A mixture of 5-benzyloxy-1-{[2-(4-tert-butylthiazol-2-yl)benzofuran-5-yl]methyl}indole-3-acetic acid (3.0 g), 10% Pd—C (0.6 g) and ammonium formate (2.0 g) in a mixed solvents of ethanol (60 ml) and water (6 ml) was stirred under reflux for 18 hours. After removal of the catalysts by filtration, the filtrate was concentrated under reduced pressure. The residue was dissolved in 10% hydrogen chloride in methanol (200 ml) and the mixture was stored in refrigerator for 2 days. The resulting solution was concentrated under reduced pressure and the residue was partitioned between aqueous sodium hydrogen carbonate solution and ethyl acetate. The organic layer was washed with brine, dried over magnesium sulfate and concentrated under reduced pressure to give methyl 1-{[2-(4-tert-butylthiazol-2-yl)benzofuran-5-yl]methyl}-5-hydroxyindole-3-acetate (1.76 g).

IR (Neat): 3300, 1720, 1610, 1580, 1360 cm$^{-1}$

NMR (CDCl$_3$, δ): 1.40 (9H, s), 3.69 (3H, s), 3.71 (2H, s), 5.29 (2H, s), 6.76 (1H, dd, J=0.5, 8.8 Hz), 6.98 (1H, s), 7.02 (1H, d, J=0.5 Hz), 7.06–7.12 (3H, m), 7.25–7.33 (2H, m), 7.43 (1H, d, J=8.5 Hz)

MASS: 475 (M+H)$^+$

Example 25

A mixture of methyl 1-{[2-(4-tert-butylthiazol-2-yl)benzofuran-5-yl]methyl}-5-hydroxyindole-3-acetate (0.35 g), ethyl 5-bromopentanoate (0.232 ml) and potassium carbonate (0.31 g) in methylethylketone (5 ml) was stirred at 80° C. for 18 hours. After an insoluble mass was filtered off, the filtrate was concentrated under reduced pressure. The resulting syrup was subjected to column chromatography on silica gel and eluted with a mixture of ethyl acetate and n-hexane. The fractions containing the objective compound were combined and concentrated under reduced pressure. The residue was crystallized with n-hexane and the crystals were collected by filtration and washed with n-hexane to give methyl 1-{[2-(4-tert-butylthiazol-2-yl)benzofuran-5-yl]-methyl}-5-(4-ethoxycarbonylbutoxy)indole-3-acetate (0.23 g).

IR (Nujol): 1725, 1610, 1585, 1460, 1360 cm$^{-1}$

NMR (CDCl$_3$, δ): 1.25 (3H, t, J=7.1 Hz), 1.40 (9H, s), 1.81–1.88 (4H, m), 2.35–2.39 (2H, m), 3.71 (3H, s), 3.75 (2H, s), 4.00–4.05 (2H, m), 4.13 (2H, q, J=7.1 Hz), 5.33 (2H, s), 6.83 (1H, dd, J=2.3, 8.8 Hz), 6.97 (1H, s), 7.06 (1H, d, J=2.3 Hz), 7.05–7.11 (2H, m), 7.11 (1H, s), 7.15 (1H, d, J=8.8 Hz), 7.34 (1H, s), 7.45 (1H, d, J=8.5 Hz)

MASS: 603 (M+H)$^+$

Example 26

The following compounds were prepared by a similar manner to that of Example 25.

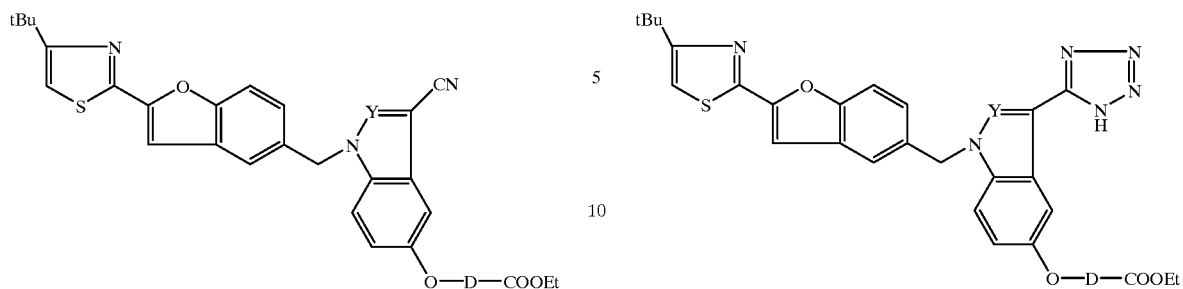

| Example | D | Y | Physical data |
|---|---|---|---|
| 26-1 | —C(Me)₂— | CH | IR(Nujol): 2200, 1720, 1250 cm⁻¹ NMR(CDCl₃, δ): 1.30(3H, t, J=7.1Hz), 1.40(9H, s), 1.51 (6H, s), 4.28(2H, q, J=7.1Hz), 5.38(2H, s), 6.95 (1H, dd, J=2.2, 9.0Hz), 7.00 (1H, s), 7.13(1H, dd, J=1.8, 8.5Hz), 7.21–7.28(3H, m), 7.40(1H, s), 7.52(1H, d, J=8.5Hz), 7.58(1H, s) MASS: 542(M + H)⁺ |
| 26-2 | —CH₂— | N | mp: 95–98° C. IR(Nujol): 2250, 1738, 1500 cm⁻¹ NMR(DMSO-d₆, δ): 1.35(9H, s), 1.22(3H, t, J=7.1Hz), 4.18 (2H, q, J=7.1Hz), 4.92(2H, s), 5.90(2H, 5), 7.29(1H, dd, J=2.3, 7.9Hz), 7.31(1H, s), 7.38(1H, dd, J=1.7, 8.6Hz), 7.48(1H, s), 7.52 (1H, 5), 7.67(1H, d, J=8.6Hz), 7.70(1H, s), 7.98 (1H, d, J=10.0Hz) MASS: 515(M + H)⁺ |

Example 27

A mixture of methyl 1-{[2-(4-tert-butylthiazol-2-yl) benzofuran-5-yl]methyl}-5-(4-ethoxycarbonylbutoxy) indole-3-acetate (0.2 g) and 1N-sodium hydroxide (1.66 ml) in a mixed solvent of tetrahydrofuran (2 ml) and methanol (1 ml) was stirred at room temperature for 4 hours. After removal of solvents, the aqueous solution was acidified with diluted hydrochloric acid. The resulting precipitates were collected by filtration and washed with water to give 1-{[2-(4-tert-butylthiazol-2-yl)benzofuran-5-yl]methyl}-5-(4-carboxybutoxy)indole-3-acetic acid (0.15 g).

IR (Nujol): 3300, 2700–2500, 1690, 1610 cm⁻¹

NMR (DMSO-d₆, δ): 1.34 (9H, s), 1.6–1.8 (4H, m), 2.28 (2H, t, J=6.7 Hz), 3.63 (2H, s), 3.9–3.95 (2H, m), 5.43 (2H, s), 6.75 (1H, dd, J=2.2, 8.8 Hz), 7.02 (1H, d, J=2.2 Hz), 7.26 (1H, dd, J=1.7, 8.5 Hz), 7.30 (1H, d, J=8.8 Hz), 7.34 (1H, s), 7.47 (1H, s), 7.49 (1H, s), 7.57 (1H, br s), 7.63 (1H, d, J=8.5 Hz), 12.0 (2H, br s)

MASS: 561 (M+H)⁺

Example 28

The following compounds were prepared by a similar manner to that of Example 27.

| Example | D | Y | Physical data |
|---|---|---|---|
| 28-1 | —C(Me)₂— | CH | mp: 206–215° C. IR(Nujol): 3600–2300, 1710, 1250 cm⁻¹ NMR(DMSO-d₆, δ): 1.35(9H, s), 1.51(6H, s), 5.63(2H, s), 6.90(1H, dd, J=2.3, 8.9Hz), 7.38(1H, d, J=8.5Hz), 7.47 (1H, s), 7.51(1H, s), 7.58 (1H, d, J=8.9Hz), 7.67(1H, s), 7.69(1H, d, J=8.5Hz), 7.79(1H, d, J=2.3Hz), 8.16 (1H, s) MASS: 557(M + H)⁺ |
| 28-2 | —CH₂C(Me)₂— | CH | mp: >230° C. IR(Nujol): 3400–3000, 1730, 3200–2300, 1260 cm⁻¹ NMR(DMSO-d₆, δ): 1.26(6H, s), 1.34(9H, s), 4.02(2H, s), 5.64(2H, s), 6.90(1H, dd, J=2.3, 9.0Hz), 7.35(1H, d, J=8.5Hz), 7.47(1H, s), 7.50 (1H, s), 7.57(1H, d, J=9.0Hz), 7.62–7.72(3H, m), 8.21(1H, s) MASS: 571(M + H)⁺ |
| 28-3 | —CH₂— | CH | mp: 228–230° C. IR(Nujol): 3350, 3100, 1790, 1765, 1630, 1600, 1490 cm⁻¹ NMR(DMSO-d₆, δ): 1.34(9H, s), 4.73(2H, s), 5.65(2H, s), 6.96(1H, dd, J=2.5, 9.0Hz), 7.36(1H, d, J=8.5Hz), 7.47 (1H, s), 7.51(1H, s), 7.60 (1H, d, J=9.0Hz), 7.65–7.74 (3H, m), 8.21(1H, s) |
| 28-4 | —CH₂— | N | mp: 180–185° C. (dec.) IR(Nujol): 3300, 2500–2700, 1720, 1620, 1590, 1500 cm⁻¹ NMR(DMSO-d₆, δ): 1.34(9H, s), 4.80(2H, s), 5.93(2H, s), 7.26(1H, dd, J=2.3, 9.1Hz), 7.30(1H, dd, J=1.9, 8.6Hz), 7.47(1H, s), 7.51(1H, s), 7.61(1H, d, J=2.3Hz), 7.61 (1H, s), 7.66(1H, d, J=8.6Hz), 7.88(1H, d, J=9.1Hz) MASS: 530(M + H)⁺ Elemental Analysis Calcd. for C₂₆H₂₃N₇O₄S.3H₂O: C 53.51, H 5.01, N 16.80 Found: C 53.49, H 4.56, N 16.54 |

Example 29

A mixture of methyl 1-{[2-(4-tert-butylthiazol-2-yl) benzofuran-5-yl]methyl}-5-hydroxyindole-3-acetate (0.474 g), benzyl 4-bromobutylate (0.34 g) and potassium carbonate (0.19 g) in N,N-dimethylformamide (5 ml) was stirred at 50° C. for 8 hours. After being cooled to room temperature, the mixture was poured into ice-water and extracted with ethyl acetate. The organic layer was washed with brine, dried over magnesium sulfate and concentrated under reduced pressure. The residue was subjected to column chromatography on silica gel and eluted with a mixture of n-hexane and ethyl acetate. The fractions containing the objective compound were combined and concentrated under reduced pressure to give methyl 5-[3-(benzyloxycarbonyl)propoxy]-1-{[2-(4-tert-butylthiazol-2-yl)benzofuran-5-yl]methyl}indole-3-acetate (0.36 g).

IR (Neat): 3100, 2950, 1725, 1615, 1575, 1480 cm$^{-1}$

NMR (CDCl$_3$, δ) 1.40 (9H, s), 2.08–2.21 (2H, m), 2.60 (2H, t, J=7.3 Hz), 3.70 (3H, s), 3.74 (2H, s), 4.05 (2H, t, J=6.0 Hz), 5.13 (2H, s), 5.32 (2H, s), 6.80 (1H, dd, J=2.3, 8.8 Hz), 6.96 (1H, s), 7.05 (1H, d, J=2.3 Hz), 7.05–7.11 (3H, m), 7.31–7.35 (7H, m), 7.45 (1H, d, J=8.5 Hz)

MASS: 651 (M+H)$^+$

Example 30

The following compounds were prepared by a similar manner to that of Example 29.

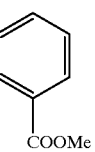

| Example | R$^9$ | R$^{12}$ | Physical data |
|---|---|---|---|
| 30-1 | —CH$_2$COOMe | —OCH$_2$COOBzl | IR(Neat): 1730, 1580, 1480 cm$^{-1}$<br>NMR(CDCl$_3$, δ): 1.40(9H, s), 3.69(3H, s), 3.70(2H, s), 4.71(2H, s), 5.25(2H, s), 5.33(2H, s), 6.90(1H, dd, J=0.5, 8.8Hz), 6.97(1H, s), 7.05-7.09(2H, m), 7.12(1H, s), 7.17(1H, d, J=8.9Hz), 7.24(1H, s), 7.29–7.36(6H, m), 7.46(1H, d, J=8.5Hz)<br>MASS: 623(M + H)$^+$ |
| 30-2 | —CN | —OCH$_2$CN | IR(Nujol): 2200, 1230 cm$^{-1}$<br>NMR(CDCl$_3$, δ): 1.40(9H, s), 4.83(2H, s), 5.41(2H, s), 7.00(1H, s), 7.01(1H, dd, J=8.9, 2.5Hz), 7.12(1H, dd, J=8.5, 1.9Hz), 7.18–7.34(3H, m), 7.39(1H, s), 7.52(1H, d, J=8.5Hz), 7.65(1H, s)<br>MASS: 466(M$^+$), 270 |
| 30-3 | —CN | —OCH$_2$COOMe | IR(Nujol): 2200, 1740, 1220 cm$^{-1}$<br>NMR(CDCl$_3$, δ): 1.40(9H, s), 4.70(3H, s), 5.39(3H, s), 7.00(1H, s), 7.02(1H, dd, J=2.4, 8.9Hz), 7.12(1H, dd, J=1.8, 8.4Hz), 7.14(1H, d, J=2.4Hz), 7.27(1H, s), 7.29 (1H, d, J=8.9Hz), 7.39(1H, d, J=1.8Hz), 7.52(1H, d, J=8.4Hz), 7.60(1H, s)<br>MASS: 499(M$^+$), 270 |
| 30-4 | —CH$_2$COOMe | —OCH$_2$-C$_6$H$_4$-COOMe (meta) | IR(Nujol): 1720, 1615, 1580, 1480, 1440, 1360 cm$^{-1}$<br>NMR(CDCl$_3$, δ): 1.41(9H, s), 3.69(3H, s), 3.74(2H, s), 5.15(2H, s), 5.34(2H, s), 6.92(1H, dd, J=2.5, 8.7Hz), 6.97–7.17(4H, m), 7.30(1H, s), 7.36(1H, s), 7.39–7.56 (3H, m), 7.68(1H, d, J=7.7Hz), 7.94–8.04(2H, m), 8.16(1H, s)<br>MASS: 623(M + H)$^+$ |

Example 31

A solution of methyl 5-[3-(benzyloxycarbonyl)propoxy]-1-{[2-(4-tert-butylthiazol-2-yl)benzofuran-5-yl]

methyl}indole-3-acetate in a mixed solvent of tetrahydrofuran (2 ml) and methanol (2 ml) was hydrogenated over 10% Pd—C (60 mg) at room temperature under atmosphere pressure. After removal of the catalyst by filtration, the filtrate was concentrated under reduced pressure to give methyl 1-{[2-(4-tert-butylthiazol-2-yl)benzofuran-5-yl]methyl}-5-(3-carboxypropoxy)indole-3-acetate (0.16 g).

IR (Nujol): 2700, 1725, 1715, 1490 cm$^{-1}$

NMR (CDCl$_3$, δ): 1.40 (9H, s), 2.13 (2H, quint, J=7.0 Hz), 2.61 (2H, t, J=7.0 Hz), 3.70 (3H, s), 3.74 (2H, s), 4.06 (2H, t, J=7.0 Hz), 5.31 (2H, s), 6.82 (1H, dd, J=2.2, 8.9 Hz), 6.97 (1H, s), 7.06–7.17 (4H, m), 7.29 (1H, s), 7.34 (1H, s), 7.45 (1H, d, J=8.5 Hz)

MASS: 561 (M+H)$^+$

Example 32

The following compound was prepared by a similar manner to that of Example 31.

Methyl 1-{[2-(4-tert-butylthiazol-2-yl)benzofuran-5-yl]methyl}-5-(carboxymethoxy)indole-3-acetate IR (Nujol): 1735, 1580, 1485 cm$^{-1}$ NMR (CDCl$_3$, δ): 1.40 (9H, s), 3.70 (3H, s), 3.74 (2H, s), 4.71 (2H, s), 4.8–5.0 (1H, br s), 5.33 (2H, s), 6.90 (1H, dd, J=2.4, 8.9 Hz), 6.97 (1H, s), 7.10–7.20 (4H, m), 7.30 (1H, s), 7.34 (1H, s), 7.45 (1H, d, J=8.5 Hz)

MASS: 533 (M+H)$^+$

Example 33

1-Ethyl-3-(3'-dimethylaminopropyl)carbodiimide (46.5 mg) was added to a mixture of methyl 1-{[2-(4-tert-butylthiazol-2-yl)benzofuran-5-yl]methyl}-5-(carboxymethoxy)indole-3-acetate (145 mg), dimethylamine hydrochloride (24.4 mg) and 1H-hydroxybenzotriazole hydrate (40.4 mg) in dichloromethane (2 ml) and then the mixture was stirred at room temperature for 2 hours. After removal of solvent, the residue was partitioned between aqueous sodium hydrogen carbonate solution and ethyl acetate. The organic layer was washed with brine, dried over magnesium sulfate and concentrated under reduced pressure. The residue was subjected to column chromatography on silica gel and eluted with a mixture of n-hexane and ethyl acetate. The fractions containing the objective compound were combined and concentrated under reduced pressure to give methyl 1-{[2-(4-tert-butylthiazol-2-yl)benzofuran-5-yl]methyl}-5-(N,N-dimethylcarbamoylmethoxy)-indole-3-acetate (0.16 g).

IR (Neat): 1730, 1650, 1575, 1480, 1340 cm$^{-1}$

NMR (CDCl$_3$, δ): 1.40 (9H, s), 2.89 (3H, s), 3.11 (3H, s), 3.72 (2H, s), 3.75 (2H, s), 4.72 (2H, s), 5.33 (2H, s), 6.90 (1H, dd, J=2.4, 9.0 Hz), 6.97 (1H, s), 7.08–7.25 (5H, m), 7.35 (1H, s), 7.46 (1H, d, J=8.5 Hz)

MASS: 560 (M+H)$^+$

Example 34

The following compounds were prepared by a similar manner to that of Example 33.

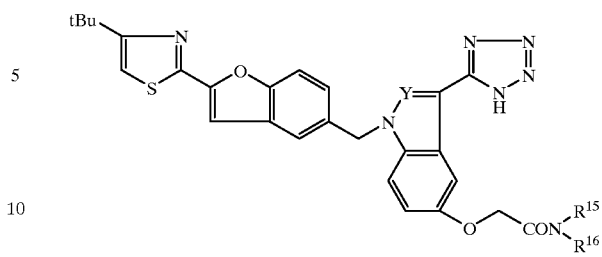

| Example | —N(R$^{15}$)(R$^{16}$) | Y | Physical data |
|---|---|---|---|
| 34-1 | amino | CH | mp: >200° C. (dec.)<br>IR(Nujol): 3500, 2300, 1670 cm$^{-1}$<br>NMR(DMSO-d$_6$, δ): 1.34(9H, s), 4.48(2H, s), 5.64(2H, s), 7.00(1H, dd, J=2.4, 8.9Hz), 7.36(1H, dd, J=1.7, 8.5Hz), 7.38(1H, br s), 7.47(1H, 5), 7.51(1H, s), 7.58(1H, br s), 7.62–7.65(2H, m), 7.68(1H, d, J=8.6Hz), 7.75 (1H, d, J=2.4Hz), 8.19(1H, s)<br>MASS: 528(M + H)$^+$ |
| 34-2 | methylamino | CH | mp: 179° C.(dec.)<br>IR(Nujol): 3500–3100, 1660 cm$^{-1}$<br>NMR(DMSO-d6, δ): 1.34(9H, s), 2.67(3H, d, J=4.6Hz), 4.52 (2H, s), 5.65(2H, s), 7.01 (1H, dd, J=2.4, 9.0Hz), 7.36 (1H, d, J=8.5Hz), 7.48(1H, s), 7.51(1H, s), 7.59–7.71 (3H, m), 7.77(1H, d, J=2.3Hz), 8.09(1H, br s), 8.21(1H, s)<br>MASS: 542(M + H)$^+$ |
| 34-3 | 1-pyrrolidinyl | CH | mp: >230° C.<br>IR(Nujol): 3500–2300, 1615, 1190 cm$^{-1}$<br>NMR(DMSO-d$_6$, δ): 1.34(9H, s), 1.75–2.00(4H, m), 3.55(2H, t, J=6.6Hz), 4.74(2H, s), 5.64 (2H, 3), 6.95(1H, dd, J=2.4Hz, 8.9Hz), 7.35(1H, dd, J=1.7, 8.5Hz), 7.47(1H, s), 7.51(1H, s), 7.58(1H, d, J=8.9Hz), 7.63–7.70(3H, m), 8.18(1H, s)<br>MASS: 582(M + H)$^+$ |
| 34-4 | piperidino- | CH | mp: >200° C.<br>IR(Nujol): 3200–2200, 1620, 1250 cm$^{-1}$<br>NMR(DMSO-d$_6$, δ): 1.34(9H, s), 1.45(2H, br s), 1.62(4H, br s), 3.44(4H, br s), 4.82 (2H, s), 5.64(2H, s), 6.95 (1H, dd, J=2.4, 8.9Hz), 7.35 (1H, dd, J=1.7, 8.5Hz), 7.47 (1H, s), 7.51(1H, s), 7.58 (1H, d, J=8.9Hz), 7.63–7.70 (3H, m), 8.19(1H, s)<br>MASS: 596(M + H)$^+$ |
| 34-5 | morpholino- | CH | mp: >230° C.<br>IR(Nujol): 3500–2500, 1620, 1250 cm$^{-1}$<br>NMR(DMSO-d$_6$, δ): 1.34(9H, s), 3.30–3.80(4H, br s), 4.86 (2H, s), 5.64(2H, s), 6.96 (1H, dd, J=2.4, 8.9Hz), 7.36 (1H, dd, J=1.8, 8.5Hz), 7.34 (1H, s), 7.38(1H, s), 7.47–7.71(4H, m), 8.18(1H, s)<br>MASS: 598(M + H)$^+$ |

-continued

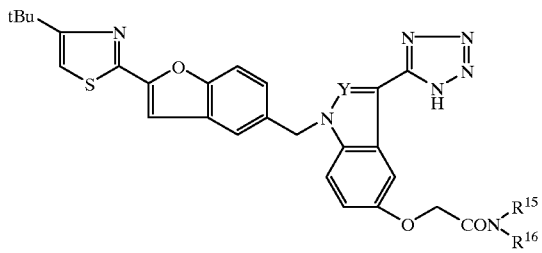

| Example | —N(R15)(R16) | Y | Physical data |
|---|---|---|---|
| 34-6 | 4-thio-morpholinyl | CH | mp: >230° C.<br>IR(Nujol): 3500–2500, 1620 cm⁻¹<br>NMR(DMSO-d₆, δ): 1.34(9H, s), 2.73(2H, s), 2.89(2H, s), 3.74(4H, s), 4.85(2H, s), 5.65(2H, s), 6.96(1H, dd, J=2.4, 8.9Hz), 7.36(1H, dd, J=1.7, 8.9Hz), 7.48(1H, s), 7.51(1H, s), 7.57–7.71(4H, m), 8.20(1H, s)<br>MASS: 614(N + H)⁺ |
| 34-7 | 4-methyl-piperazin-1-yl | CH | mp: 232° C. (dec.)<br>IR(Nujol): 3600–2300, 1620, 1250 cm⁻¹<br>NMR(DMSO-d₆, δ): 1.34(9H, s), 2.26(3H, s), 2.35(4H, br s), 3.50(4H, br s), 4.84 (2H, s), 5.62(2H, s), 6.92 (1H, dd, J=2.4, 8.9Hz), 7.34 (1H, dd, J=1.7, 8.5Hz), 7.47 (1H, s), 7.50 (1H, s), 7.55 (1H, d, J=8.9Hz), 7.62–7.72 (3H, m), 8.16(1H, s)<br>MASS: 611(M + H)⁺ |
| 34-8 | 4-cyclohexyl piperazin-1-yl | CH | mp: 206.7° C. (dec.)<br>IR(Nujol): 3500–2300, 1620, 1250 cm⁻¹<br>NMR(DMSO-d₆, δ): 1.18(6H, br 5), 1.34(9H, s), 1.59(1H, br s), 1.73(4H, br s), 2.50 (2H, br s), 2.62(2H, br s), 3.48(4H, br s), 4.83(2H, s), 5.63(2H, s), 6.94(1H, dd, J=2.4, 8.9Hz), 7.35(1H, dd, J=1.7, 8.5Hz), 7.46(1H, s), 7.50(1H, s), 7.57(1H, d, J=8.9Hz), 7.63–7.71(3H, m), 8.17(1H, s)<br>MASS: 679(M + H)⁺ |
| 34-9 | 4-methyl piperazin-1-yl amino | CH | mp: 179.1° C. (dec.)<br>IR(Nujol): 3650–2500, 1660, 1270 cm⁻¹<br>NMR(DMSO-d₆, δ): 1.34(9H, s), 2.24(3H, s), 2.85(4H, br s), 3.47(4H, br s), 4.47 and 4.91(2H, s × 2), 5.62(2H, s), 6.98(1H, m), 7.35(1H, d, J=8.5Hz), 7.47(1H, s), 7.50(1H, s), 7.51–7.75(4H, m), 8.16(1H, d, J=8.5Hz), 8.82 and 9.24(1H, br s × 2)<br>MASS: 626(M + H)⁺ |
| 34-10 | amino | N | mp: >250° C.<br>IR(Nujol): 3450, 3200(br), 2500–2700, 1660, 1590, 1500 cm⁻¹<br>NMR(DMSO-d₆, δ): 1.34(9H, s), 4.53(2H, s), 5.89(2H, s), 7.26(1H, dd, J=2.4, 9.1Hz), 7.35(1H, d, J=8.9Hz), 7.42 (1H, br s), 7.46(1H, s), |

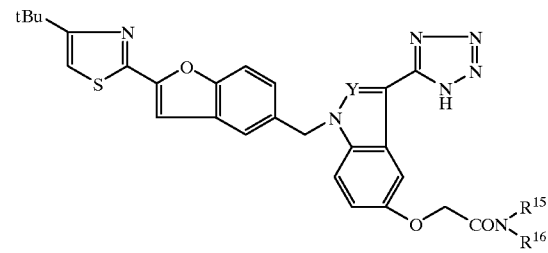

| Example | —N(R15)(R16) | Y | Physical data |
|---|---|---|---|
| | | | 7.50(1H, s), 7.64(2H, s), 7.64–7.71(2H, m), 7.84(1H, d, J=9.1Hz)<br>MASS: 529(M + H)⁺, 504 |
| 34-11 | methylamino | N | mp: 180–190° C. (dec.)<br>IR(Nujol): 3300, 2500–2700, 1650, 1600, 1500 cm⁻¹<br>NMR(DMSO-d₆, δ): 2.68(3H, d, J=4.7Hz), 4.58(2H, s), 5.93 (2H, s), 7.31(1H, dd, J=2.4, 9.1Hz), 7.30–7.35(1H, m), 7.47(1H, s), 7.51(1H, s), 7.65(1H, s), 7.68(1H, m), 7.69(1H, br s), 7.90(1H, d, J=9.1Hz), 8.05–8.15(1H, m)<br>MASS: 543(M + H)⁺<br>Elemental Analysis Calcd. for C₂₇H₂₆N₈O₃S.1/2H₂O:<br>C 58.79, H 4.93, N 20.31<br>Found: C 58.73, H 5.08, N 19.36 |
| 34-12 | dimethylamino | N | mp: 152–164° C. (dec.)<br>IR(Nujol): 3300, 2500–2700, 1630, 1600, 1500 cm⁻¹<br>NMR(DMSO-d₆, δ): 1.34(9H, s), 2.87(3H, s), 3.06(3H, s), 4.93(2H, s), 5.93(2H, s), 7.26(1H, dd, J=2.3, 9.1Hz), 7.36(1H, d, J=8.5Hz), 7.47 (1H, s), 7.51(1H, s), 7.60–7.70(3H, m), 7.87(1H, d, J=9.1Hz)<br>MASS: 557(M + H)⁺ |
| 34-13 | 4-thio morpholinyl | N | IR(Nujol): 3300, 2500–2700, 1620, 1500 cm⁻¹<br>NMR(DMSO-d₆, δ): 1.34(9H, s), 2.5–2.80(4H, m), 2.70–2.80 (4H, m), 4.96(2H, s), 5.93 (2H, s), 7.27(1H, dd, J=2.3, 9.1Hz), 7.36(1H, dd, J=1.9, 8.6Hz), 7.47(1H, s), 7.51 (1H, s), 7.60–7.70(3H, s), 7.88(1H, d, J=9.1Hz)<br>MASS: 615, 616 |

Example 35

Methansulfonyl chloride (0.13 ml) was added to the solution of methyl 3-hydroxy-2,2-dimethylpropionate (0.13 g) and triethylamine (0.28 ml) in dichloromethane over 20 minutes at −40° C. After 1 hour, the reaction mixture was allowed to warm to room temperature and concentrated under reduced pressure. The residue was partitioned between aqueous sodium hydrogen carbonate solution and ethyl acetate, and the ethyl acetate layer was washed with brine, dried over magnesium sulfate and evaporated under reduced pressure to give the corresponding mesylate (0.21 g). A mixture of 1-{[2-(4-tert-butylthiazol-2-yl]benzofuran-5-yl]methyl}-5-hydroxyindole-3-carbonitrile (0.35 g), the mesylate (0.21 g) and potassium carbonate (0.23 g) in N,N-dimethylformamide (5 ml) was stirred at 100° C. for 20 hours. After cooling, the reaction mixture was poured into water and made acidic with diluted hydrochloric acid. The resulting precipitates were collected by filtration and washed with water and subjected to column chromatography on silica gel and eluted with a mixture of ethyl acetate and toluene. The fractions containing the objective compounds were combined and concentrated under reduced pressure to give 1-{[2-(4-tert-butylthiazol-2-yl)benzofuran-5-yl]methyl}-5-(2-methoxycarbonyl-2-methylpropoxy)indole-3-carbonitrile (0.18 g).

IR (Nujol): 2200, 1725 cm$^{-1}$

NMR (CDCl$_3$, δ): 1.34 (6H, s), 1.40 (9H, s), 3.70 (3H, s), 4.02 (2H, s), 5.39 (2H, s), 6.91 (1H, d, J=9.0 Hz), 6.99 (1H, s), 7.10 (1H, d, J=8.5 Hz), 7.18–7.26 (3H, m), 7.37 (1H, s), 7.51 (1H, d, J=8.5 Hz), 7.59 (1H, s)

MASS: 542 (M+H)$^+$

Example 36

Trifluoroacetic acid (10 ml) was added to a mixture of 4-tert-butyl-2-{5-[(3-cyano-5-benzyloxyindol-1-yl)methyl]benzofuran-2-yl}thiazole (0.54 g), m-cresol (0.28 ml), thioanisole (0.28 ml) and ethanedithiol (0.56 ml) under ice-cooling. After being stirred for 4 hours, the mixture was poured into water (100 ml) and the resulting mixture was neutralized with aqueous sodium hydrogen carbonate solution and extracted with ethyl acetate. The organic layer was washed with water, brine successively, dried over magnesium sulfate and concentrated under reduced pressure. The resulting residue was subjected to column chromatography on silica gel and eluted with a mixture of toluene and ethyl acetate. The fractions containing the objective compound were combined and concentrated under reduced pressure to give 4-tert-butyl-2-{5-[(3-cyano-5-hydroxyindol-1-yl)methyl]benzofuran-2-yl}thiazole (305 mg).

IR (Nujol): 3350–2800, 2200 cm$^{-1}$

NMR (DMSO-d$_6$, δ): 1.35 (9H, s), 5.54 (2H, s), 6.78 (1H, dd, J=2.2, 8.9 Hz), 6.92 (1H, d, J=2.2 Hz), 7.36 (1H, dd, J=1.8, 8.5 Hz), 7.47 (1H, s), 7.48 (1H, d, J=8.5 Hz), 7.50 (1H, s), 7.65 (1H, s), 7.66 (1H, d, J=8.9 Hz), 8.37 (1H, s), 9.32 (1H, br s)

MASS: 428 (M+H)$^+$

Example 37

A mixture of 4-tert-butyl-2-{5-[(3-cyano-5-hydroxyindol-1-yl)methyl]benzofuran-2-yl}thiazole (158 mg), methyl iodide (0.1 ml) and sodium carbonate (0.1 g) in N,N-dimethylformamide (1.5 ml) was stirred for 3 days at room temperature. The resulting mixture was diluted with brine and extracted with ethyl acetate. The organic layer was washed with brine, dried over magnesium sulfate and concentrated under reduced pressure to give 4-tert-butyl-2-{5-[(3-cyano-5-methoxyindol-1-yl)methyl]benzofuran-2-yl}thiazole.

IR (Neat): 2230, 1620, 1530, 1490, 1460, 1380, 1230 cm$^{-1}$

NMR (CDCl$_3$, δ): 1.40 (9H, s), 3.87 (3H, s), 5.39 (2H, s), 6.93 (1H, dd, J=2.4, 9.0 Hz), 6.99 (1H, s), 7.12 (1H, dd, J=1.9, 8.5 Hz), 7.19 (1H, d, J=2.4 Hz), 7.25 (1H, d, J=9.0 Hz), 7.26 (1H, br s), 7.39 (1H, d, J=1.9 Hz), 7.51 (1H, d, J=8.5 Hz), 7.59 (1H, s)

MASS: 441 (M$^+$), 270, 255

Example 38

The following compound was prepared by a similar manner to that of Example 37.

1-{[2-(4-tert-Butylthiazol-2-yl)benzofuran-5-yl]methyl}-5-methoxyindazole-3-carbonitrile mp: 100–102° C.

IR (Nujol): 2210, 1500 cm$^{-1}$

NMR (DMSO-d$_6$, δ): 1.35 (9H, s), 3.85 (3H, s), 5.89 (2H, s), 7.20–7.26 (2H, m), 7.38 (1H, dd, J=1.9, 8.6 Hz), 7.48 (1H, s), 7.52 (1H, s), 7.67 (1H, s, J=8.6 Hz), 7.70 (1H, s), 7.95 (1H, d, J=9.5 Hz)

MASS: 443 (M+H)$^+$

Example 39

A mixture of 5-{1-{[2-(4-tert-butylthiazol-2-yl)benzofuran-5-yl]methyl}-5-(carboxymethoxy)indol-3-yl}-1H-tetrazole (60 mg) and 1,1'-carbonyldiimidazole (60 mg) in dichloromethane (2 ml) was stirred at room temperature for 5 hours. And then, dimethylamine hydrochloride (16.5 mg) and triethylamine (0.5 ml) were added to the mixture successively. After being stirred for 18 hours, the mixture was concentrated under reduced pressure. The resulting residue was acidified with diluted hydrochloric acid and the resulting mixture was extracted with ethyl acetate. The extract was washed with brine, dried over magnesium sulfate and concentrated under reduced pressure. The residue was subjected to column chromatography on silica gel and eluted with a mixture of chloroform, ethyl acetate and methanol. The fractions containing the objective compound were combined and concentrated under reduced pressure to give 5-{1-{[2-(4-tert-butylthiazol-2-yl)benzofuran-5-yl]methyl}-5-(N,N-dimethylcarbamoylmethoxy)indol-3-yl}-1H-tetrazole (30.1 mg).

mp: 258° C. (dec.)

IR (Nujol): 3100, 2700–2500, 1630, 1620, 1500, 1490, 1390, 1345, 1320, 1300, 1260, 1240, 1210 cm$^{-1}$ NMR (DMSO-d$_6$, δ): 1.34 (9H, s), 2.86 (3H, s), 3.05 (3H, s), 4.82 (2H, s), 5.64 (2H, s), 6.96 (1H, dd, J=2.6, 9.0 Hz), 7.36 (1H, d, J=8.5 Hz), 7.47 (1H, s), 7.51 (1H, s), 7.59 (1H, d, J=9.0 Hz), 7.64–7.70 (3H, m), 8.20 (1H, s)

Example 40

The following compounds were prepared by a similar manner to that of Example 39.

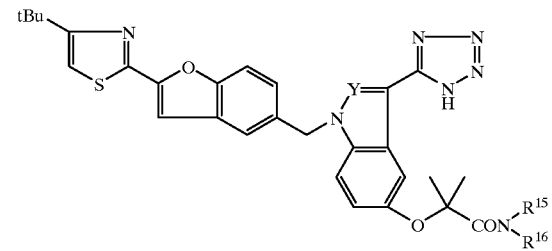

| Example | —N⟨R$^{15}$/R$^{16}$ | Physical data |
|---|---|---|
| 40-1 | amino | mp: 181–186° C. (dec.)<br>IR(Nujol): 3500, 3300, 1670, 1630, 1600, 1510, 1260, 1220 cm$^{-1}$<br>NMR(DMSO-d$_6$, δ): 1.34(9H, s), 1.41(6H, s), 5.64(2H, s), 6.97(1H, dd, J=2.3, 8.9Hz), 7.30(1H, br s), 7.38(1H, |

-continued

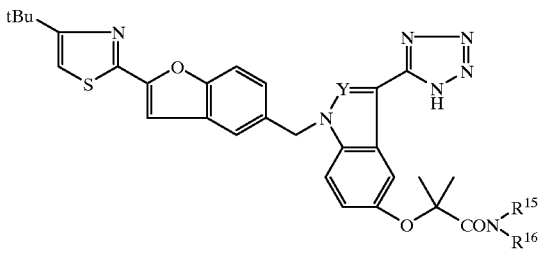

| Example | —N(R15)(R16) | Physical data |
|---|---|---|
| 40-2 | methylamino | dd, J=1.7, 8.5Hz), 7.47(1H, s), 7.52(1H, s), 7.56(1H, br s), 7.61(1H, d, J=8.9Hz), 7.68(1H, s), 7.70(1H, d, J=8.5Hz), 7.84(1H, d, J=2.3Hz), 8.19(1H, s) MASS: 556(M + H)+, 309 mp: 227° C. (dec.) IR(Nujol): 3400, 2500–2700, 1640, 1630, 1610, 1550, 1480, 1460, 1410, 1380 cm−1 NMR(DMSO-d6, δ): 1.35(9H, s), 1.39(6H, s), 2.69(3H, d, J=4.8Hz), 5.42(2H, s), 6.94 (1H, dd, J=2.3, 8.9Hz), 7.39 (1H, dd, J=1.7, 8.5Hz), 7.48 (1H, s), 7.52(1H, s), 7.61 (1H, d, J=8.9Hz), 7.68(1H, s), 7.70(1H, d, J=8.5Hz), 7.84(1H, d, J=2.3Hz), 8.13 (1H, d, J=4.8Hz), 8.20(1H, s) MASS: 570(M + H)+, 309 |
| 40-3 | dimethylamino | IR(Nujol): 3300, 2500–2700, 1630, 1600, 1150, 1120 cm−1 NMR(CDCl3, δ): 1.39(9H, s), 1.61(6H, s), 3.06(3H, s), 3.06(3H, s), 5.27(2H, s), 6.82(1H, dd, J=2.3, 8.9Hz), 6.97(1H, s), 7.07(1H, dd, J=1.7, 0.7Hz), 7.14(1H, d, J=8.7Hz), 7.18(1H, d, J=8.9Hz), 7.27–7.36(2H, m), 7.80(1H, d, J=2.3Hz), 7.96 (1H, s) MASS: 584(M + H)+ |

Example 41

A mixture of 5-{1-{[2-(4-tert-butylthiazol-2--yl)benzofuran-5-yl]methyl}-5-(carboxymethoxy)indol-3-yl}-1H-tetrazole (112.4 mg), 2-methylphenylsulfonamide (43.7 mg), 1-ethyl-3-(31-dimethylaminopropyl)carbodiimide hydrochloride (61.4 mg) and dimethylaminopyridine (50.0 mg) in N,N-dimethylformamide (1.5 ml) was stirred at room temperature for 3 days. The resulting mixture was poured into water and acidified with diluted hydrochloric acid. The resulting precipitates were collected by filtration and washed with water and then dissolved into aqueous sodium hydroxide solution. The resulting solution was acidified with diluted hydrochloric acid and the resulting precipitates were collected by filtration and washed with water to give 5-{1-{[2-(4-tert-butylthiazol-2-yl)benzofuran-5-yl]methyl}-5-[N-(2-methylphenylsulfonyl)carbamoylmethoxy]indol-3-yl}-1H-tetrazole (135.7 mg).

mp: 156–166° C.

IR (Nujol): 3500–3000, 2500–2700, 1730, 1630, 1605, 1480, 1460, 1380, 1350, 1200, 1160, 1130 cm−1

NMR (DMSO-d6, δ): 1.34 (9H, s), 2.57 (3H, s), 4.74 (2H, s), 5.64 (2H, s), 6.89 (1H, dd, J=9.0, 2.4 Hz), 7.27–7.34 (3H, m), 7.46–7.70 (8H, m), 7.95 (1H, d, J=6.8 Hz), 8.20 (1H, s)

MASS: 682 (M+H)+, 270

Example 42

A mixture of 4-tert-butyl-2-[5-(chloromethyl)benzofuran-2-yl]thiazole (0.36 g), benzyl indazole-3-carboxylate (0.30 g) and potassium carbonate (0.33 g) in methylethylketone (20 ml) was stirred under reflux for 7 hours. After being cooled to room temperature, the mixture was filtered and the filtrate was concentrated under reduced pressure. The syrup was subjected to column chromatography on silica gel and eluted with a mixture of n-hexane and ethyl acetate. The fractions containing the objective compounds were combined and concentrated under reduced pressure to give benzyl 1-{[2-(4-tert-butylthiazol-2-yl)benzofuran-5-yl]methyl}-1H-indazole-3-carboxylate (0.40 g) and benzyl 2-{[2-(4-tert-butylthiazol-2-yl)benzofuran-5-yl]methyl}-2H-indazole-3-carboxylate (0.12 g).

Benzyl 1-{[2-(4-tert-butylthiazol-2-yl)benzofuran-5-yl]methyl-}-1H-indazole-3-carboxylate IR (Neat): 1710, 1610, 1585, 1500, 1475 cm−1

NMR (CDCl3, δ): 1.40 (9H, s), 5.34 (2H, s), 5.80 (2H, s), 6.96 (1H, s), 7.20–7.56 (12H, m), 8.18 (1H, d, J=8.0 Hz)

MASS: 522 (M+H)+

Benzyl 2-{[2-(4-tert-butylthiazol-2-yl)benzofuran-5-yl]methyl}-2H-indazole-3-carboxylate IR (Neat): 1700, 1585, 1500, 1475 cm−1

NMR (CDCl3, δ): 1.40 (9H, s), 5.45 (2H, s), 6.20 (2H, s), 6.96 (1H, s), 7.21–7.46 (10H, m), 7.59 (1H, s), 7.83 (1H, d, J—8.5 Hz), 7.98 (1H, d, J=8.1 Hz)

MASS: 522 (M+H)+

Example 43

The following compounds were prepared by a similar manner to that of Example 42.

1) Isopropyl 5-benzyloxy-1-{[2-(4-tert-butylthiazol-2-yl)benzofuran-5-yl]methyl}-1H-indazole-3-carboxylate IR (Neat): 1700, 1490 cm−1

NMR (CDCl3, δ): 1.40 (9H, s), 1.47 (2H, d, J=6.3 Hz), 5.13 (2H, s), 5.42 (1H, hept, J=6.3 Hz), 5.76 (2H, s), 6.97 (1H, s), 7.08 (1H, dd, J=2.4, 8.9 Hz), 7.18–7.48 (10H, m), 7.66 (1H, d, J=2.0 Hz)

MASS: 580 (M+H)+

2) Methyl 1-{[2-(4-tert-butylthiazol-2-yl)benzofuran-5-yl]methyl}-5-isopropyl-1H-indazole-3-carboxylate mp: 126.2–127.4° C.

IR (Nujol): 1710 cm−1

NMR (CDCl3, δ): 1.30 (6H, d, J=6.9 Hz), 1.39 (7H, s), 3.06 (1H, hept, J=6.9 Hz), 4.06 (3H, s), 5.77 (2H, s), 6.97 (1H, s), 7.21–7.29 (4H, m), 7.46 (1H, d, J=8.4 Hz), 7.49 (1H, s), 8.07 (1H, s)

MASS: 488 (M+H)+

Example 44

A mixture of benzyl 1-{[2-(4-tert-butylthiazol-2-yl)benzofuran-5-yl]methyl}-1H-indazole-3-carboxylate (0.35 g), sodium methoxide (0.1 g) and formamide (4 ml) in tetrahydrofuran (2 ml) was stirred at 100° C. for 2 hours. After being cooled to room temperature, the mixture was concentrated under reduced pressure. Water was added to the residue and the resulting precipitates were collected by filtration and washed with a mixture of n-hexane and diisopropyl ether to give 1-{[2-(4-tert-butylthiazol-2-yl)benzofuran-5-yl]methyl}-1H-indazole-3-carboxamide. (0.22 g).

IR (Nujol): 3450, 3250, 3150, 3100, 1670, 1600, 1500, 1495 cm$^{-1}$

NMR (DMSO-d$_6$, δ): 1.34 (9H, s), 5.85 (2H, s), 7.20–7.50 (6H, m), 7.63–7.75 (3H, m), 7.83 (1H, d, J=8.5 Hz), 8.10 (1H, d, J=8.1 Hz)

MASS: 431 (M+H)$^+$

Example 45

The following compounds were prepared by a similar manner to that of Example 44.

1) 5-Benzyloxy-1-{[2-(4-tert-butylthiazol-2-yl)benzofuran-5-yl]methyl}-1H-indazole-3-carboxamide mp: 152–155° C.

IR (Nujol): 3450, 3150, 1670, 1590, 1480 cm$^{-1}$

NMR (DMSO-d$_6$, δ) 1.34 (9H, s), 5.14 (2H, s), 5.81 (2H, s), 7.18 (1H, dd, J=2.3, 9.1 Hz), 7.30–7.50 (10H, m), 7.60–7.70 (3H, m), 7.75 (1H, d, J=9.1 Hz)

MASS: 537 (M+H)$^+$ 2) 1-{[2-(4-tert-Butylthiazol-2-yl)benzofuran-5-yl]methyl}-5-isopropyl-1H-indazole-3-carboxamide mp: 123.3–130.0° C.

IR (Nujol): 3500–2500, 1670 cm$^{-1}$

NMR (DMSO-d$_6$, δ): 1.24 (6H, d, J=6.9 Hz), 1.34 (9H, s), 3.03 (1H, hept, J=6.9 Hz), 5.81 (2H, s), 7.33–7.39 (3H, m), 7.47 (1H, s), 7.50 (1H, s), 7.63–7.76 (4H, m), 8.01 (1H, s)

MASS: 473 (M+H)$^+$ 3) 2-{[2-(4-tert-butylthiazol-2-yl)benzofuran-5-yl]methyl}-2H-indazole-3-carboxamide mp: 201–202° C.

IR (Nujol): 3450, 3100, 1680, 1605, 1500, 1460, 1380, 1350 cm$^{-1}$

NMR (DMSO-d$_6$, δ): 1.33 (9H, s), 6.07 (2H, s), 7.18–7.40 (3H, m), 7.47 (1H, s), 7.51 (1H, s), 7.63–7.77 (3H, m), 7.86 (1H, d, J=9.0 Hz), 8.00 (2H, br s)

MASS: 431 (M+H)$^+$

Example 46

5-Benzyloxy-1-{[2-(4-tert-butylthiazol-2-yl)benzofuran-5-yl]methyl}-1H-indazole-3-carboxamide (0.122 g) was added to a solution (1 M) of borontribromide in dichloromethane (0.57 ml) under ice-cooling and then the mixture was stirred at room temperature for 1.5 hours. The mixture was concentrated under reduced pressure and the residue was partitioned between aqueous sodium hydrogen carbonate solution and ethyl acetate. The organic layer was separated, dried over magnesium sulfate and concentrated under reduced pressure to give 1-{[2-(4-tert-butylthiazol-2-yl)benzofuran-5-yl]methyl}-5-hydroxy-1H-indazole-3-carboxamide (0.08 g).

mp: 221–223° C.

IR (Nujol): 3300, 3150, 1655, 1610, 1600 cm$^{-1}$

NMR (DMSO-d$_6$, δ): 1.34 (9H, s), 5.76 (2H, s), 6.95 (1H, dd, J=2.3, 9.2 Hz), 7.29 (1H, br s), 7.34 (1H, dd, J=1.7, 8.6 Hz), 7.47 (1H, s), 7.51 (1H, s), 7.49 (1H, d, J=2.3 Hz), 7.60–7.68 (4H, m), 9.40 (1H, s)

MASS: 447 (M+H)$^+$

Example 47

The following compounds were prepared by a similar manner to that of Example 17.

1) Ethyl 2-methyl-1-{[2-(4-tert-butylthiazol-2-yl)benzofuran-5-yl]methyl}indole-3-carboxylate IR (Nujol): 1690, 1545, 1500 cm$^{-1}$ NMR (CDCl$_3$, δ): 1.39 (9H, s), 1.47 (3H, t, J=7.1 Hz), 2.76 (3H, s), 4.43 (2H, q, J=7.1 Hz), 5.45 (2H, s), 6.96 (1H, s), 7.00 (1H, dd, J=2.0, 6.5 Hz), 7.17–7.31 (5H, m), 7.45 (1H, d, J=8.4 Hz), 8.17–8.21 (1H, m)

MASS: 472 (M$^+$), 270 (base)

2) Methyl 1-{[2-(4-tert-butylthiazol-2-yl)benzofuran-5-yl]methyl}indole-3-carboxylate IR (Neat): 1690, 1530, 1500 cm$^{-1}$ NMR (CDCl$_3$, δ): 1.40 (9H, s), 3.91 (3H, s), 5.41 (2H, s), 6.96 (1H, s), 7.14 (1H, dd, J=1.9, 8.5 Hz), 7.20 (1H, d, J=7.2 Hz), 7.24–7.39 (5H, m), 7.48 (1H, d, J=8.5 Hz), 7.86 (1H, s), 8.18–8.24 (1H, m)

MASS: 444 (M$^+$), 367, 327, 312, 270

3) Methyl 2-{1-{[2-(4-tert-butylthiazol-2-yl)benzofuran-5-yl]methyl}indol-3-yl}-2-methylpropionate IR (Neat): 3100, 1730, 1610, 1590 cm$^{-1}$ NMR (CDCl$_3$, δ): 1.40 (9H, s), 1.69 (6H, s), 3.65 (3H, s), 5.37 (2H, s), 6.97 (1H, s), 7.02 (1H, s), 7.08–7.20 (3H, m), 7.27–7.30 (2H, m), 7.36 (1H, d, J=1.0 Hz), 7.48 (1H, d, J=8.5 Hz), 7.65–7.69 (1H, m)

MASS: 486 (M$^+$), 427, 270 (base)

Example 48

The following compounds were prepared by a similar manner to that of Example 18.

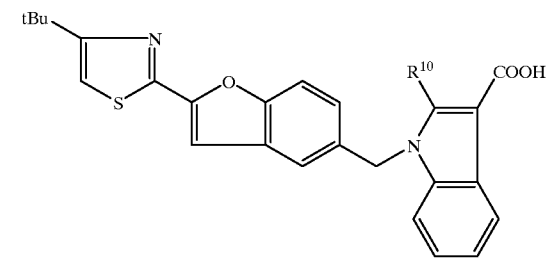

| Example | R$^{10}$ | Physical data |
|---|---|---|
| 48-1 | Me | mp: 227–229° C. (dec.) |
| | | IR(Nujol): 3110, 2600, 1650, 1535 cm$^{-1}$ |
| | | NMR(CDCl$_3$, δ): 1.39(9H, s), 2.81(3H, s), 5.47(2H, s), 6.94(1H, s), 7.02(1H, dd, J=2.0, 8.5Hz), 7.18–7.33(5H, m), 7.46(1H, d, J=8.5Hz), 8.3–8.34(1H, m) |
| | | MASS: 444(M$^+$), 270(base) |
| 48-2 | H | mp: 230–235° C. (dec.) |
| | | IR(Nujol): 2600, 1695, 1665, 1540, 1500 cm$^{-1}$ |
| | | NMR(DMSO-d6, δ): 1.34(9H, s), 5.62(2H, s), 7.18–7.22(2H, m), 7.39(1H, d, J=10.0Hz), 7.46(1H, s), 7.50(1H, s), 7.58–7.69(3H, m), 8.02–8.06(1H, m), 8.30(1H, s), 12.08(1H, br s) |
| | | MASS: 430(M$^+$), 386, 270(base) |

Example 49

The following compounds were prepared by a similar manner to that of Example 19.

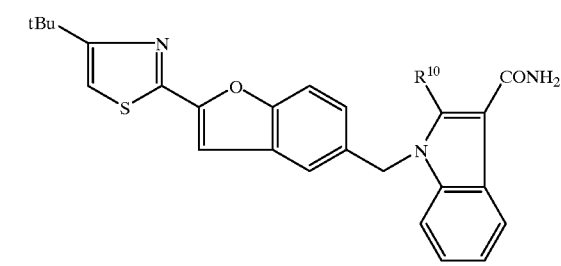

| Example | R¹⁰ | Physical data |
|---|---|---|
| 49-1 | Me | mp: 251–253° C. (dec.)<br>IR(Nujol): 3400, 3180, 1630, 1605, 1550, 1500 cm⁻¹<br>NMR(DMSO-d₆, δ): 1.34(9H, s), 2.64(3H, s), 5.59(2H, s), 7.0–7.15(4H, m), 7.36(1H, br s), 7.45–7.62(4H, m), 7.64(1H, d, J=8.6Hz), 7.82–7.87(1H, m)<br>MASS: 443(M⁺), 425, 270(base) |
| 49-2 | H | mp: 144–145° C.<br>IR(Nujol): 3400, 3200, 1640, 1610, 1530 cm⁻¹<br>NMR(DMSO-d₆, δ): 1.34(9H, s), 5.56(2H, s), 7.08–7.21(2H, m), 7.32(1H, dd, J=1.8, 8.5Hz), 7.47(1H, s), 7.50(1H, d, J=0.7Hz), 7.56–7.66(2H, m), 7.67 (1H, d, J=8.5Hz), 8.14–8.19(1H, m), 8.17(1H, s)<br>MASS: 429(M⁺), 411, 270(base) |

Example 50

The following compounds were prepared by a similar manner to that of Example 20.

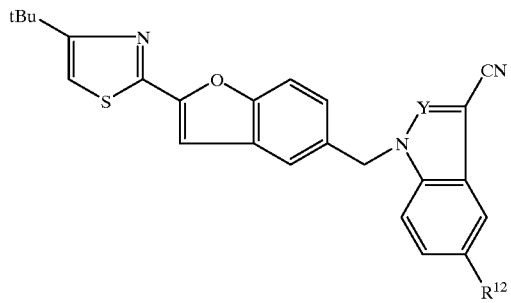

| Example | R¹² | Y | Physical data |
|---|---|---|---|
| 50-1 | H | C—Me | mp: 214–215° C.<br>IR(Nujol): 3110, 2230, 1590, 1520 cm⁻¹<br>NMR(CDCl₃, δ): 1.39(9H, s), 2.57 (3H, s), 5.42(2H, s), 6.98(1H, s), 7.00(1H, dd, J=2.0, 8.5Hz), 7.18–7.34(5H, m), 7.47(1H, d, J=8.5Hz) 7.7–7.74(1H, m)<br>MASS: 425(M⁺), 270 |
| 50-2 | H | CH | mp: 166–167° C.<br>IR(Nujol): 3130, 2230, 1535, 1500 cm⁻¹<br>NMR(CDCl₃, δ): 1.40(9H, s), 5.43 (2H, s), 6.99(1H, s), 7.13(1H, dd, J=1.8, 8.5Hz) 7.27(1H, s), 7.25–7.42(4H, m), 7.51(1H, d, J=8.5Hz), 7.64(1H, s), 7.75–7.81 (1H, m)<br>MASS: 411(M⁺), 367, 327, 312, 270 |
| 50-3 | H | N | IR(Nujol): 2230, 1500 cm⁻¹<br>NMR(CDCl₃, δ): 1.40(9H, s), 5.74 (2H, s), 6.98(1H, s), 7.20–7.51 (7H, m), 7.85(1H, d, J=8.0Hz)<br>MASS: 413(M + H)⁺ |
| 50-4 | OH | N | mp: 249–250° C.<br>IR(Nujol): 3100(br), 2210, 1570, 1480 cm⁻¹<br>NMR(DMSO-d₆, δ): 1.35(9H, s), 5.85 (2H, s), 7.01(1H, d, J=1.9Hz), 7.12(1H, dd, J=2.2, 9.1Hz), 7.38 (1H, dd, J=1.9, 8.5Hz), 7.47(1H, s), 7.51(1H, d, J=8.5Hz), 7.68(1H, d, J=8.5Hz), 7.70(1H, d, J=2.2Hz), 7.86(1H, d, J=9.1Hz), 9.90(1H, s)<br>MASS: 429(M + H)⁺ |
| 50-5 | iPr | N | mp: 164.5–165.5° C.<br>IR(Nujol): 2225 cm⁻¹<br>NMR(DMSO-d₆, δ): 1.26(6H, d, J=6.9Hz), 1.34(9H, s), 3.08(1H, hept, J=6.9Hz), 5.91(2H, s), 7.39 (1H, dd, J=1.7, 8.6Hz), 7.48(1H, s), 7.51–7.55(2H, m), 7.65–7.71 (3H, m), 7.97(1H, d, J=8.8Hz)<br>MASS: 455(M + H)⁺ |

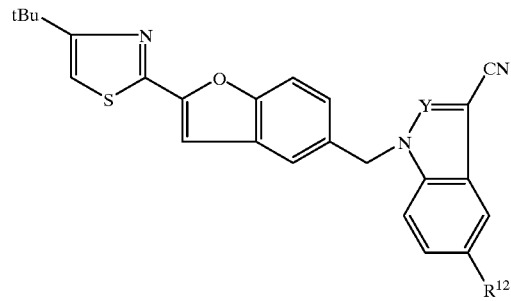

Example 51

A mixture of 4-tert-butyl-2-{5-[(3-cyano-5-hydroxyindol-1-yl)methyl]benzofuran-2-yl}thiazole (250 mg), 2N-sodium hydroxide (0.677 ml) and isopropyl bromide (0.226 ml) in isopropyl alcohol (5 ml) was stirred for 1 day at 70–80° C. After being cooled to room temperature, the mixture was poured into diluted hydrochloric acid (10 ml). The resulting precipitates were collected by filtration, which was subjected to column chromatography on silica gel and eluted with a mixture of toluene and ethyl acetate. The fractions containing the objective compound were combined and concentrated under reduced pressure to give 4-tert-butyl-2-5-[(3-cyano-5-isopropoxyindol-1-yl)methyl]benzofuran-2-yl)thiazole (180 mg).

IR (Nujol): 2200, 1220 cm⁻¹

NMR (CDCl₃, δ): 1.36 (6H, d, J=6.0 Hz), 1.40 (9H, s), 4.59 (1H, hept, J=6.0 Hz), 5.38 (2H, s), 6.90 (1H, dd, J=2.4, 8.9 Hz), 6.99 (1H, s), 7.12 (1H, dd, J=1.8, 8.5 Hz), 7.20 (1H, d, J=2.4 Hz), 7.24 (1H, d, J=8.9 Hz) 7.39 (1H, s), 7.51 (1H, d, J=8.5 Hz), 7.58 (1H, s)

MASS: 470 (M+H)⁺

Example 52

The following compound was obtained according to a similar manner to that of Example 51.

4-tert-Butyl-2-{5-[(3-cyano-5-cyclopentyloxyindol-1-yl)methyl]benzofuran-2-yl}thiazole IR (Nujol): 2200, 1210 cm$^{-1}$ NMR (CDCl$_3$, δ): 1.42 (9H, s), 1.52–1.89 (8H, m), 4.81 (1H, m), 5.38 (2H, s), 6.88 (1H, dd, J=2.4, 8.9 Hz), 6.90 (1H, s), 7.09–7.17 (2H, m), 7.23 (1H, d, J=8.9 Hz), 7.42 (2H, br s), 7.51 (1H, d, J=8.5 Hz), 7.57 (1H, s)

MASS: 496 (M+H)$^+$

Example 53

The following compound was prepared by a similar manner to that of Example 18.

2-{1-{[2-(4-tert-Butylthiazol-2-yl)benzofuran-5-yl]methyl}indol-3-yl}-2-methylpropionic acid mp: 176–183° C. (dec.)

IR (Nujol): 3700, 1710, 1610, 1580, 1540 cm$^{-1}$

NMR (CDCl$_3$, δ): 1.39 (9H, s), 1.64 (6H, s), 5.26 (7H, s), 6.95 (1H, s), 6.98 (1H, s), 7.0–7.2 (3H, m), 7.21 (1H, s), 7.25–7.29 (2H, m), 7.42 (1H, d, J=8.4 Hz), 7.72 (1H, d, J=7.6 Hz)

MASS: 473 (M+H)$^+$, 427, 270

Example 54

A mixture of 4-tert-butyl-2-[5-(3-chloropropyl)-benzofuran-2-yl]thiazole (0.19 g), 3-cyano-6-methylindole (73 mg), sodium hydroxide (90 mg) and small amount of cetyl trymethylammonium chloride in tetrahydrofuran (1 ml) was stirred at 60° C. for 1 day. After the mixture was cooled to room temperature, the insolble mass was filtered off and the filtrate was concentrated under reduced pressure to give a syrup. The syrup was subjected to column chromatography on silica gel and eluted with a mixture of n-hexane and ethyl acetate. The fraction containing the objective compound were combined and concentrated under reduced pressure to give 4-tert-butyl-2-{5-[3-(3-cyano-6-methylindole-1-yl)propyl]-benzofuran-2-yl}thiazole (90 mg).

IR (Neat): 3100, 3000, 2200, 1585, 1530, 1450 cm$^{-1}$

NMR (CDCl$_3$, δ): 1.41 (9H, s), 2.18–2.35 (2H, m), 2.48 (3H, s), 2.73 (2H, t, J=7.7 Hz), 4.15 (2H, t, J=7.1 Hz), 6.95 (1H, s), 7.11 (1H, dd, J=1.8, 8.6 Hz), 7.13–7.27 (3H, m), 7.37 (1H, s), 7.48 (1H, d, J=8.6 Hz), 7.53 (1H, s), 7.56 (1H, s)

MASS: 454 (M+H)$^+$

Example 55

A mixture of 2-(4-tert-butylthiazol-2-yl)benzofuran-5-carbonyl chloride hydrochloride (140 mg), benzyl indole-3-carboxylate (73.3 mg), triethylamine (0.089 ml) and N,N-dimethylaminopyridine (4 mg) in dichloromethane (4 ml) was stirred under reflux for 7 hours. After being cooled to room temperature, the mixture was treated with N,N-dimethylpropylenediamine (0.018 ml) and diluted with dichloromethane. The dichloromethane solution was washed with brine, dried over magnesium sulfate and concentrated under reduced pressure. The resulting residue was subjected to column chromatography on silica gel and eluted with a mixture of n-hexane and ethyl acetate. The fractions containing the objective compound were combined and concentrated under reduced pressure to give benzyl 1-{[2-(4-tert-butylthiazol-2-yl)benzofuran-5-yl]carbonyl}indole-3-carboxylate (121 mg).

IR (Nujol): 1700, 1580, 1550 cm$^{-1}$

NMR (CDCl$_3$, δ): 1.43 (9H, s), 5.39 (2H, s), 7.06 (1H, s), 7.30–7.50 (8H, m), 7.60–7.80 (2H, m), 8.05 (1H, s), 8.09 (1H, s), 8.20–8.25 (1H, m), 8.29–8.34 (1H, m)

MASS: 535 (M+H)$^+$

Example 56

The following compounds were prepared by a similar manner to that of Example 55.

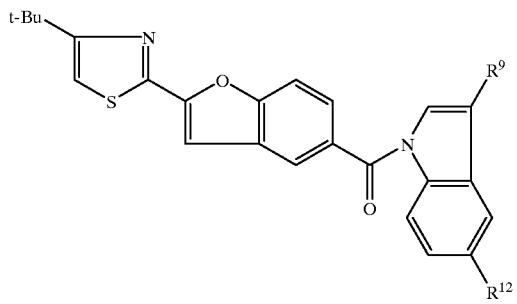

| Example | R$^9$ | R$^{12}$ | Physical data |
|---|---|---|---|
| 56-1 | —CH$_2$COOBzl | H | IR(Neat): 1730, 1680 cm$^{-1}$<br>NMR(CDCl$_3$, δ): 1.43(9H, s), 3.77(2H, s), 5.15(2H, s), 7.05 (1H, s), 7.30–7.42(9H, m), 7.55–7.76(3H, m), 8.02(1H, d, J=1.1Hz), 8.38(1H, d, J=7.4Hz)<br>MASS: 549(M + H)$^+$ |
| 56-2 | —CH$_2$COOBzl | NO$_2$ | IR(Nujol): 1725, 1678, 1515, 1335 cm$^{-1}$<br>NMR(CDCl$_3$, δ): 1.44(9H, s), 3.82 (2H, s), 5.17(2H, s), 7.07(1H, s), 7.33(5H, s), 7.45(1H, s), 7.56(1H, s), 7.69(1H, d, J=9.0Hz), 7.74(1H, dd, J=9.0, 1.5Hz), 8.05(1H, s), 8.29(1H, dd, J=9.1, 2.1Hz), 8.48(1H, d, J=9.1Hz), 8.50(1H, d, J=2.1Hz)<br>MASS: 594(M + H)$^+$ |
| 56-3 | —CH$_2$COOBzl | OMe | IR(Neat): 1730, 1670, 1260 cm$^{-1}$<br>NMR(CDCl$_3$, δ): 1.43(9H, s), 3.73 (2H, s), 3.81(3H, s), 5.14(2H, s), 6.98–7.05(3H, m), 7.25–7.43 (7H, m), 7.64(1H, d, J=8.6Hz), 7.72(1H, dd, J=8.6, 1.6Hz), 8.00 (1H, d, J=1.3Hz), 8.29(1H, d, J=9.8Hz)<br>MASS: 579(M + H)$^+$ |
| 56-4 | —(CH$_2$)$_2$COOBzl | H | IR(Nujol): 1730, 1675 cm$^{-1}$<br>NMR(CDCl$_3$, δ): 1.43(9H, s), 2.75 (2H, t, J=7.5Hz), 3.07(2H, t, J=7.5Hz), 5.10(2H, s), 7.05(1H, s), 7.14(1H, 5), 7.22–7.72(11H, m), 7.95(1H, s), 8.36(1H, d, J=7.2Hz)<br>MASS: 563(M + H)$^+$ |
| 56-5 | —CO—COOBzl | H | IR(Nujol): 1725, 1658 cm$^{-1}$<br>NMR(DMSO-d$_6$, δ): 1.39(9H, s), 5.29(2H, s), 7.25–7.30(5H, m), 7.52(2H, m), 7.58(1H, s), 7.65 (1H, s), 7.89(1H, d), 7.96(1H, d), 8.25–8.32(3H, m), 8.57(1H, 3)<br>MASS: 563(M + H)$^+$ |

Example 57

A mixture of benzyl 1-{[2-(4-tert-butylthiazol-2-yl)benzofuran-5-yl]carbonyl}-5-nitroindol-3-acetate (450 mg), iron powders (450 mg) and ammonium chloride (45 mg) in a mixed solvent of ethanol (7 ml) and water (3 ml) was stirred under reflux for 1 hour. After being cooled to room temperature, the mixture was filtered and the filtrate was concentrated under reduced pressure. The resulting residue was subjected to column chromatography on silica gel and eluted with a mixture of toluene and ethyl acetate. The fractions containing the objective compound were combined and concentrated under reduced pressure to give benzyl 5-amino-1-{[2-(4-tert-butylthiazol-2-yl)benzofuran-5-yl] carbonyl}indole-3-acetate (259 mg).

IR (Neat): 3500–2800, 1725, 1665, 1615, 1550 cm$^{-1}$

NMR (CDCl$_3$, δ): 1.43 (9H, s), 3.67 (4H, s), 5.14 (2H, s), 6.76 (2H, m), 7.04 (1H, s), 7.24 (1H, s), 7.31 (5H, s), 7.39 (1H, s), 7.63 (1H, d, J=8.6 Hz), 7.69 (1H, dd, J=1.5, 8.6 Hz), 7.98 (1H, d, J=1.5 Hz), 8.19 (1H, d, J=9.3 Hz)

MASS: 564 (M+H)$^+$

Example 58

A solution of benzyl 1-{[2-(4-tert-butylthiazol-2-yl) benzofuran-5-yl]carbonyl}indole-3-carboxylate (107 mg) in tetrahydrofuran (4 ml) was hydrogenated over 10% Pd—C (22 mg) at room temperature under atmospheric pressure. After removal of the catalyst by filtration, the filtrate was concentrated under reduced pressure to give 1-{[2-(4-tert-butylthiazol-2-yl)benzofuran-5-yl]carbonyl}indole-3-carboxylic acid (74.5 mg).

IR (Nujol): 1680, 1675, 1550 cm$^{-1}$

NMR (DMSO-d$_6$, δ): 1.38 (9H, s), 5.39 (2H, s), 7.46 (2H, s), 7.56 (1H, s), 7.70 (1H, s), 7.80–8.00 (3H, m), 8.13–8.31 (3H, m)

MASS 445 (M+H)$^+$

Example 59

The following compounds were prepared by a similar manner to that of Example 58.

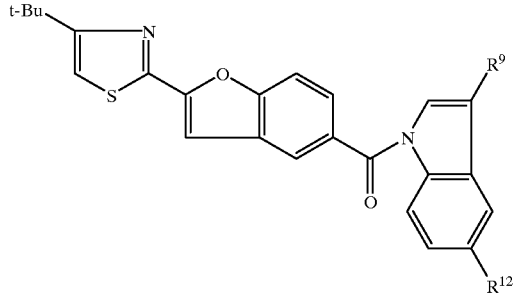

| Example | R$^9$ | R$^{12}$ | Physical Data |
|---|---|---|---|
| 59-1 | —CH$_2$COOH | H | IR(Nujol): 1700, 1680 cm$^{-1}$ NMR(CDCl$_3$, δ): 1.42(9H, s), 3.20(1H, br s), 3.75(2H, s), 7.04(1H, s), 7.26–7.80(7H, m), 8.02(1H, d, J=1.4Hz), 8.35(1H, dd, J=7.0, 1.4Hz) MASS: 459(M + H)$^+$ |
| 59-2 | —CH$_2$COOH | NO$_2$ | IR(Nujol): 1670, 1590, 1470 cm$^{-1}$ NMR(DMSO$_6$, δ): 1.37(9H, s), 3.53 (2H, s), 6.67(1H, d), 6.69(1H, s), 7.23(1H, s), 7.54(1H, s), 7.67(1H, s), 7.73(1H, d), 7.91 (1H, d), 7.99(1H, d), 8.09(1H, s) |
| 59-3 | —CH$_2$COOH | NH$_2$ | IR(Nujol): 2800–3500, 1670 cm$^{-1}$ NMR (CDCl$_3$, δ): 1.41(9H, s), 3.58 (2H, s), 4.78(2H, br s), 6.74 (1H, d, J=8.7Hz), 6.87(1H, s), 7.02(1H, s), 7.21(1H, s), 7.37 (1H, s), 7.59(1H, d, J=8.6Hz), 7.67(1H, d, J=8.6Hz), 7.93(1H, s), 8.12(1H, d, J=8.7Hz MASS: 474(M + H)$^+$ |
| 59-4 | —CH$_2$COOH | OMe | IR(Nujol): 1690, 1670, 1265 cm$^{-1}$ NMR(CDCl$_3$, δ): 1.42(9H, s), 3.72 (2H, s), 3.88(3H, s), 6.98–7.04 (3H, m), 7.34(1H, s), 7.45(1H, s), 7.65(1H, d), 7.73(1H, dd), 8.01(1H, s), 8.38(1H, d) MASS: 489(M + H)$^+$ |
| 59-5 | —(CH$_2$)$_2$COOH | H | IR(Nujol): 1700, 1680 cm$^{-1}$ NMR(CDCl$_3$, δ): 1.41(9H, s), 2.78(2H, t, J=7.3Hz), 3.06(2H, t, J=7.3Hz), 7.03(1H, s), 7.21 (1H, s), 7.35(2H, m), 7.42(1H, s), 7.58(1H, dd, J=8.4, 1.7Hz), 7.65(1H, s), 7.71(1H, dd, J=8.6, 1.5Hz), 8.34(1H, d, J=6.9Hz) MASS: 473(M + H)$^+$ |
| 59-6 | COCOOH | H | IR(Nujol): 3300, 1755, 1690 cm$^{-1}$ NMR(DMSO-d$_6$, δ): 1.38(9H, s), 7.49–7.53(2H, m), 7.56(1H, s), 7.70(1H, s), 7.91(1H, d, J=8.6Hz), 7.99(1H, d, J=8.6Hz), 8.23–8.33(3H, m), 8.55(1H, s) MASS: 473(M + H)$^+$ |

Example 60

The following compounds were prepared by a similar manner to that of Example 17.

| Example | R$^{26}$ | Physical Data |
|---|---|---|
| 60-1 | Me | IR(Neat): 1695 cm$^{-1}$ NMR(CDCl$_3$, δ): 1.39(9H, s), 1.99(3H, d, J=7.0Hz), 5.41(2H, s), 5.76(1H, q, J=7.0Hz), 6.96(1H, s), 7.08–7.52(7H, m), |

Example 61

The following compounds were prepared by a similar manner to that of Example 58.

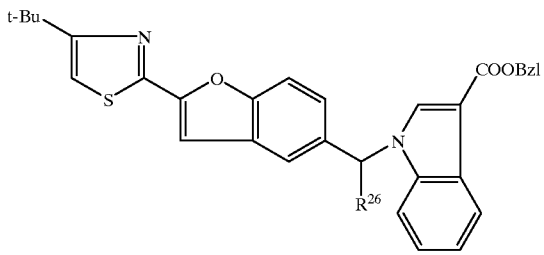

| Example | R²⁶ | Physical Data |
|---|---|---|
| | | 8.09(1H, s), 8.19(1H, d, J=7.9Hz) |
| | | MASS: 535(M + H)⁺ |
| 60-2 | Et | IR(Nujol): 1700 cm⁻¹ |
| | | NMR(CDCl₃, δ): 1.01(3H, t, J=7.2Hz), 1.42 (9H, s), 2.39(2H, m), 5.41(1H, s), 5.45 (1H, t, J=7.2Hz), 6.98(1H, s), 7.14–7.53 (12H, m), 8.11(1H, s), 8.17(1H, dd) |
| | | MASS: 549(M + H)⁺ |
| 60-3 | Ph | IR(Neat): 1700 cm⁻¹ |
| | | NMR(CDCl₃, δ): 1.40(9H, s), 5.36 (2H, s), 6.94(1H, s), 6.98(1H, s), 7.09–7.49(17H, m), 7.60(1H, s), 8.20(1H, dd, J=8.3, 1.4Hz) |
| | | MASS: 597(M + H)⁺ |

Example 61

The following compounds were prepared by a similar manner to that of Example 58.

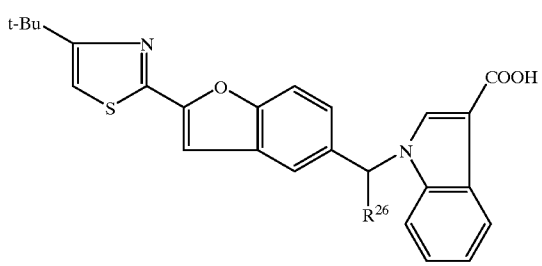

| Example | R²⁶ | Physical Data |
|---|---|---|
| 61-1 | Me | IR(Nujol): 3500–2500, 1655 cm⁻¹ |
| | | NMR(DMSO-d₆, δ): 1.34(9H, s), 1.98(3H, d, J=6.9Hz), 6.05(1H, q, J=6.9Hz), 7.14–7.19(2H, m), 7.38–7.68(6H, m), 8.03(1H, dd, J=6.1, 3.0Hz), 8.34(1H, s), 12.08(1H, br s) |
| | | MASS: 445(M + H)⁺ |
| 61-2 | Et | IR(Nujol): 3500–2400, 1650 cm⁻¹ |
| | | NMR(DMSO-d₆, δ): 0.90(3H, t, J=7.5Hz), 1.34(9H, s), 2.40(2H, quint), 5.77(1H, t, J=7.5Hz), 7.15–7.19(2H, m), 7.46–7.51(3H, m), 7.63–7.70(2H, m), 7.79(1H, s), 8.01 (1H, br m), 8.39(1H, s), 12.08(1H, s) |
| | | MASS: 459(M + H)⁺ |
| 61-3 | Ph | IR(Nujol): 3300–2500, 1660 cm⁻¹ |
| | | NMR(CDCl₃, δ): 1.40(9H, s), 6.95(1H, 5), 6.99(1H, s), 7.11–7.39(11H, m), 7.53(1H, d, J=8.5Hz), 7.63(1H, s), 8.23(1H, d, J=8.0Hz) |
| | | MASS: 507(M + H)⁺ |

Example 62

The following compounds were prepared by a similar manner to that of Example 15.

1) 1-{1-[2-(4-tert-Butylthiazol-2-yl)benzofuran-5-yl]ethyl-}indole-3-carbonitrile IR (Nujol): 2200 cm⁻¹

NMR (CDCl₃, δ): 1.40 (9H, s), 2.00 (3H, d, J=7.0 Hz), 5.80 (1H, q, J=7.0 Hz), 6.99 (1H, s), 7.12 (1H, dd, J=8.6, 1.9 Hz), 7.19–7.34 (3H, m), 7.40 (1H, d, J=1.6 Hz), 7.50 (1H, d, J=8.6 Hz), 7.75–7.79 (2H, m)

MASS: 426 (M+H)⁺

2) 1-{1-[2-(4-tert-Butylthiazol-2-yl)benzofuran-5-yl]propyl}indole-3-carbonitrile IR (Neat): 2200 cm⁻¹

NMR (CDCl₃, δ): 0.96 (3H, t, J=7.3 Hz), 1.40 (9H, s), 2.39 (2H, quint, J=7.3 Hz), 5.46 (1H, t, J=7.3 Hz), 6.98 (1H, s), 7.14 (1H, dd, J=8.5, 1.9 Hz), 7.21–7.40 (4H, m), 7.45 (1H, s), 7.47 (1H, d, J=8.5 Hz), 7.76 (1H, m), 7.83 (1H, s)

MASS: 440 (M+H)⁺

3) 7-Benzyloxy-1-{[2-(4-tert-butylthiazol-2-yl)benzofuran-5-yl]methyl}indole-3-carbaldehyde IR (Nujol): 1665, 1265 cm⁻¹

NMR (CDCl₃, δ): 1.40 (9H, s), 5.07 (2H, s), 5.70 (2H, s), 6.81 (1H, d, J=7.4 Hz), 6.94 (1H, dd, J=8.5, 1.8 Hz), 6.97 (1H, s), 7.12–7.36 (8H, m), 7.41 (1H, d, J=8.5 Hz), 7.66 (1H, s), 7.95 (1H, dd, J=8.0, 0.7 Hz), 10.0 (1H, s)

MASS: 520 (M⁺), 377, 271, 256

Example 63

1-{[2-(4-tert-butylthiazol-2-yl)benzofuran-5-yl]methyl}-5-hydroxyindole-3-acetic acid (0.1 g) which was prepared according to same manner to the hydrogenation step of example 24 was dissolved into ethyl acetate. The solution was treated with 4N-hydrogen chloride in ethyl acetate and the resulting precipitates were collected by filtration and washed with diisopropyl ether to give 1-{[2-(4-tert-butylthiazol-2-yl)benzofuran-5-yl]methyl}-5-hydroxyindole-3-acetic acid hydrochloride (90 mg).

mp: 145–150° C. (dec.)

NMR (Nujol): 3300, 2500–2700, 1700, 1585, 1460 cm⁻¹

NMR (DMSO-d₆, δ): 1.35 (9H, s), 3.56 (2H, s), 5.39 (2H, s), 6.62 (1H, dd, J=1.6, 8.7 Hz), 6.83 (1H, d, J=1.6 Hz), 7.23–7.30 (2H, m), 7.32 (1H, s), 7.46 (1H, s), 7.49 (1H, s), 7.57 (1H, br s), 7.63 (1H, d, J=8.6 Hz), 6.0–7.0 (1H, br s)

MASS: 461 (M+H)⁺

Example 64

The following compound was prepared by a similar manner to that of Example 25.

Methyl 1-{[2-(4-tert-butylthiazol-2-yl)benzofuran-5-yl]methyl}-5-[3',5'-bis(trifluoromethyl)benzyloxy-)indole-3-acetate IR (Neat): 1720, 1615, 1485, 1450 cm⁻¹

NMR (CDCl₃, δ): 1.40 (9H, s), 3.70 (3H, s), 3.75 (2H, s), 5.20 (2H, s), 5.34 (2H, s), 6.93 (1H, dd, J=2.4, 8.4 Hz), 6.97 (1H, s), 7.10–7.24 (4H, m), 7.36 (1H, s), 7.47 (1H, d, J=8.4 Hz), 7.84 (2H, m), 7.95 (2H, s)

Example 65

Diethyl azodicarboxylate (0.095 ml) was added to a mixture of methyl 1-{[2-(4-tert-butylthiazol-2-yl)benzofuran-5-yl]methyl}-5-hydroxyindole-3-acetate (0.114 g), methyl [1-(hydroxymethyl)cyclopropane]acetate (0.104 g) and triphenylphosphine (0.16 g) in tetrahydrofuran (5 ml) was stirred at room temperature for 3 days. After removal of solvent, the residue was subjected to column chromatography on silica gel and eluted with a mixture of n-hexane and ethyl acetate. The fractions containing the objective compound were combined and concentrated under reduced pressure to give methyl {1-{{{1-{[2-(4-tert-butylthiazol-2-yl)

benzofuran-5-yl]methyl}-3-(methoxycarbonylmethyl) indol-5-yl}oxy}methyl}cyclopropane}acetate (0.07 g).

IR (Neat): 1730, 1615, 1580, 1480 cm$^{-1}$

MASS: 601 (M+H)$^+$

Example 66

A mixture of methyl 1-{[2-(4-tert-butylthiazol-2-yl) benzofuran-5-yl]methyl}-5-(N',N'-dimethylcarbamoylmethoxy)indole-3-acetate (0.15 g) and 1N-lithium hydroxide (0.52 ml) in methanol (2 ml) was stirred at room temperature for 8 hours. After removal of solvent, the residue was dissolved into water and the solution was acidified with diluted hydrochloric acid. The resulting precipitates were collected by filtration and washed with water to give 1-{[2-(4-tert-butylthiazol-2-yl)benzofuran-5-yl]methyl}-5-(N',N'-dimethylcarbamoylmethoxy)indole-3-acetic acid (80 mg).

IR (Nujol): 2500–2700, 1715, 1620, 1570, 1480 cm$^{-1}$

NMR (CDCl$_3$, δ): 1.40 (9H, s), 2.94 (3H, s), 3.06 (3H, s), 3.76 (2H, s), 4.69 (2H, s), 5.28 (2H, s), 6.86 (1H, dd, J=2.3, 8.8 Hz), 6.96 (1H, s), 7.05–7.14 (4H, m), 7.20 (1H, s), 7.30 (1H, s), 7.42 (1H, s, J=8.5 Hz)

MASS: 546 (M+H)$^+$

Example 67

Sodium hydride (60% in mineral oil, 78 mg) was added into a solution of ethyl 4-(5-indolyloxy)butylate (0.40 g) in N,N-dimethylformamide (2 ml) at room temperature. After being stirred for 30 minutes at room temperature, 4-tert-butyl-2-[5-(chloromethyl)benzofuran-2-yl]thiazole (0.59 g) was added to the solution. After being stirred continuously 5 hours, the resulting mixture was poured into ice-water and the mixture was acidified with diluted hydrochloric acid and extracted with ethyl acetate. The organic layer was washed with brine, dried over magnesium sulfate and concentrated under reduced pressure to give a syrup. The syrup was subjected to column chromatography on silica gel and eluted with a mixture of n-hexane and ethyl acetate. The fractions containing the objective compound were combined and concentrated under reduced pressure to give ethyl 4-{1-{[2-(4-tert-butylthiazol-2-yl)benzofuran-5-yl]methyl}indol-5-yloxy}butylate (0.2 g).

IR (Neat): 3100, 1725, 1615, 1570, 1485, 1440, 1360 cm$^{-1}$

NMR (CDCl$_3$, δ): 1.25 (3H, t, J=7.1 Hz), 2.12 (2H, sext, J=7.4 Hz), 2.53 (2H, t, J=7.4 Hz), 4.04 (2H, t, J=7.4 Hz), 4.13 (2H, q, J=7.1 Hz), 5.37 (2H, s), 6.46 (1H, s), 6.82 (1H, dd, J=2.4, 8.9 Hz), 6.96 (1H, s), 7.06–7.13 (4H, m), 7.17 (1H, d, J=8.9 Hz), 7.32 (1H, s), 7.43 (1H, s), 7.45 (1H, d, J=8.5 Hz)

MASS 517 (M+H)$^+$

Example 68

Phosphorus oxychloride (0.39 g) was added into N,N-dimethylformamide (2 ml) under ice-cooling. After 30 minutes, a solution of ethyl 4-{1-{[2-(4-tert-butylthiazol-2-yl)benzofuran-5-yl]methyl}indol-5-yloxy}butylate in N,N-dimethylformamide (2 ml) was added to the mixture. After being stirred at room temperature for 1 hour, the resulting solution was poured into aqueous sodium hydrogen carbonate solution. The precipitates were collected by filtration, washed with water and subjected to column chromatography on silica gel and eluted with a mixture of n-hexane and ethyl acetate. The fractions containing the objective compound were combined and concentrated under reduced pressure to give 1-{[2-(4-tert-butylthiazol-2-yl)benzofuran-5-yl] methyl}-5-[3-(ethoxycarbonyl)propoxy]indole-3-carbaldehyde (0.32 g).

IR (Neat): 3100, 2950, 1720, 1650, 1615, 1575, 1525, 1500 cm$^{-1}$

NMR (CDCl$_3$, δ): 1.26 (3H, t, J=7.3 Hz), 2.07–2.20 (2H, m), 2.53 (2H, t, J=7.4 Hz), 4.09 (2H, t, J=6.3 Hz), 4.17 (2H, q, J=7.3 Hz), 5.41 (2H, s), 6.91 (1H, dd, J=2.5, 8.9 Hz), 6.99 (1H, s), 7.13–7.29 (3H, m), 7.41 (1H, s), 7.52 (1H, d, J=8.7 Hz), 7.68 (1H, s), 7.80 (1H, d, J=2.5 Hz), 9.95 (1H, s)

MASS: 545 (M+H)$^+$

Example 69

Sodium chloride (19 mg) was added to a mixture of 1-{[2-(4-tert-butylthiazol-2-yl)benzofuran-5-yl]methyl}-5-[3-(ethoxycarbonyl)propoxy]indole-3-carbaldehyde (0.31 g), sodium hydrogenphosphate 12 water (90 mg) and 2-methyl-2-butane (0.27 ml) in a mixed solvent of water (1.5 ml), tetrahydrofuran (2.2 ml) and tert-butanol (6.5 ml). After 2 days, aqueous sodium hydrogensulfide solution was added to the mixture. The resulting mixture was extracted with ethyl acetate. The organic layer was washed with brine, dried over magnesium sulfate and concentrated under reduced pressure. The residue was subjected to column chromatography on silica gel and eluted with a mixture of toluene and ethyl acetate. The fractions containing the objective compound were combined and concentrated under reduced pressure to give 1-{[2-(4-tert-butylthiazol-2-yl) benzofuran-5-yl]methyl}-5-[3-(ethoxycarbonyl)propoxy] indole-3-carboxylic acid (0.10 g).

IR (Nujol): 2500–2700, 1735, 1655, 1610, 1575, 1525, 1440 cm$^{-1}$

NMR (DMSO-d$_6$, δ): 1.17 (3H, t, J=7 Hz), 1.34 (9H, s), 1.90–2.05 (2H, m), 2.47 (2H, t, J=7.1 Hz), 3.98 (2H, t, J=6.2 Hz), 4.06 (2H, q, J=7.1 Hz), 5.56 (2H, s), 6.82 (1H, dd, J=2.2, 9.0 Hz), 7.36 (1H, d, J=8.5 Hz), 7.40–7.50 (4H, m), 7.62 (1H, s), 7.67 (1H, d, J=8.5 Hz), 8.21 (1H, s), 12.01 (1H, s)

MASS: 561 (M+H)$^+$

Example 70

A mixture of 1-{[2-(4-tert-butylthiazol-2-yl)benzofurn-5-yl]methyl}-5-[3-(ethoxycarbonyl)propoxy]indole-3-carbaldehyde (0.19 g), malonic acid (73 mg) and pyridine (0.5 ml) and piperazine (0.04 ml) was stirred at 80° C. for 3 hours. After being cooled to the room temperature, the resulting mixture was poured into ice-water and the mixture was acidified with diluted hydrochloric acid and extracted with ethyl acetate. The organic layer was washed with brine, dried over magnesium sulfate and concentrated under reduced pressure. The syrup was subjected to column chromatography on silica gel and eluted with a mixture of toluene and ethyl acetate. The fractions containing the objective compound were combined and concentrated under reduced pressure to give (E)-3-{1-{[2-(4-tert-butylthiazol-2-yl)benzofuran-5-yl]methyl}-5-[3-(ethoxycarbonyl) propyloxy]indole-3-yl}propenoic acid (25 ml).

IR (Nujol): 3300, 2500–2500, 1720, 1670, 1600, 1520 cm$^{-1}$

NMR (CDCl$_3$, δ): 1.26 (3H, t, J=7.1 Hz), 2.12–2.21 (2H, m), 2.55 (2H, t, J=7.2 Hz), 4.05–4.21 (4H, m), 5.38 (2H, s), 6.35 (1H, d, J=15.9 Hz), 6.89 (1H, dd, J=2.28, 8.9 Hz), 6.98 (1H, s), 7.12 (1H, dd, J=1.8, 8.6 Hz), 7.20 (1H, d, J=8.9 Hz), 7.36–7.38 (3H, m), 7.44 (1H, s), 7.48 (1H, d, J=8.6 Hz), 7.98 (1H, d, J=15.9 Hz)

MASS: 587 (M+H)$^+$

Example 71

Sodium hydride (84 mg, 60% in mineral oil) was added to a mixture of 4-tert-butyl-2-[5-(chloromethyl)benzofuran- 2-yl]thiazole (0.40 g), methyl indole-6-carboxylate (0.28 g) and potassium iodide (0.22 g) in N,N-dimethylformamide (3 ml) and the mixture was stirred at room temperature. After being stirred at room temperature for 5 hours, the mixture was poured into ice-water and extracted with ethyl acetate. The extract was washed with water and brine, dried over magnesium sulfate and evaporated under reduced pressure. The residue was subjected to column chromatography on silica gel and eluted with a mixture of toluene and ethyl acetate. The fractions containing the objective compounds were combined and concentrated under reduced pressure to give methyl 1-{[2-(4-tert-butylthiazol-2-yl)benzofuran-5-yl]methyl}indole-6-carboxylate (0.40 g).

IR (Neat): 1720, 1705, 1605, 1500 cm$^{-1}$

NMR (CDCl$_3$, δ): 1.40 (9H, s), 3.91 (3H, s), 5.48 (2H, s), 6.61 (1H, dd, J=3.1, 0.8 Hz), 6.97 (1H, s), 7.12 (1H, dd, J=1.8, 8.5 Hz), 7.24 (1H, d, J=0.8 Hz), 7.30 (1H, d, J=3.1 Hz), 7.35 (1H, s), 7.48 (1H, d, J=8.5 Hz), 7.67 (1H, d, J=8.4 Hz), 7.82 (1H, dd, J=1.3, 8.4 Hz), 8.13 (1H, br s)

MASS: 445 (M+H)$^+$

Example 72

The following compound was prepared by a similar manner to that of Example 71.

Ethyl 5-{1-{[2-(4-tert-butylthiazol-2-yl)benzofuran-5-yl-]methyl}indol-6-yl}pentanoate IR (Neat): 3100, 1730, 1680, 1630, 1600, 1500, 1350 cm$^{-1}$ NMR (CDCl$_3$, δ) 1.22 (3H, t, J=7.1 Hz), 1.40 (9H, s), 1.60–1.80 (4H, m), 2.30–2.40 (2H, m), 2.70–2.80 (2H, m), 4.09 (2H, q, J=7.1 Hz), 5.39 (2H, s), 6.52 (1H, d, J=3.1 Hz), 6.97 (1H, s), 6.95–7.00 (1H, m), 7.07–7.14 (3H, m), 7.24 (1H, d, J=0.8 Hz), 7.35 (1H, br s), 7.46 (1H, d, J=8.5 Hz), 7.56 (1H, d, J=8.1 Hz)

MASS: 515 (M+H)$^+$

Example 73

The following compounds were prepared by a similar manner to that of Example 68.

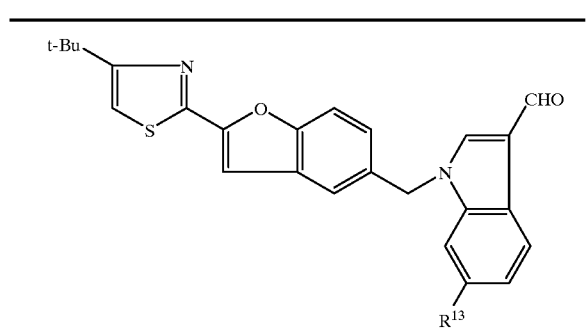

| Example | R$^{13}$ | Physical Data |
|---|---|---|
| 73-1 | —COOMe | NMR(DMSO-d$_6$, δ): 1.45(9H, s), 3.86 (3H, s), 5.78(2H, s), 7.38(1H, dd, J=1.8, 8.5Hz), 7.48(1H, s), 7.52(1H, d, J=0.7Hz), 7.66(1H, s), 7.71(1H, d, J=8.5Hz), 7.88 (1H, dd, J=1.4, 8.3Hz), 8.24(1H, d, J=8.3Hz), 8.26(1H, br s), 8.70 (1H, s), 10.01(1H, s) MASS: 473(M + H)$^+$ |
| 73-2 | -(CH$_2$)$_4$COOEt | IR(Neat): 3100, 1725, 1655, 1530, 1500 cm$^{-1}$ |

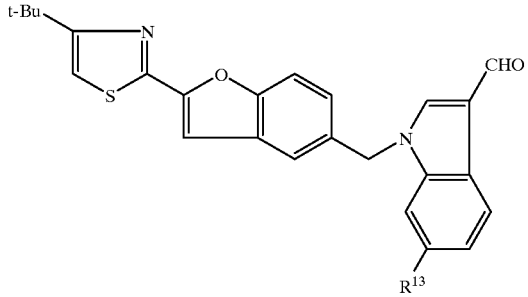

| Example | R$^{13}$ | Physical Data |
|---|---|---|
|  |  | NMR(CDCl$_3$, δ): 1.22(3H, t, J=7.1Hz), 1.40(9H, s), 1.60–1.80 (4H, m), 2.30–2.40(2H, m), 2.70–2.80(2H, m), 4.10(2H, q, J=7.1Hz), 5.34(2H, s), 6.99(1H, s), 7.16–7.29(4H, m), 7.44(1H, br s), 7.53(1H, d, J=8.5Hz), 7.67 (1H, s), 8.23(1H, d, J=8.4Hz), 9.97(1H, s) MASS: 543(M + H)$^+$ |

Example 74

The following compounds were prepared by a similar manner to that of Preparation 1.

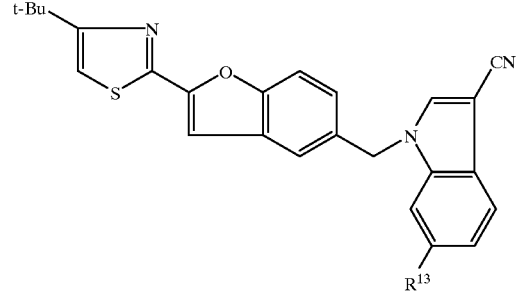

| Example | R$^{13}$ | Physical Data |
|---|---|---|
| 74-1 | —COOMe | IR(Nujol): 3100, 2320, 1710, 1620, 1530, 1500, 1240 cm$^{-1}$ NMR(CDCl$_3$, δ): 1.40(9H, s), 3.94(3H, s), 5.50(2H, s), 7.00(1H, s), 7.16 (1H, dd, J=1.7, 8.5Hz), 7.25(1H, br s), 7.42(1H, br s), 7.54(1H, d, J=8.5Hz), 7.74(1H, s), 7.82(1H, d, J=8.4Hz), 8.00(1H, dd, J=1.3, 8.4Hz), 8.20(1H, s) MASS: 470(M + H)$^+$ |
| 74-2 | -(CH$_2$)$_4$COOEt | IR(Neat): 3150, 2230, 1730, 1630, 1600, 1530, 1500 cm$^{-1}$ NMR(CDCl$_3$, δ): 1.22(3H, t, J=7.1Hz), 1.40(9H, s), 1.60–1.80(4H, m), 2.30–2.40(2H, m), 2.70–2.80(2H, m), 4.10 (2H, q, J=7.1Hz), 5.41(2H, s), 6.99 (1H, s), 7.16–7.29(2H, m), 7.28(1H, s), 7.40(1H, d, J=1.3Hz), 7.52(1H, d, J=8.5Hz), 7.57(1H, s), 7.69(1H, d, J=8.2Hz) MASS: 555(M + H)$^+$, 270 |

Example 75

The following compounds were prepared by a similar manner to that of Preparation 27.

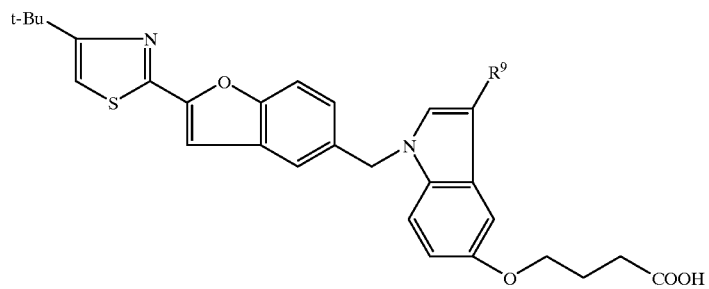

| Example | R⁹ | Physical Data |
|---|---|---|
| 75-1 | —CH₂COOH | IR(Nujol): 2700–2500, 1708, 1610, 1575 cm⁻¹<br>NNR(DMSO-d₆, δ): 1.34(9H, s), 1.94(2H, quint, J=7.0Hz), 2.39(2H, t, J=7.0Hz), 3.36(2H, s), 3.94(2H, t, J=7.0Hz), 5.44(2H, s), 6.75(1H, dd, J=2.2, 9.0Hz), 7.01(1H, d, J=2.2Hz), 7.26 (1H, d, J=8.6Hz), 7.36(1H, d, J=9.0Hz), 7.38(1H, s), 7.46(1H, s), 7.48(1H, s), 7.56(1H, s), 7.63(1H, d, J=8.6Hz), 12.16(2H, s)<br>MASS: 547(M + H)⁺ |
| 75-2 | —H | IR(Nujol): 2700–2500, 1710, 1610, 1570, 1500, 1485 cm⁻¹<br>NMR(DMSO-d₆, δ): 1.34(9H, s), 1.89–2.00 (2H, m), 2.38(2H, t, J=7.2Hz), 3.94 (2H, t, J=6.3Hz), 5.48(2H, s), 6.39 (1H, d, J=3.0Hz), 6.73(1H, dd, J=2.4, 8.9Hz), 7.05(1H, d, J=2.4Hz), 7.26 (1H, d, J=1.6, 8.6Hz), 7.36(1H, d, J=8.9Hz), 7.46–7.50(3H, m), 7.53(1H, s), 7.63(1H, d, J=8.6Hz), 12.0–12.5 (1H, br s)<br>MASS: 489(M + H)⁺ |
| 75-3 | —COOH | IR(Nujol): 2500–2700, 1680, 1650, 1610, 1575, 1525 cm⁻¹<br>NMR(DMSO-d₆, δ): 1.34(9H, s), 1.9–2.0 (2H, m), 2.40(2H, t, J=7.2Hz), 3.98 (2H, t, J=6.5Hz), 5.56(2H, s), 6.83 (1H, dd, J=2.4, 9.0Hz), 7.35(1H, dd, J=1.8, 8.6Hz), 7.45–7.50(4H, m), 7.62 (1H, s), 7.66(1H, d, J=8.6Hz), 8.21 (1H, s)<br>MASS: 533(M + H)⁺, 476 |
| 75-4 | —CH=CH—COOH (E) | NMR(DMSO-d₆, δ): 1.34(9H, s), 1.95–1.99(2H, m), 2.10(2H, t, J=7.2Hz), 4.04(2H, t, J=7.2Hz), 5.53(2H, br s), 6.27(1H, d, J=15.8Hz), 6.86(1H, d, J=9.0Hz), 7.30–7.35(2H, m), 7.45–7.50 (3H, m), 7.60–7.70(2H, m), 7.79(1H, d, J=15.8Hz), 8.10(1H, s)<br>MASS: 559(M + H)⁺ |

Example 76

The following compounds were prepared by a similar manner to that of Example 27.

1) 1-{[2-(4-tert-Butylthiazol-2-yl)benzofuran-5-yl]methyl}-5-[3',5'-bis(trifluoromethyl)benzyloxy]indole-3-acetic acid IR (Nujol): 2700, 1690, 1615, 1490 cm⁻¹

NMR (CDCl₃, δ): 1.39 (9H, s), 3.78 (2H, s), 5.18 (2H, s), 5.34 (2H, s), 6.92 (1H, dd, J=2.4, 8.8 Hz), 7.10 (1H, dd, J=1.8, 8.5 Hz), 7.11–7.24 (5H, m), 7.34 (1H, s), 7.45 (1H, d, J=8.5 Hz), 7.82 (1H, s), 7.94 (2H, s)

MASS: 687 (M+H)⁺

2) 1-{[2-(4-tert-Butylthiazol-2-yl)benzofuran-5-yl]methyl}-5-[3'-(carboxy)benzyloxy]indole-3-acetic acid IR (Nujol): 3300 (br), 2700–2500, 1690, 1610, 1580, 1480 cm⁻¹

NMR (DMSO-d₆, δ): 1.35 (9H, s), 3.63 (2H, s), 5.15 (2H, s), 5.45 (2H, s), 6.86 (1H, dd, J=2.4, 8.9 Hz), 7.16 (1H, d, J=2.4 Hz), 7.27 (1H, d, J=8.5 Hz), 7.38–7.73 (8H, m), 7.89 (1H, d, J=7.7 Hz), 8.04 (1H, s), 12.63 (2H, br s)

3) {1-{{{1-{[2-(4-tert-Butylthiazol-2-yl)benzofuran-5-yl]methyl}-3-(carboxymethyl)indol-5-yl}oxy}methyl}-cyclopropane}acetic acid IR (Nujol): 3500–2500, 1700 cm⁻¹

NMR (CDCl₃, δ): 0.66 (4H, m), 1.40 (9H, s), 2.57 (2H, s), 3.73 (2H, s), 3.90 (2H, s), 5.30 (2H, s), 6.85 (1H, dd), 6.97 (1H, s), 6.99–7.18 (6H, m), 7.44 (1H, d)

MASS: 573 (M+H)⁺

Example 77

The following compounds were prepared by a similar manner to that of Example 27.

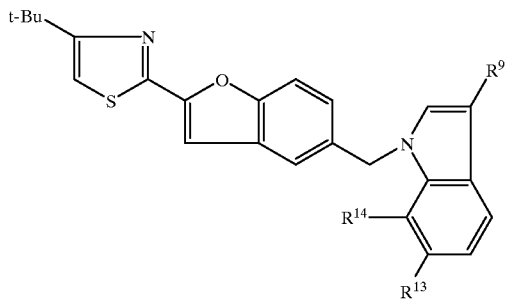

| Example | R⁹ | R¹³ | R¹⁴ | |
|---|---|---|---|---|
| 77-1 | H | COOH | H | IR(Nujol): 2500–2700, 1685, 1500, 1300 cm⁻¹<br>NMR(DMSO-d₆, δ): 1.34(9H, s), 5.64(2H, s), 6.61(1H, d, J=3.0Hz), 7.26(1H, dd, J=1.8, 8.5Hz), 7.46(1H, s), 7.50(1H, d, J=0.7Hz), 7.52(1H, br s), 7.64(2H, s), 7.66(1H, d, J=8.5Hz), 7.88(1H, dd, J=3.1Hz), 8.10(1H, s), 12.55(1H, br s)<br>MASS: 431(M + H)⁺ |
| 77-2 | Tet | COOH | H | mp: 242° C. (dec.)<br>IR(Nujol): 2500–2700, 1690, 1630, 1500 cm⁻¹<br>NMR(DMSO-d₆, δ): 1.34(9H, s), 5.80(2H, s), 7.37(1H, dd, J=1.9, 8.5Hz), 7.48(1H, s), 7.52(1H, s), 7.64(1H, s), 7.71(1H, d, J=8.4Hz), 7.86(1H, dd, J=1.1, 8.5Hz), 8.28 (1H, br s), 8.32(1H, d, J=8.5Hz), 8.41(1H, s)<br>MASS: 499(M + H)⁺ |
| 77-3 | H | –(CH₂)₄COOH | H | IR(Nujol): 2500–2700, 1710, 1500 cm⁻¹<br>NMR(CDCl₃, δ): 1.40(9H, s), 1.60–1.80(4H, m), 2.30–2.40(2H, m), 2.70–2.80(2H, m), 5.39(2H, s), 6.52(1H, d, J=3.2Hz), 6.94 (1H, d, J=8.5Hz), 6.99(1H, s), 7.06(1H, s), 7.12(1H, d, J=3.2Hz), 7.15(1H, d, J=8.5Hz), 7.25–7.30(3H, m), 7.46(1H, d, J=8.5Hz), 7.55(1H, d, J=8.2Hz)<br>MASS: 487(M + H)⁺, 288 |
| 77-4 | Tet | –(CH₂)₄COOH | H | mp: 196–197° C.<br>IR(Nujol): 3200–3000, 2500–2700, 1700, 1630, 1610, 1500, 1400, 1260 cm⁻¹<br>NMR(DMSO-d₆, δ): 1.34(9H, s), 1.44–1.70 (4H, m), 2.24(2H, t, J=7.1Hz), 2.65–2.75 (2H, m), 5.65(2H, s), 7.12(1H, d, J=8.3Hz), 7.37(1H, d, J=8.5Hz), 7.47(1H, s), 7.51(2H, s), 7.54(1H, s), 7.66(1H, br s), 7.69(1H, d, J=8.5Hz), 8.13(1H, d, J=8.3Hz), 8.14(1H, s)<br>MASS: 555(M + H)⁺ |
| 77-5 | Tet | H | —OCH₂COOH | mp: 165–168° C.<br>IR(Nujol): 3300, 2500–2700, 1720, 1620, 1580, 1500, 1460, 1380, 1200 cm⁻¹<br>NMR(DMSO-d₆, δ): 1.34(9H, s), 4.87(2H, s), 5.95(2H, s), 6.82(1H, d, J=7.8Hz), 7.14(1H, t, J=7.8Hz), 7.43(1H, dd, J=1.7, 8.5Hz), 7.46(1H, s), 7.47(1H, s), 7.64 (1H, d, J=8.5Hz), 7.71(1H, br s), 7.85(1H, d, J=7.8Hz), 8.14(1H, s)<br>MASS: 529(M + H)⁺, 309, 270 |

Example 78

The following compound was prepared by a similar manner to that of Example 36.

1-{[2-(4-tert-Butylthiazol-2-yl)benzofuran-5-yl]methyl}-7-hydroxyindole-3-carbaldehyde NMR (CDCl₃, δ): 1.41 (9H, s), 5.75 (2H, s), 6.68 (1H, d, J=7.6 Hz), 6.99 (1H, s), 7.02–7.43 (5H, m), 7.65 (1H, s), 7.86 (1H, d, J=7.9 Hz), 9.93 (1H, s)

MASS: 430 (M⁺), 287, 272

Example 79

The following compound was prepared by a similar manner to that of Preparation 1 and Example 25.

1-{[2-(4-tert-Butylthiazol-2-yl)benzofuran-5-yl]methyl}-7-(methoxycarbonylmethoxy)indole-3-carbonitrile IR (Nujol): 2230, 1750, 1580, 1500, 1460, 1380, 1350 cm⁻¹

NMR (CDCl₃, δ): 1.40 (9H, s), 3.79 (3H, s), 4.68 (2H, s), 5.85 (2H, s), 6.64 (1H, d, J=7.4 Hz), 6.98 (1H, s), 7.12–7.20 (3H, m), 7.39–7.51 (3H, m), 7.57 (1H, s)

MASS: 499 (M⁺), 270

Example 80

A mixture of methyl 1-{[2-(4-tert-butylthiazol-2-yl)benzofuran-5-yl]methyl}-3-cyanoindole-5-carboxylate (1.09 g) and sodium hydroxide (1.5 g) in a mixed solvent of water (15 ml) and methanol (30 ml) was stirred under reflux for 2 hours. After cooling, the mixture was made acidic with diluted hydrochloric acid, and the resulting precipitates were collected by filtration and washed with water to give 1-{[2-(4-tert-butylthiazol-2-yl)benzofuran-5-yl]methyl}-3-cyanoindole-5-carboxylic acid. Borane-methyl sulfide complex (2.0M) in tetrahydrofuran (1.4 ml) was added to a mixture of the acid obtained above in tetrahydrofuran (25 ml) and the mixture was stirred at room temperature for 1 day. After addition of methanol to mixture, the resulting mixture was evaporated under reduced pressure. The residue was partitioned between diluted hydrochloric acid and ethyl acetate. The ethyl acetate layer was washed with water and brine, dried over magnesium sulfate and evaporated under reduced pressure. The residue was subjected to column chromatography on silica gel and eluted with a mixture of toluene and ethyl acetate. The fractions containing the objective compounds were combined and concentrated under reduced pressure to give 1-{[2-(4-tert-butylthiazol-2-yl)benzofuran-5-yl]methyl}-5-(hydroxymethyl)indole-3-carbonitrile (0.87 g).

IR (Nujol): 3300, 2230, 1700, 1630, 1530, 1500 cm$^{-1}$

NMR (CDCl$_3$, δ): 1.40 (9H, s), 2.01 (1H, s), 4.81 (2H, s), 5.43 (2H, s), 6.99 (1H, s), 7.12 (1H, dd, J=1.9, 8.5 Hz), 7.27 (1H, s), 7.34–7.41 (3H, m), 7.51 (1H, d, J=8.5 Hz), 7.65 (1H, s), 7.78 (1H, s)

MASS: 442 (M+H)$^+$

Example 81

A mixture of 1-{[2-(4-tert-butylthiazol-2-yl)benzofuran-5-yl]methyl}-5-(hydroxymethyl)indole-3-carbonitrile (0.66 g) and thionyl chloride (0.5 ml) in chloroform (20 ml) was stirred at room temperature for 3 hours. After neutralization with aqueous sodium hydrogen carbonate, the resulting mixture was extracted with chloroform. The organic layer was washed with water and brine, dried over magnesium sulfate and evaporated under reduced pressure to give 1-{[2-(4-tert-butylthiazol-2-yl)benzofuran-5-yl]methyl}-5-(chloromethyl)indole-3-carbonitrile (0.67 g).

IR (Neat): 3120, 2230, 1700, 1630, 1600 cm$^{-1}$

NMR (CDCl$_3$, δ): 1.41 (9H, s), 4.74 (2H, s), 5.43 (2H, s), 7.00 (1H, s), 7.13 (1H, dd, J=1.8, 8.5 Hz), 7.30 (1H, d, J=0.8 Hz), 7.34–7.40 (3H, m), 7.52 (1H, d, J=8.5 Hz), 7.65 (1H, s), 7.81 (1H, s)

MASS: 460 (M+H)$^+$

Example 82

A mixture of 1-{[2-(4-tert-butylthiazol-2-yl)benzofuran-5-yl]methyl}-5-(chloromethyl)indole-3-carbonitrile (0.65 g) and potassium iodide (0.91 g) in acetone (5 ml) was stirred at room temperature for 1 hour. The mixture was evaporated under reduced pressure and the residue was dissolved with dichloromethane. After removal of the resulting insolble mass by filtration, and the filtrate was evaporated under reduced pressure to give 1-{[2-(4-tert-butylthiazol-2-yl)benzofuran-5-yl]methyl}-5-(iodomethyl)indole-3-carbonitrile (0.88 g). Methyl magnesium bromide (1M) in tetrahydrofuran solution (15 ml) was added dropwise to diethyl malonate (5.41 g) under ice-cooling. After the mixture was stirred at room temperature for 1.5 hours, 1-{[2-(4-tert-butylthiazol-2-yl)benzofuran-5-yl]methyl}-5-(iodomethyl)indole-3-carbonitrile (0.88 g) was added to the mixture. After several hours, the resulting mixture was partitioned between diluted hydrochloric acid and ethyl acetate. The ethyl acetate layer was washed with water and brine, dried over magnesium sulfate and evaporated under reduced pressure. The residue was subjected to column chromatography on silica gel and eluted with a mixture of toluene and ethyl acetate. The fractions containing the objective compounds were combined and concentrated under reduced pressure to give ethyl 3-{1-{[2-(4-tert-butylthiazol-2-yl)benzofuran-5-yl]methyl}-3-cyanoindol-5-yl}-2-(ethoxycarbonyl)propionate (0.78 g).

IR (Neat): 2200, 1730, 1530, 1500, 1360 cm$^{-1}$

NMR (CDCl$_3$, δ): 1.21 (6H, t, J=7.1 Hz), 1.40 (9H, s), 3.34 (2H, d, J=7.8 Hz), 3.69 (1H, t, J=7.8 Hz), 4.17 (1H, q, J=7.1 Hz), 5.40 (2H, s), 6.99 (1H, s), 7.12 (1H, dd, J=1.8, 8.6 Hz), 7.18–7.32 (3H, m), 7.39 (1H, d, J=1.3 Hz), 7.51 (1H, d, J=8.5 Hz), 7.61 (2H, s)

MASS: 584 (M+H)$^+$, 286

Example 83

A mixture of ethyl 3-{1-{[2-(4-tert-butylthiazol-2-yl)benzofuran-5-yl]methyl}-3-cyanoindol-5-yl}-2-ethoxycarbonylpropionate (0.72 g) and 1N sodium hydroxide solution (5 ml) in methanol (10 ml) was stirred under reflux for 3 hours. After cooling, the mixture was made acidic with diluted hydrochloric acid and extracted with ethyl acetate. The ethyl acetate layer was washed with water and brine, dried over magnesium sulfate and evaporated under reduced pressure. The residue was dissolved in xylene (10 ml) containing acetic acid (7.5 ml) and the mixture was stirred under reflux for 7 hours. After removal of solvent by evaporation, the residue was partitioned between diluted hydrochloric acid and ethyl acetate. The ethyl acetate layer was washed with water and brine, dried over magnesium sulfate and evaporated under reduced pressure. The residue was subjected to column chromatogaphy on silica gel and eluted with a mixture of chloroform and methanol. The fractions containing the objective compounds were combined and concentrated under reduced pressure to give 3-{1-{[2-(4-tert-butylthiazol-2-yl)benzofuran-5-yl]methyl}-3-cyanoindol-5-yl}propionic acid (0.78 g).

IR (Nujol): 3300–3100, 2500–2700, 1630, 1605, 1500, 1250 cm$^{-1}$

NMR (CDCl$_3$, δ): 1.40 (9H, s), 2.73 (2H, t, J=7.6 Hz), 3.08 (2H, t, J=7.6 Hz), 5.40 (2H, s), 6.99 (1H, s), 7.12 (1H, dd, J=1.7, 8.5 Hz), 7.16 (1H, dd, J=1.5, 8.5 Hz), 7.27 (1H, s), 7.31 (1H, d, J=8.5 Hz), 7.38 (1H, d, J=1.3 Hz), 7.51 (1H, d, J=8.5 Hz), 7.61 (2H, s)

MASS: 484 (M+H)$^+$

Example 84

The following compound was prepared by a similar manner to that of Example 23.

1-{[2-(4-tert-Butylthiazol-2-yl)benzofuran-5-yl]methyl}-5-methoxyindole-3-acetic acid IR (Nujol): 3200–2500, 1700, 1225 cm$^{-1}$ NMR (CDCl$_3$, δ): 1.40 (9H, s), 3.78 (2H, s), 3.84 (3H, s), 5.32 (2H, s), 6.83 (1H, dd, J=8.9, 2.4 Hz), 6.96 (1H, s), 7.05–7.26 (5H, m), 7.33 (1H, s), 7.44 (1H, d, J=8.5 Hz)

MASS: 475 (M+H)$^+$

Example 85

Sodium hydride (60% in mineral oil, 55 mg) was added into a solution of benzyl indole-3-carboxylate (0.311 g) in N,N-dimethylformamide (2 ml) under ice-cooling. After the mixture was stirred for 30 minutes at same temperature, 4-tert-butyl-2-[5-(bromoacetyl)benzofuran-2-yl]thiazole (0.47 g) was added to the mixture. After being stirred continuously 3 hours, the resulting mixture was poured into ice-water and the mixture was acidified with diluted hydrochloric acid and extracted with ethyl acetate. The organic layer was washed with brine, dried over magnesium sulfate and concentrated under reduced pressure to give a syrup. The syrup was subjected to column chromatography on silica gel and eluted with a mixture of toluene and ethyl acetate. The fractions containing the objective compound were combined and concentrated under reduced pressure. The residue was treated with 4N hydrochloride in ethyl acetate solution. The resulting precipitates were collected by filtration and washed diisopropyl ether to give the hydrochloride salt of the objective compound. The hydrochloride salt was partitioned between ethyl acetate and aqueous sodium hydrogen carbonate solution. The organic layer was washed with brine, dried over magnesium sulfate and concentrated under reduced pressure to give benzyl 1-{2-[2-(4-tert-butylthiazol-2-yl)benzofuran-5-yl]-2-oxoethyl}indole-3-carboxylate (0.14 g).

IR (Nujol): 1675, 1580, 1530, 1500, 1360 cm$^{-1}$

NMR (CDCl$_3$, δ): 1.42 (9H, s), 5.39 (2H, s), 5.60 (2H, s), 7.05 (1H, s), 7.20–7.50 (8H, m), 7.65 (1H, d, J=8.7 Hz), 7.87 (1H, s), 8.02 (1H, dd, J=1.7, 8.7 Hz), 8.20–8.25 (1H, m), 8.31 (1H, d, J=1.7 Hz)

MASS: 549 (M+H)$^+$, 505

Example 86

A solution of benzyl 1-{2-[2-(4-tert-butylthiazol-2-yl)benzofuran-5-yl]-2-oxoethyl}indole-3-carboxylate (140 mg) in tetrahydrofuran (4 ml) was hydrogenated over 10% Pd(OH)$_2$ (22 mg) at room temperature under atmospheric pressure. After removal of the catalyst by filtration the filtrate was concentrated under reduced pressure. The residue was subjected to column chromatography on silica gel and eluted with a mixture of dichloromethane and methanol. The fractions containing the objective compound were combined and concentrated under reduced pressure to give 1-{2-[2-(4-tert-butylthiazol-2-yl)benzofuran-5-yl]-2-oxoethyl}indole-3-carboxylic acid (90 mg).

IR (Nujol): 2500–2700, 1700, 1650, 1530, 1360 cm$^{-1}$

NMR (CDCl$_3$, δ): 1.43 (9H, s), 5.63 (2H, s), 7.05 (1H, s), 7.20–7.35 (3H, m), 7.43 (1H, s), 7.66 (1H, d, J=8.7 Hz), 7.95 (1H, s), 8.04 (1H, dd, J=1.7, 8.7 Hz), 8.26–8.30 (1H, m), 8.33 (1H, d, J=1.7 Hz)

MASS: 459 (M+H)$^+$

Example 87

Sodium borohydride (4 mg) was added to a solution of benzyl 1-{2-[2-(4-tert-butylthiazol-2-yl)benzofuran-5-yl]-2-oxoethyl}indole-3-carboxylate in a mixed solvent of methanol (1 ml) and tetrahydrofurane (5 ml). After being stirred for several hours, the reaction mixture was diluted with aqueous ammonium acetate solution, which was extracted with ethyl acetate. The extract was washed with brine, dried over magnesium sulfate and concentrated under reduced pressure. The residue was subjected to column chromatography on silica gel and eluted with a mixture of toluene and ethyl acetate. The fractions containing the objective compound were combined and concentrated under reduced pressure to give benzyl 1-{2-[2-(4-tert-butylthiazol-2-yl)benzofuran-5-yl]-2-hydroxyethyl}indole-3-carboxylate (70 mg).

IR (Neat): 3400, 1680, 1530, 1360 cm$^{-1}$

NMR (CDCl$_3$, δ) 1.40 (9H, s), 2.51 (1H, d, J=2.8 Hz), 4.34 (1H, d, J=2.8 Hz), 4.37 (1H, s), 5.15 (1H, br s), 5.33 (2H, s), 6.99 (1H, s), 7.23–7.55 (11H, m), 7.57 (1H, d, J=1.5 Hz), 8.15 (1H, s), 8.16–8.21 (1H, m)

MASS: 551 (M+H)$^+$

Example 88

A solution of benzyl 1-{2-[2-(4-tert-butylthiazol-2-yl)benzofuran-5-yl]-2-hydroxyethyl}indole-3-carboxylate (70 mg) and 1N sodium hydroxide (0.13 ml) in tetrahydrofuran (7 ml) was stirred at 50° C. for 1 day. After removal of solvent, the residue was dissolved into water and the solution was acidified with diluted hydrochloric acid. The resulting precipitates were collected by filtration and washed with water to give 1-{2-[2-(4-tert-butylthiazol-2-yl)benzofuran-5-yl]-2-hydroxyethyl}indole-3-carboxylic acid (50 mg).

IR (Nujol): 3350, 1660, 1530, 1360, 1230 cm$^{-1}$

NMR (DMSO-d$_6$, δ): 1.37 (9H, s), 4.30–4.50 (2H, m), 5.08 (1H, br s), 5.80 (1H, br s), 7.15–7.20 (3H, m), 7.47 (1H, s), 7.49 (1H, d, J=8.6 Hz), 7.52 (1H, s), 7.58–7.70 (3H, m), 7.78 (1H, s)

MASS: 575, 461 (M+H)$^+$

Example 89

A mixture of 4-tert-butyl-2-[5-(bromoacetyl)benzofuran-2-yl]thiazole (0.20 g), 3-cyanoindole (75 mg) and potassium carbonate (146 mg) in methylethylketone (3 ml) was stirred at 40° C. for 2 hours. After being cooled to room temperature, the mixture was poured into ice-water and the mixture was acidified with diluted hydrochloric acid and extracted with ethyl acetate. The organic layer was washed with brine, dried over magnesium sulfate and concentrated under reduced pressure. The residue was collected by trituration with diisopropyl ether to give -1-{2-[2-(4-tert-butylthiazol-2-yl)benzofuran-5-yl]-2-oxoethyl}indole-3-carbonitrile (0.20 g).

IR (Nujol): 2200, 1690, 153 0 cm$^{-1}$

NMR (CDCl$_3$, δ):1.43 (9H, s), 5.67 (2H, s), 7.06 (1H, s), 7.25–7.35 (3H, m), 7.44 (1H, s), 7.65 (1H, s), 7.69 (1H, d, J—8.7 Hz), 7.81 (1H, m), 8.04 (1H, dd, J=8.7, 1.8 Hz), 8.34 (1H, d, J=1.8 Hz)

MASS: 440 (M+H)$^+$

Example 90

The following compound was prepared by a similar manner to that of Example 87.

1-{2-[2-(4-tert-Butylthiazol-2-yl)benzofuran-5-yl]-2-hydroxyethyl}indole-3-carbonitrile IR (Nujol): 3600–3000, 2200 cm$^{-1}$ NMR (CDCl$_3$, δ): 1.39 (9H, s), 4.39 (2H, d, J=5.8 Hz), 5.14 (1H, br s), 7.00 (1H, ), 7.23–7.78 (9H, m)

MASS: 442 (M+H)$^+$

Example 91

The following compound was prepared by a similar manner to that of Example 20.

4-tert-Butyl-2-{5-[(3-cyano-2H-indazol-2-yl)methyl-]benzofuran-2-yl}thiazole mp: 143–144° C.

IR (Nujol): 2200, 1500, 1460, 1380, 1260 cm$^{-1}$

NMR (CDCl$_3$, δ): 1.40 (9H, s), 5.84 (2H, s), 6.98 (1H, s), 7.30–7.46 (4H, m), 7.53 (1H, d, J=8.5 Hz), 7.70–7.80 (2H, m), 7.86 (1H, d, J=8.0 Hz)

MASS: 413 (M+H)$^+$

Example 92

The following compounds were prepared by a similar manner to that of Example 33.

1) 5-{1-{[2-(4-tert-Butylthiazol-2-yl)benzofuran-5-yl]methyl}-5-(1-piperidinocarbonyl-1-methylethoxy)indol-3-yl}-1H-tetrazole mp: 137.8° C. (dec.)

IR (Nujol): 3500–2300, 1620, 1250 cm$^{-1}$

NMR (DMSO-d$_6$, δ): 1.34 (9H, s), 1.50 (6H, br s), 1.51 (6H, s), 3.34 (2H, br s), 3.53 (2H, br s), 5.62 (2H, s), 6.83 (1H, dd, J=2.4, 8.9 Hz), 7.38 (1H, dd, J=1.7, 8.5 Hz), 7.47 (1H, s), 7.51 (1H, s), 7.59 (1H, d, J=8.9 Hz), 7.67 (1H, s), 7.69 (1H, d, J=8.5 Hz), 7.78 (1H, d, J=2.3 Hz), 8.16 (1H, s)

MASS: 624 (M+H)$^+$ 2) 5-{1-{[2-(4-tert-Butylthiazol-2-yl)benzofuran-5-yl]methyl}-5-(2-carbamoyl-2-methylpropoxy)indol-3-yl}-1H-tetrazole mp: >230° C.

IR (Nujol): 3600–2300, 1650, 1190 cm$^{-1}$

NMR (DMSO-d$_6$, δ): 1.22 (6H, s), 1.34 (9H, s), 4.00 (2H, s), 5.64 (2H, s), 6.85–6.95 (2H, m), 7.17 (1H, br s), 7.34 (1H, d, J=8.5 Hz), 7.47 (1H, s), 7.50 (1H, s), 7.56 (1H, d, J=8.9 Hz), 7.62 (1H, s), 7.68 (1H, d, J=8.5 Hz), 7.72 (1H, s), 8.18 (1H, s)

MASS: 570 (M+H)$^+$

Example 93

The following compounds were prepared by a similar manner to that of Example 21.

1) 5-{1-{[2-(4-tert-Butylthiazol-2-yl)benzofuran-5-yl]methyl}indol-2-yl}-1H-tetrazole IR (Nujol): 2700–2500, 1590 cm$^{-1}$ NMR (CDCl$_3$, δ): 1.40 (9H, s), 6.04 (2H, s), 6.86 (1H, dd, J=1.7, 8.3 Hz), 6.88 (1H, s), 7.00 (1H, s), 7.07–7.27 (5H, m), 7.34 (1H, d, J=8.3 Hz), 7.58 (1H, d, J=7.8 Hz)

MASS : 455 (M+H)$^+$, 270

2) 5-{1-{3-[2-(4-tert-Butylthiazol-2-yl)benzofuran-5-yl]propyl}-5-methylindol-3-yl}-1H-tetrazole IR (Nujol): 2700–2500, 1620, 1590, 1500, 1460 cm$^{-1}$ NMR (CDCl$_3$, δ): 1.40 (9H, s), 2.08–2.15 (2H, m), 2.40 (3H, s), 2.52–2.60 (2H, m), 4.04 (2H, t, J=6.9 Hz), 6.94 (1H, dd, J=1.7, 8.6 Hz), 6.96 (1H, s), 7.07 (1H, d, J=8.6 Hz), 7.09–7.23 (4H, m), 8.03 (1H, s), 8.09 (1H, s)

MASS: 515, 498, 497 (M+H)$^+$, 472

3) 5-{1-{1-[2-(4-tert-Butylthiazol-2-yl)benzofuran-5-yl]ethyl}indol-3-yl}-1H-tetrazole IR (Nujol): 3100, 1620 cm$^{-1}$ NMR (DMSO-d$_6$, δ): 1.34 (9H, s), 2.00 (3H, d, J=6.7 Hz), 6.12 (1H, q), 7.22–7.69 (8H, m), 8.24 (1H, br s), 8.40 (1H, s)

MASS: 469 (M+H)$^+$ 4) 5-{1-{1-[2-(4-tert-Butylthiazol-2-yl)benzofuran-5-yl]propyl}indol-3-yl}-1H-tetrazole IR (Nujol): 3300, 1650 cm$^{-1}$ NMR (DMSO-d$_6$, δ): 0.96 (3H, t, J=7.1 Hz), 2.42 (2H, quint, J=7.1 Hz), 5.87 (1H, t, J=7.1 Hz), 7.19–7.30 (2H, m), 7.43–7.50 (3H, m), 7.65–7.77 (3H, m), 8.21 (1H, m), 8.47 (1H, s)

MASS: 483 (M+H)$^+$ 5) 5-{1-{2-[2-(4-tert-Butylthiazol-2-yl)benzofuran-5-yl]-2-hydroxyethyl}indol-3-yl}-1H-tetrazole IR (Nujol): 3600–3000 cm$^{-1}$ NMR (DMSO-d$_6$, δ): 1.37 (9H, s), 4.47 (2H, m), 5.10 (1H, br s), 5.88 (1H, d, J=4.3 Hz), 7.25 (2H, m), 7.48 (1H, s), 7.52 (2H, s), 7.67 (2H, m), 7.80 (1H, s), 8.12 (1H, s), 8.23 (1H, m)

MASS: 485 (M+H)$^+$ 6) 5-{2-{[2-(4-tert-Butylthiazol-2-yl)benzofuran-5-yl]methyl}-2H-indazol-3-yl}-1H-tetrazole mp: 180–190° C.

IR (Nujol): 3300, 2500–2700, 1500, 1370 cm$^{-1}$

NMR (DMSO-d$_6$, δ): 1.34 (9H, s), 6.29 (2H, s), 7.25–7.48 (6H, m), 7.6–7.65 (2H, m), 7.75 (1H, d, J=8.4 Hz), 8.15 (1H, br s)

MASS : 456 (M+H)$^+$, 431, 413

Example 94

To a solution of ethyl 2-(2-hydroxymethyl-6-methoxyphenoxy)propionate (1.97 g), 2-(4-tert-butylthiazol-2-yl)-5-hydroxybenzofuran (1.83 g), and triphenylphosphine (2.83 g) in tetrahydrofuran (20 ml) was added a solution of diethyl azodicarboxylate (1.67 g) in tetrahydrofuran (2 ml) under ice-cooling. The mixture was stirred at the same temperature for an hour and at room temperature for an hour. The mixture was concentrated under reduced pressure and the residue was subjected to a column of silica gel (250 ml) eluting with a mixed solvent of n-hexane and ethyl acetate (7:1) to give ethyl 2-{2-{[2-(4-tert-butylthiazol-2-yl)benzofuran-5-yloxy]methyl}-6-methoxyphenoxy}propionate (2.31 g).

IR (Film): 1740, 1605 (sh), 1585 cm$^{-1}$

NMR (CDCl$_3$, δ): 1.24 (3H, t, J=7 Hz), 1.40 (9H, s), 3.83 (3H, s), 4.16 (2H, q, J=7 Hz), 4.92 (1H, q, J=7 Hz), 5.23 (1H, d, J=12.2 Hz), 5.33 (1H, d, J=12.2 Hz), 6.84–7.45 (8H, m)

Example 95

The following compounds were prepared by a similar manner to that of Example 94.

| Example | $R^{20}$ | $R^{21}$ | $R^{22}$ | $R^{23}$ | $R^{24}$ | Physical Data |
|---|---|---|---|---|---|---|
| 95-1 | Me | Me | H | OMe | H | $[\alpha]_{27}^D$ = 11.850(c = 0.98, CHCl$_3$) |
| | | ((S)-isomer) | | | | IR(Film): 1745, 1260 cm$^{-1}$ |
| | | | | | | NMR(CDCl$_3$, δ): 1.41(9H, s), 1.58 |

-continued

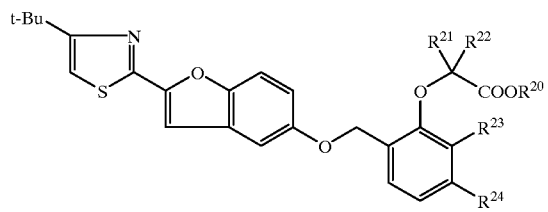

| Example | R²⁰ | R²¹ | R²² | R²³ | R²⁴ | Physical Data |
|---|---|---|---|---|---|---|
| | | | | | | (3H, s), 3.71(3H, s), 3.84(3H, s), 4.91(1H, q, J=6.9Hz), 5.22 (1H, d, J=12.2Hz), 5.32(1H, d, J=12.2Hz), 6.88(1H, dd, J=2.3, 7.4Hz), 6.96(1H, s), 6.97–7.27 (5H, m), 7.43(1H, d, J=8.9Hz) MASS: 496(M + H)⁺ |
| 95-2 | Bzh | nPr | H | OMe | H | IR(Film): 1745, 1585 cm⁻¹ NMR(CDCl₃, δ): 0.85(3H, t, J=7Hz), 1.41(9H, s), 1.40–1.60 (2H, m), 1.93(2H, m), 3.60(3H, s), 5.10(1H, m), 5.10(1H, d, J=12Hz), 5.30(1H, d, J=12Hz), 6.80–7.40(18H, m) |
| 95-3 | Me | Et | H | OMe | H | mp: 80–81° C. IR(film): 1762, 1580 cm⁻¹ NMR(CDCl₃, δ): 1.04(3H, t, J=7.2Hz), 1.41(9H, s), 2.0(2H, m), 3.70(3H, s), 3.82(3H, s), 4.87(1H, q, J=6Hz), 5.25(1H, d, J=12.4Hz), 5.35(1H, d, J=12.4Hz), 6.80–7.45(9H, m) MASS: 510(M + H)⁺ |
| 95-4 | Et | Me | Me | OMe | H | mp: 123° C. IR(film): 1732, 1585 cm⁻¹ NMR(CDCl₃, δ): 1.32(3H, t, J=7Hz), 1.41(9H, s), 1.47(6H, s), 3.75(3H, s), 4.24(2H, q, J=7Hz), 5.13(2H, s), 6.8–7.2(8H, m), 7.28(1H, s), 7.43(1H, d, J=9Hz) |
| 95-5 | tBu | H | H | OMe | H | IR(Film): 1750, 1240 cm⁻¹ NMR(CDCl₃, δ): 1.41(9H, s), 1.44 (9H, s), 3.86(3H, s), 4.61(2H, s), 5.30(2H, s), 6.89(1H, dd, J=2.7, 7.1Hz), 6.96(1H, s), 6.99–7.14(4H, m), 7.15(1H, d, J=2.5Hz), 7.42(1H, d, J=8.9Hz) MASS: 524(M + H)⁺ |
| 95-6 | Me | H | Me ((R)-isomer) | OMe | H | $[\alpha]_{27}^{D}$ = +14.060 (c = 0.8, CHCl₃) IR(Film): 1720, 1520 cm⁻¹ NMR(CDCl₃, δ): 1.41(9H, s), 1.57 (3H, d, J=7Hz), 3.70(3H, s), 3.84 (3H, s), 4.91(1H, dd, J=12.2Hz), 5.27(2H, center of a pair of dd, J=12.2Hz), 6.87(1H, dd, J=2.2, 7.5Hz), 6.95(1H, s), 6.99–7.25 (5H, m), 7.25(1H, s), 7.42(1H, d, J=9Hz) MASS: 496(M + H)⁺ |
| 95-7 | Bzh | nPr | H | H | OMe | IR(CH₂Cl₂): 1750, 1730, 1610, 1585 cm⁻¹ NMR(CDCl₃, δ): 0.88(3H, t, J=7Hz), 1.41(9H, s), 1.47(2H, m), 1.96(2H, m), 3.58(3H, s), 4.80(1H, t, J=5.6Hz), 5.07(1H, d, J=11.7Hz), 5.20(1H, d, J=11.7Hz), 6.25(1H, d, J=2.2Hz), 6.50(1H, dd, J=2.2, 8.4Hz), 6.91 (1H, s), 6.95(1H, s), 6.99(1H, dd, J=2.5, 9.0Hz), 7.1–7.4(8H, m) |

Example 96

To a solution of diphenylmethyl 2-[2-(hydroxymethyl)phenoxy]pentanoate (1.70 g), 2-(4-tert-butylthiazol-2-yl)-5-hydroxybenzofuran (2.43 g), and triphenylphosphine (2.44 g) in tetrahydrofuran (40 ml) was added a solution of diethylazodicarboxylate (1.44 g) in tetrahydrofuran (2 ml)

under ice-cooling. The mixture was stirred at the same temperature for an hour and at room temperature for an hour. The mixture was concentrated under reduced pressure and the residue was subjected to a column of silica gel (100 g) eluting with a mixed solvent of toluene and n-hexane (7:3) to give diphenylmethyl 2-{2-{[2-(4-tert-butylthiazol-2-yl)benzofuran-5-yloxy]methyl}phenoxy}pentanate (2.16 g).

IR (Film): 1750 cm$^{-1}$

NMR (CDCl$_3$, δ): 0.91 (3H, t, J=7 Hz), 1.41 (9H, s), 1.4–1.7 (4H, m), 2.0 (2H, m), 4.84 (1H, t, J=6 Hz), 5.18 (1H, d, J=12 Hz), 5.27 (1H, d, J=12 Hz), 6.65 (1H, d, J=8 Hz), 6.9–7.5 (18H, m)

MASS: 646 (M+H)$^+$

Example 97

The following compounds were prepared by a similar manner to that of Example 96.

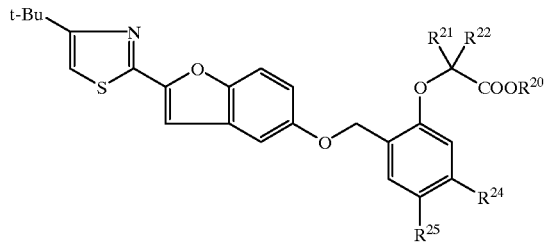

| Example | R$^{20}$ | R$^{21}$ | R$^{22}$ | R$^{24}$ | R$^{25}$ | |
|---|---|---|---|---|---|---|
| 97-1 | Bzh | nPr | H | —O—(CH$_2$)$_3$COOEt | H | IR(Nujol): 1750, 1730, 1610, 1580, 1500 cm$^{-1}$<br>NMR(CDCl$_3$, δ): 0.89(3H, t, J=7.4Hz), 1.26(3H, t, J=7.2Hz), 1.41(9H, s), 1.4–1.5(2H, m), 1.90–2.05(4H, m), 2.42(2H, q, J=7.4Hz), 3.65–3.85(2H, m), 4.11(2H, q, J=7.2Hz), 4.75–4.88 (1H, m), 5.14(2H, ABq, J=11.7Hz), 6.23 (1H, d, J=2.2Hz)6.48(1H, dd, J=2.2, 8.4Hz), 6.91(1H, s), 6.95(1H, s), 6.99(1H, dd, J=2.6, 8.9Hz), 7.13–7.41 (13H, m)<br>MASS: 776(M$^+$), 777.4(M + H)$^+$ |
| 97-2 | Bzh | nPr | H | —O—(CH$_2$)$_4$COOEt | H | IR(Nujol): 1740, 1730, 1610, 1590, 1500 cm$^{-1}$<br>NMR(CDCl$_3$, δ): 0.88(3H, t, J=7.4Hz), 1.26(3H, t, J=7.1Hz), 1.40(9H, s), 1.40–1.50(2H, m), 1.60–1.72(4H, m), 1.95–2.00(2H, m), 2.30–2.40(2H, m), 3.60–3.85(2H, m), 4.08–4.19(2H, m), 4.79(1H, t, J=7.4Hz), 5.17(2H, ABq, J=11.8Hz), 6.23(1H, d, J=2.2Hz), 6.49 (1H, dd, J=2.2, 8.6Hz), 6.90(1H, s), 6.95(1H, s), 6.99(1H, dd, J=2.5, 8.9Hz), 7.13–7.32(12H, m), 7.39(1H, d, J=8.9Hz)<br>MASS: 790(M + H)$^+$ |
| 97-3 | Bzh | nPr | H | —O—(CH$_2$)$_5$COOEt | H | IR(Nujol): 1750, 1730, 1610, 1585, 1500, 1460, 1380 cm$^{-1}$<br>NMR(CDCl$_3$, δ): 0.88(3H, t, J=7.4Hz), 1.26(3H, t, J=7.1Hz), 1.40 (9H, s), 1.40–1.52(2H, m), 1.58–1.68(4H, m), 1.94–2.05(2H, m), 2.32(2H, t, J=7.1Hz), 3.60–3.80(2H, m), 4.13(2H, q, J=7.1Hz), 4.80(1H, t, J=7.0Hz), 5.14(2H, ABq, J=11.7Hz), 6.25(1H, d, J=2.2Hz), 6.48(1H, dd, J=2.2, 8.5Hz), 6.90(1H, s), 6.95(1H, s), 6.98(1H, dd, J=2.6, 9.0Hz), 7.11–7.32(13H, m), 7.38(1H, d, J=9.8Hz)<br>MASS: 804(M$^+$) |
| 97-4 | Bzl | H | H | —O—(CH$_2$)$_3$COOEt | H | IR(Nujol): 1750, 1730, 1610, 1580, 1500 cm$^{-1}$<br>NMR(CDCl$_3$, δ): 1.26(3H, t, J=7.2Hz), 1.41(9H, 5), 2.08(2H, quint, J=6.8Hz), 3.94(2H, t, J=6.8Hz), 4.11 (2H, q, J=7.2Hz), 4.72(2H, s), 5.13 (2H, s), 5.23(2H, s), 6.36(1H, d, J=2.2Hz), 6.53(1H, dd, J=2.2, 8.4Hz), |

-continued

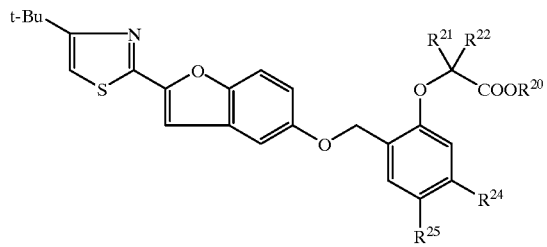

| Example | $R^{20}$ | $R^{21}$ | $R^{22}$ | $R^{24}$ | $R^{25}$ | |
|---|---|---|---|---|---|---|
| | | | | | | 6.96(1H, s), 7.33(5H, s), 7.30–7.42 (2H, m)<br>MASS: 658(M + H)$^+$ |
| 97-5 | Me | Et | H | O–(CH$_2$)$_3$–COOEt | H | IR(Nujol): 1750, 1730, 1610, 1585, 1500, 1450 cm$^{-1}$<br>NMR(CDCl$_3$, δ): 1.05(3H, t, J=7.5Hz), 1.26(3H, t, J=7.5Hz), 1.41(9H, s), 1.93–2.15(4H, m), 2.50(2H, t, J=7.5Hz), 3.76(3H, s), 3.97(2H, t, J=6.1Hz), 4.14(2H, q, J=7.2Hz), 4.64 (1H, t, J=6.0Hz), 5.13(1H, d, J=11.7Hz), 5.28(1H, d, J=11.7Hz), 6.32 (1H, d, J=2.2Hz), 6.50(1H, dd, J=2.2, 8.4Hz), 6.95(1H, s), 7.02(1H, dd, J=2.6, 9.0Hz), 7.18(1H, d, J=2.6Hz), 7.26(1H, s), 7.36(1H, d, J=8.4Hz), 7.42(1H, d, J=8.4Hz)<br>MASS: 610(M + H)$^+$ |
| 97-6 | Et | Me | Me | H | H | IR(Nujol): 1730, 1585 cm$^{-1}$<br>NMR(CDCl$_3$, δ): 1.24(3H, t, J=7Hz), 1.41(9H, s), 1.62(6H, s), 4.24(2H, q, J=7Hz), 5.17(2H, s), 6.74(1H, d, J=8Hz), 6.96(1H, s), 7.0–7.5(7H, m)<br>MASS: 466(M + H)$^+$ |
| 97-7 | Bzh | nBu | H | H | H | IR(Film): 1750 cm$^{-1}$<br>NMR (CDCl$_3$, δ): 0.82(3H, t, J=7Hz), 1.41(9H, s), 1.2–1.5(4H, m), 2.0(2H, m), 4.84(1H, t, J=7Hz), 5.18(1H, d, J=12.6Hz), 5.28(1H, d, J=12.6Hz), 6.66 (1H, d, J=8Hz), 6.9–7.6(19H, m)<br>MASS: 669(M + H)$^+$ |
| 97-8 | Et | –(CH$_2$)$_3$– | | H | H | IR(Film): 1725, 1585, 1190 cm$^{-1}$<br>NMR(CDCl$_3$, δ): 1.16(3H, t, J=7Hz), 1.41(9H, s), 2.0(2H, m), 2.35–2.55(2H, m), 2.8(2H, m), 4.20 (2H, q, J=7Hz), 5.23(2H, s), 6.41(1H, d, J=8Hz), 6.9–7.5(8H, m)<br>MASS: 506(M + H)$^+$ |
| 97-9 | Me | Et | H | H | H | IR(Nujol): 1750, 1600, 1584 cm$^{-1}$<br>NMR(CDCl$_3$, δ): 1.08(3H, t, J=7Hz), 1.41(9H, s), 2.03(2H, dt, J=6, 7Hz), 3.75(3H, s), 4.69(1H, t, J=6Hz), 5.21 (1H, d, J=13Hz), 5.30(1H, d, J=13Hz), 6.75(1H, d, J=8Hz), 6.96–7.8(8H, m)<br>MASS: 480(M + H)$^+$ |
| 97-10 | tBu | H | H | H | —O–(CH$_2$)$_3$–COOEt | mp: 82–82.5° C.<br>IR(Nujol): 3100, 1760, 1732 cm$^{-1}$<br>NMR(CDCl$_3$, δ): 1.24(3H, d, J=7Hz), 1.41(9H, s), 1.48(9H, s), 2.07(2H, m), 2.49(2H, t, J=7Hz), 3.95(2H, t, J=6Hz), 4.12(2H, q, J=7Hz), 4.54(2H, s), 5.22(2H, s), 6.7(2H, m), 6.8(1H, s), 7.0–7.3(4H, m), 7.42(1H, d, J=8Hz) |
| 97-11 | tBu | H | H | H | —O—CH$_2$—COOtBu | mp: 66–67° C.<br>IR(Nujol): 1750 cm$^{-1}$<br>NMR(CDCl$_3$, δ): 1.42(9H, s), 1.46(9H, s), 1.48(9H, s), 4.46(2H, s), 4.54 (2H, s), 5.21(2H, s), 6.7–6.8(2H, m), 6.83(1H, s), 7.0–7.4(5H, m) |

Example 98

The following compound was prepared by a similar manner to that of Example 96.

Ethyl 4-{4-{[2-(4-tert-butylthiazol-2-yl)benzofuran-5-yloxy]methyl}-3-methoxyphenoxy}butyrate
IR (Nujol): 1725, 1610, 1585, 1500, 1450, 1420 cm$^{-1}$ NMR (CDCl₃, δ) 1.26 (3H, t, J=7.4 Hz), 1.41 (9H, s), 2.07–2.18 (2H, m), 2.52 (2H, t, J=7.4 Hz), 3.84 (3H, s), 4.02 (2H, t, J=7.2 Hz), 4.15 (2H, q, J=7.4 Hz), 5.06 (2H, s), 6.46 (1H, dd, J=2.4, 8.0 Hz), 6.50 (1H, d, J=2.2 Hz), 6.95 (1H, s), 7.02 (1H, dd, J=2.7, 8.9 Hz), 7.14 (1H, d, J=2.7 Hz), 7.26 (1H, s), 7.33 (1H, d, J=8.0 Hz), 8.46 (1H, d, J=8.9 Hz)

MASS: 524 (M+H)⁺

Example 99

To a solution of ethyl 2-{2-{[2-(4-tert-butylthiazol-2-yl)benzofuran-5-yloxy]methyl}-6-methoxyphenoxy}propionate (2.30 g) in a mixed solvent of tetrahydrofuran (30 ml) and methanol (15 ml) was added 1N sodium hydroxide solution (6.8 ml) at room temperature. The solution was stirred for two hours and concentrated under reduced pressure. The residue was diluted with water and acidified with 1N hydrochloric acid and was extracted with ethyl acetate. The organic layer was washed with brine and dried over magnesium sulfate to give 2-{2-{[2-(4-tert-butylthiazol-2-yl)benzofuran-5-yloxy]methyl}-6-methoxyphenoxy}propionic acid (2.17 g) as an amorphous solid.

NMR (CDCl₃, δ): 1.40 (9H, s), 1.59 (3H, d, J=7 Hz), 3.86 (3H, s), 4.88 (1H, q, J=7 Hz), 5.19 (2H, center of a pair of d, J=12.2 Hz), 6.9–7.4 (8H, m)

MASS: 482 (M+H)⁺

Example 100

The following compounds were prepared by a similar manner to that of Preparation Example 99.

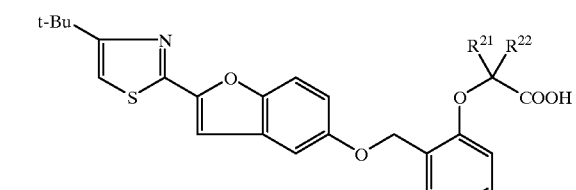

| Example | R²¹ | R²² | R²³ | R²⁴ | Physical Data |
|---|---|---|---|---|---|
| 100-1 | Me | H | OMe | H | IR(Nujol): 3500–2500, 1720, 1260 cm⁻¹ NMR(CDCl₃, δ): 1.40(9H, s), 1.59 (3H, d, J=7.0Hz), 3.88(3H, s), 4.87(1H, q, J=7.0Hz), 5.17(2H, s), 6.91–7.27(7H, m), 7.43(1H, d, J=8.9Hz) MASS: 482(M + H)⁺ |
| | | ((S)-isomer) | | | |
| 100-2 | nPr | H | OMe | H | mp: 111–112.5° C. IR(Nujol): 1728 cm⁻¹ NMR(CDCl₃, δ): 0.86(3H, t, J=7Hz), 1.40(9H, s), 1.58(2H, m), 1.93(2H, m), 3.84(3H, s), 4.90(1H, t, J=6Hz), 5.20(2H, a center of a pair of d, J=12Hz), 6.9–7.28(7H, m), 7.42(1H, d, J=9Hz) MASS: 510(M + H)⁺ |
| 100-3 | Et | H | OMe | H | mp: 117–118° C. IR(Nujol): 1710, 1580 cm⁻¹ NMR(CDCl₃, δ): 1.04(3H, t, J=7.5Hz), 1.40(9H, s), 2.00(2H, dq, J=5.4, 7.5Hz), 3.84(3H, s), 4.87(1H, t, J=5.4Hz), 5.21(2H, s), 6.90–7.03(2H, m), 6.99(1H, s), 7.08(7.14(3H, m), 7.28(1H, s), 7.42(1H, d, J=9Hz) Elemental Analysis Calcd. for C₂₇H₂₉N₁O₆S: C 64.04, H 6.01, N 2.77 Found: C 64.04, H 6.10, N 2.72 |
| 100-4 | Me | Me | OMe | H | mp: 120–120.8° C. NMR(CDCl₃, δ): 1.41(9H, s), 1.51 (6H, s), 3.86(3H, s), 5.09(2H, s), 6.9–7.0(3H, m), 7.1–7.2(1H, m), 7.29(1H, d, J=1Hz), 7.45(1H, d, J=9Hz) MASS: 496.1(N + H)⁺ |
| 100-5 | H | H | OMe | H | mp: 147.5–148° C. IR(Film): 3200–2600, 1720, 1245 cm⁻¹ NMR(CDCl₃, δ): 1.40(9H, s), 3.90 (3H, s), 4.71(2H, s), 5.17(2H, s), 6.93–7.19(18H, m), 7.27(1H, s), 7.43(1H, d, J=9Hz) MASS: 468(M + H)⁺ |
| 100-6 | H | Me | OMe | H | IR(Nujol): 3300–3000, 1720, 1580 cm⁻¹ NMR(CDCl₃, δ): 1.40(9H, s), 1.55 (3H, d, J=8.9Hz), 3.85(3H, s), 4.84(1H, q, J=8.9Hz), 5.15(2H, s), 6.95(1H, s), 6.91–7.43(6H, m), 7.42(1H, d, J=9Hz) MASS: 482(M + H)⁺ |
| | | ((R)-isomer) | | | |
| 100-7 | nPr | H | H | OMe | mp: 137.5–137.9° C. IR(Nujol): 1740, 1610, 1585 cm⁻¹ NMR(CDCl₃, δ): 0.93(3H, t, J=7Hz), 1.40(9H, s), 1.54(2H, m), 2.0(2H, m), 3.78(3H, s), 4.84(1H, t, J=6Hz), 5.03(1H, d, J=11.2Hz), 5.20(1H, d, J=11.2Hz), 5.83 (1H, br s), 6.45(1H, d, J=2.2Hz), 6.54(1H, dd, J=2.2, 8.4Hz), 6.96(1H, s), 7.01(1H, dd, J=2.6, 8.9Hz), 7.18(1H, d, J=2.5Hz), 7.26(1H, s), 7.34(1H, d, J=8.3Hz), 7.42(1H, d, J=8.9Hz) |

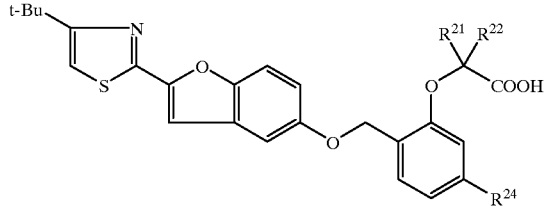

Example 101

To a solution of diphenylmethyl 2-{2-{[2-(4-tert-butylthiazol-2-yl)benzofuran-5-yloxy]methyl}phenoxy}-pentanoate (2.30 g) in a mixed solvent of tetrahydrofuran (30 ml) and methanol (15 ml) was added 1N sodium hydroxide solution (6.8 ml) at room temperature. The solution was stirred for two hours and concentrated under reduced pressure. The residue was diluted with water and acidified with 1N hydrochloric acid and was extracted with ethyl acetate. The organic layer was washed with brine and dried over magnesium sulfate to give 2-{2-{[2-(4-tert-butylthiazol-2-yl)benzofuran-5-yloxy]methyl}phenoxy}pentanoic acid (901 mg).

mp: 135–136° C.
IR (Nujol): 1720 cm$^{-1}$
NMR (CDCl$_3$, δ): 0.95 (3H, t, J=7 Hz), 1.40 (9H, s), 1.58 (2H, m), 2.0 (2H, m), 4.86 (1H, t, J=6 Hz), 5.13 (1H, d, J=12 Hz), 5.33 (1H, d, J=12 Hz), 6.8–7.5 (9H, m)

MASS: 480 (M+H)$^+$

Example 102

The following compounds were prepared by a similar manner to that of Example 101.

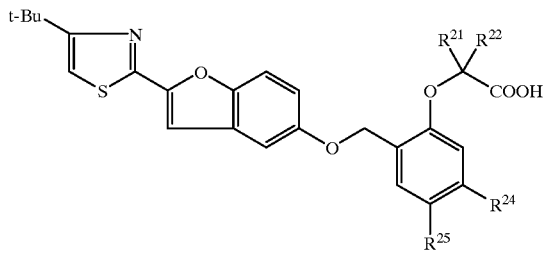

| Example | R$^{21}$ | R$^{22}$ | R$^{24}$ | R$^{25}$ | |
|---|---|---|---|---|---|
| 102-1 | nPr | H | —O–(CH$_2$)$_3$COOH | H | IR(Nujol): 2700, 1715, 1610, 1585, 1505, 1450 cm$^{-1}$<br>NMR(DMSO-d$_6$, δ): 0.86(3H, t, J=7.2Hz), 1.36(9H, s), 1.4–1.5 (2H, m), 1.70–1.95(4H, m), 2.37 (2H, t, J=7.3Hz), 3.90–3.95(2H, m), 4.82(1H, d, J=5.8Hz), 5.04 (1H, d, J=11.7Hz), 5.13(1H, d, J=11.7Hz), 6.44(1H, d, J=2.2Hz), 6.53(1H, dd, J=2.2, 8.3Hz), 7.03 (1H, dd, J=2.2, 8.9Hz), 7.15–7.36 (3H, m), 7.42(1H, s), 7.45(1H, s), 7.58(1H, d, J=8.9Hz)<br>MASS: 582(M + H)$^+$ |
| 102-2 | nPr | H | —O–(CH$_2$)$_4$COOH | H | mp: 155–155.5° C.<br>IR(Nujol): 2700–2500, 1730, 1710, 1610, 1580, 1460, 1380, 1280 cm$^{-1}$<br>NMR(DMSO–d$_6$, δ): 0.86(3H, t, J=7.2Hz), 1.36(9H, s), 1.35–1.5 (2H, m), 1.6–1.99(6H, m), 2.25–2.31(2H, m), 3.90–4.00(2H, m), 4.83(1H, t, J=6.1Hz), 5.04(1H, d, J=11.6Hz), 5.12(1H, d, J=11.6Hz), 6.43(1H, d, J=2.2Hz), 6.53(1H, dd, J=2.2, 8.6Hz), 7.03 (1H, dd, J=2.5, 9.0Hz), 7.30–7.35 (2H, m), 7.42(1H, s), 7.46(1H, s), 7.58(1H, d, J=9.0Hz), 12.6–12.8(2H, br s) |
| 102-3 | nPr | H | —O–(CH$_2$)$_5$COOH | H | mp: 147–147.5° C.<br>IR(Nujol): 2700–2500, 1725, 1705, 1610, 1580, 1500, 1460, 1380 cm$^{-1}$<br>NMR(DMSO-d$_6$, δ): 0.86(3H, t, J=7.4Hz), 1.36(9H, s), 1.35–1.85 (11H, m), 2.33(2H, d, J=7.0Hz), 3.96(2H, br s), 4.82(1H, d, J=6.1Hz), 5.03(1H, d, J=11.8Hz), 5.13(1H, d, J=11.8Hz), 6.42(1H, s), 6.53(1H, d, J=8.5Hz), 7.02 (1H, dd, J=2.4, 9.0Hz), 7.29–7.33 (2H, m), 7.42(1H, s), 7.46(1H, s), 7.58(1H, d, J=9.0Hz)<br>MASS: 610(M + H)$^+$<br>Elemental Analysis Calcd. for.<br>C 65.60, H 6.45, N 2.30<br>Found C 65.43, H 6.55, N 2.26 |
| 102-4 | H | H | —O–(CH$_2$)$_3$COOH | H | IR(Nujol): 3500–3000, 2700–2500, 1700, 1610, 1580, 1500, 1460, 1380 cm$^{-1}$<br>NMR(CDCl$_3$, δ): 1.36(3H, s), 1.93 (2H, quint, J=6.9Hz), 2.38(2H, t, J=7.2Hz), 3.98(2H, t, J=6.9Hz), 4.79(2H, s), 5.08(2H, s), 6.54 (1H, s), 6.58(1H, d, J=2.6Hz), 7.04(1H, dd, J=2.6, 9.0Hz), 7.30–7.35(2H, m), 7.44(1H, d, J=6.5Hz), 7.45(1H, s), 7.58(1H, |

-continued

[Structure: t-Bu-substituted thiazole connected to benzofuran, linked via OCH2 to a phenyl ring bearing OC(R21)(R22)COOH, with R24 and R25 substituents]

| Example | R²¹ | R²² | R²⁴ | R²⁵ | |
|---------|-----|-----|-----|-----|---|
| 102-5 | Et | H | —O—(CH₂)₃COOH | H | d, J=9.0Hz)<br>MASS: 540(M + H)⁺<br>IR(Nujol): 3300, 2500, 1700, 1610, 1585, 1500 cm⁻¹<br>NMR(CDCl₃, δ): 0.98(3H, t, J=7.4Hz), 1.36(9H, s), 1.80–2.00 (4H, m), 2.37(2H, d, J=7.4Hz), 3.95(2H, t, J=6.2Hz), 4.80(1H, t, J=6.2Hz), 5.05(1H, d, J=11.8Hz), 5.13(1H, d, J=11.8Hz), 6.45(1H, d, J=2.0Hz), 6.53(1H, dd, J=2.0, 7.8Hz), 7.03(1H, dd, J=2.6, 9.0Hz), 7.30–7.37(2H, m), 7.42(1H, s), 7.45(1H, s), 7.58 (1H, d, J=9.0Hz) |
| 102-6 | Me | Me | H | H | mp: 175–176° C.<br>IR(Nujol): 1710 cm⁻¹<br>NMR(DMSO-d₆, δ): 1.36(9H, s), 1.54(6H, s), 5.14(2H, s), 6.82 (1H, d, J=8Hz), 7.00(1H, t, J=8Hz), 7.07(1H, dd, J=2, 9Hz), 7.27(1H, s), 7.30(1H, d, J=2Hz), 7.44(1H, s), 7.46(1H, s), 7.50 (1H, m), 7.60(1H, d, J=9Hz), 13.13(1H, br s)<br>MASS: 466(M + H)⁺ |
| 102-7 | nBu | H | H | H | mp: 84–86° C.<br>IR(Nujol): 1720 cm⁻¹<br>NMR(CDCl₃, δ): 0.86(3H, t, J=7Hz), 1.2–1.6(4H, m), 1.40(9H, s), 2.02(2H, m), 4.85(1H, t, J=6Hz), 5.12(1H, d, J=12Hz), 5.23 (1H, d, J=12Hz), 6.9–7.5(9H, m)<br>MASS: 494(M + H)⁺ |
| 102-8 | —(CH₂)₃— | | H | H | mp: 179–180° C.<br>IR(Nujol): 1720, 1580 cm⁻¹<br>NMR(CDCl₃, δ): 1.40(9H, s), 1.96–2.2(2H, m), 2.44–2.6(2H, m), 2.75–2.86(2H, m), 5.12(2H, s), 5.96(1H, m), 6.52(1H, d, J=8Hz), 6.96(1H, s), 7.0–7.06 (2H, m), 7.1–7.2(2H, m), 7.26 (1H, s), 7.4–7.5(2H, m)<br>MASS: 475(M + H)⁺ |
| 102-9 | Et | H | H | H | mp: 161–162° C.<br>IR(Nujol): 1720 cm⁻¹<br>NMR(CDCl₃, δ): 1.01(3H, t, J=7Hz), 1.35(9H, s), 1.92(2H, m), 4.80(1H, t, J=6Hz), 5.20(2H, s), 6.9–7.1(3H, m), 7.2–7.3(2H, m), 7.43(1H, 3), 7.45(1H, s), 7.4(1H, m), 7.60(1H, d, J=9Hz) |
| 102-10 | H | H | H | —O—(CH₂)₃COOH | mp: 147–148° C.<br>IR(Nujol): 1758, 1735, 1650, 1576 cm⁻¹<br>NMR(CDCl₃, δ): 1.38(9H, s), 1.90 (2H, m), 2.36(2H, t, J=7Hz), 3.92 (2H, t, J=6Hz), 5.16(2H, s), 6.82–7.10(4H, m), 7.33(1H, d, J=2.5Hz), 7.44(1H, d, J=3.4Hz), 7.46(1H, s), 7.60(1H, d, J=9Hz)<br>MASS: 540(M + H)⁺ |
| 102-11 | H | H | H | —OCH₂COOH | mp: 157–158° C.<br>IR(Nujol): 1710, 1582 cm⁻¹ |

-continued

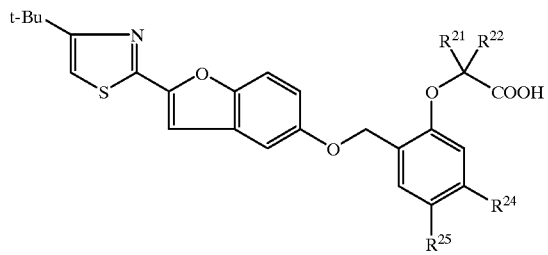

| Example | $R^{21}$ | $R^{22}$ | $R^{24}$ | $R^{25}$ | |
|---|---|---|---|---|---|
| | | | | | NMR(CDCl$_3$, δ): 1.35(9H, s), 4.61(2H, s), 4.74(2H, s), 5.16 (2H, s), 6.8–7.1(4H, m), 7.33 (1H, m), 7.43(1H, s), 7.46(1H, s), 7.60(1H, d, J=9Hz), 12.97 (2H, s) MASS: 512.1(M + H)$^+$ |

Example 103

The following compound was prepared by a similar manner to that of Example 101.

4-{4-{[2-(4-tert-Butylthiazol-2-yl)benzofuran-5-yloxy]methyl}-3-methoxyphenoxy}butyric acid IR (Nujol): 2700, 1705, 1610, 1585, 1500 cm$^{-1}$ NMR (CDCl$_3$, δ): 1.40 (9H, s), 2.05–2.15 (2H, m), 2.60 (2H, t, J=7.0 Hz), 3.84 (3H, s), 4.03 (2H, t, J=6.0 Hz), 5.05 (2H, s), 6.45–6.50 (2H, m), 6.95 (1H, s), 7.01 (1H, dd, J=2.7, 8.9 Hz), 7.13 (1H, d, J=2.7 Hz), 7.26 (1H, s), 7.33 (1H, d, J=8.6 Hz), 7.42 (1H, d, J=8.9 Hz)

MASS: 524 (M+H)$^+$

Example 104

To a solution of 2-{2-{[2-(4-tert-butylthiazol-2-yl)benzofuran-5-yloxy]methyl}-6-methoxyphenoxy}propionic acid (583 mg) in methanol (5 ml) was added 1N sodium hydroxide solution (1.21 ml). The solution was concentrated under reduced pressure and the residue was dissolved in water (5 ml) and lyophilized to give sodium 2-{2-{[2-(tert-butylthiazol-2-yl)benzofuran-5-yloxy]methyl}-6-methoxyphenoxy}propionate (580 mg) as an amorphous solid.

NMR (DMSO-d$_6$, δ): 1.35 (9H, s), 1.37 (3H, d, J=7 Hz), 3.78 (3H, s), 4.62 (1H, q, J=7 Hz), 5.44 (1H, d, J=13 Hz), 5.64 (1H, d, J=13 Hz), 6.92 (3H, s), 7.09 (1H, dd, J=2.5, 9 Hz), 7.37 (1H, d, J=2.5 Hz), 7.45 (2H, s), 7.57 (1H, d, J=9 Hz)

MASS: 504.0 (M+H)$^+$, 526.0 (M+Na)$^+$

Example 105

The following compounds were prepared by a similar manner to that of Example 104.

1) Sodium (S)-2-{2-{[2-(4-tert-butylthiazol-2-yl)-benzofuran-5-yloxy]methyl}-6-methoxyphenoxy}propionate

[α]$_{27}^D$=−5.44° (c=0.91, MeOH)

IR (Nujol): 1580, 1450, 1260 cm$^{-1}$

NMR (CDCl$_3$, δ): 1.19 (3H, d, J=6.9 Hz), 1.40 (9H, s), 3.39 (3H, s), 4.40 (1H, q, J=6.9 Hz), 4.73 (2H, dd, J=12.2 Hz), 6.39 (1H, br d), 6.78–7.00 (5H, m), 7.03 (1H, s), 7.24 (1H, d, J=8.9 Hz)

MASS: 504 (M+H)$^+$, 526 (M+Na)$^+$

2) Sodium (R)-2-{2-{[2-(4-tert-butylthiazol-2-yl)-benzofuran-5-yloxy]methyl}-6-methoxyphenoxy}propionate

[α]$_{27}^D$=+8.92° (c=1.11, MeOH)

IR (Nujol): 3300–3000, 1580, 1450 cm$^{-1}$

NMR (DMSO-d$_6$, δ): 1.35 (9H, s), 1.37 (3H, d, J=6.8 Hz), 3.78 (3H, s), 4.60 (1H, q, J=6.8 Hz), 5.43 (1H, d, J=13.4 Hz), 5.65 (1H, d, J=13.4 Hz), 6.92 (3H, s), 7.10 (1H, dd, J=2.5, 9.0 Hz), 7.37 (1H, dd J=2.5 Hz), 7.43 (1H, s), 7.45 (1H, s), 7.57 (-1H, d, J=9.0 Hz)

MASS: 482 (M+H)$^+$

Example 106

To a solution of 2-{2-{[2-(4-tert-butylthiazol-2-yl)benzofuran-5-yloxy]methyl}-4-methoxyphenoxy}propanoic acid (1.57 g) and 1-hydroxybenzotriazole (0.439 g) in dimethylformamide (20 ml) was added 1-ethyl-3-(3'-dimethylaminopropyl)carbodiimide hydrochloride (0.63 g) at room temperature. The solution was stirred for an hour at the same temperature and was ice-cooled. Then concentrated solution of ammonia (1.1 ml) was added into the solution and the resulting mixture was stirred further for an hour. The mixture was diluted with water and was extracted with ethyl acetate. The organic layer was separated and was washed successively with sodium hydrogen carbonate solution and brine, and was dried over magnesium sulfate. After concentration, the residue (1.50 g) was crystallized with diisopropyl ether, filtered, and dried under reduced pressure to give 2-{2-{[2-(4-tert-butylthiazol-2-yl)benzofuran-5-yloxy]methyl}-6-methoxyphenoxy}propionamide (1.37 g).

mp: 155–156° C.

IR (Nujol): 3450, 3100, 1682, 1580 cm$^{-1}$

NMR (CDCl$_3$, δ): 1.41 (9H, s), 1.49 (3H, d, J=7 Hz), 1.8 (1H, br s), 3.85 (3H, s), 4.83 (1H, q, J=7 Hz), 5.13 (2H, center of a pair of d, J=11.5 Hz), 5.62 (1H, br s), 6.9–7.16 (6H, m), 7.27 (1H, d, J=0.8 Hz), 7.44 (1H, d, J=9 Hz)

MASS: 481 (M+H)$^+$

Example 107

The following compound was prepared by a similar manner to that of Example 106.

2-{[2-(4-tert-Butylthiazol-2-yl)benzofuran-5-yloxy]methyl}-6-methoxyphenoxyacetamide mp: 119.5–121.5° C.

IR (Nujol): 3500–3000, 1680 cm$^{-1}$

NMR (CDCl$_3$, δ): 1.41 (9H, s), 3.88 (3H, s), 4.56 (2H, s), 5.12 (2H, s), 5.64 (1H, br s), 6.93–7.17 (6H, m), 7.28 (1H, s), 7.44 (1H, d, J=9.0 Hz)

MASS: 467 (M+H)$^+$

Example 108

To a solution of 2-{2-{[2-(4-tert-butylthiazol-2-yl)benzofuran-5-yloxy]methyl}phenoxy}pentanoic acid (500 mg) and 1-hydroxybenzotriazole (141 mg) in dimethylformamide (5 ml) was added N-ethyl-N'-(3-dimethylaminopropyl)carbodiimide hydrochloride (200 mg) at room temperature. The solution was stirred for an hour at the same temperature and was ice-cooled. Then concentrated solution of ammonia (0.3 ml) was added into the solution and the resulting mixture was stirred further for an hour. The mixture was diluted with water and was extracted with ethyl acetate. The organic layer was separated and was washed successively with sodium hydrogen carbonate solution and brine, and was dried over magnesium sulfate. Concentration gave 2-{2-{[2-(4-tert-butylthiazol-2-yl)benzofuran-5-yloxy]methyl}phenoxy}-pentanamide (510 mg).

IR (Nujol): 3300–3150, 1685, 1580 cm$^{-1}$

NMR (CDCl$_3$, δ): 0.92 (3H, d, J=7 Hz), 1.41 (9H, s), 1.54 (2H, m), 1.97 (1H, m), 4.75 (1H, t, J=5.8 Hz), 4.96 (1H, d, J=10.8 Hz), 5.35 (1H, d, J=10.8 Hz), 5.45 (1H, br s), 6.77 (1H, br s), 6.9–7.5 (9H, m)

MASS: 479 (M+H)$^+$

Example 109

The following compound was prepared by a similar manner to that of Example 108.

2-{2-{[2-(4-tert-Butylthiazol-2-yl)benzofuran-5-yloxy]methyl}phenoxy}-2-methylpropionamide mp: 148–149° C.

IR (Nujol): 3450, 3150, 1685, 1610, 1585 cm$^{-1}$

NMR (DMSO-d$_6$, δ): 1.36 (9H, s), 1.46 (6H, s), 5.17 (2H, s), 6.88 (1H, d, J=8.2 Hz), 7.0–7.5 (9H, m), 7.62 (1H, d, J=9 Hz)

MASS: 465 (M+H)$^+$

Example 110

The following compounds were prepared by a similar manner to that of Example 20.

1) 2-{2-{[2-(4-tert-Butylthiazol-2-yl)benzofuran-5-yloxy]methyl}-6-methoxyphenoxy}propionitrile IR (CH$_2$Cl$_2$): 1674, 1585, 1480, 1270, 1190 cm$^{-1}$ NMR (CDCl$_3$, δ): 1.41 (9H, s), 1.76 (3H, d, J=6.8 Hz), 3.90 (3H, s), 5.16 (1H, q, J=6.8 Hz), 5.17 (1H, d, J=12 Hz), 5.30 (1H, d, J=12 Hz), 6.9–7.2 (6H, m), 7.30 (1H, d, J=0.7 Hz), 7.43 (1H, d, J=9 Hz)

MASS: 463 (M+H)$^+$

2) {2-{[2-(2-tert-Butylthiazol-2-yl)benzofuran-5-yloxy]methyl}-6-methoxyphenoxy}acetonitrile mp: 80.8–83.4° C.

IR (Nujol): 1585, 1250 cm$^{-1}$

NMR (CDCl$_3$, δ): 1.41 (9H, s), 3.91 (3H, s), 4.89 (2H, s), 5.20 (2H, s), 6.95 (1H, dd, J=2.7, 7.1 Hz), 6.96 (1H, s), 7.02 (1H, dd, J=2.6, 9.0 Hz), 7.1–7.21 (3H, m), 7.28 (1H, s), 7.44 (1H, d, J=9.0 Hz)

MASS: 449 (M+H)$^+$

Example 111

Phosphorus oxychloride (245 mg) was dissolved in dimethylformamide (2 ml) and the solution was ice-cooled. To this solution was added 2-{2-{[2-(4-tert-butylthiazol-2-yl)benzofuran-5-yloxy]methyl}phenoxy]pentanamide (510 mg), and the mixture was stirred for two hours at room temperature. The reaction mixture was concentrated, diluted with water, and extracted with ethyl acetate. The organic layer was washed with brine, dried over magnesium sulfate, and concentrated to give 2-{2-{[2-(4-tert-butylthiazol-2-yl)benzofuran-5-yloxy]methyl}phenoxy}pentanenitrile (453 mg).

IR (Nujol): 1604, 1584 cm$^{-1}$

NMR (CDCl$_3$, δ): 0.98 (3H, d, J=7.4 Hz), 1.50 (9H, s), 1.67 (2H, m), 2.06 (2H, m), 4.87 (1H, d, J=6.5 Hz), 5.08 (1H, d, J=12 Hz), 5.19 (1H, d, J=12 Hz), 6.9–8.0 (9H, m)

MASS: 461 (M+H)$^+$

Example 112

The following compound was prepared by a similar manner to that of Example 111.

2-{2-{[2-(4-tert-Butylthiazol-2-yl)benzofuran-5-yloxy]methyl}phenoxy}-2-methylpropiononitrile mp: 80–81° C.

IR (Nujol): 1600, 1585 cm$^{-1}$

NMR (DMSO-d$_6$, δ): 1.42 (9H, s), 1.75 (6H, s), 5.09 (2H, s), 6.9–7.5 (9H, m)

MASS: 447 (M+H)$^+$

Example 113

The following compounds were obtained according to a similar manner to that of Example 21.

1) 2-(4-tert-Butylthiazol-2-yl)-5-{3-methoxy-2-[1-(1H-tetrazol-5-yl)ethoxy]phenylmethoxy}benzofuran mp: 103–104° C.

IR (Nujol): 2300–2650, 1585 cm$^{-1}$

NMR (CDCl$_3$, δ): 1.42 (9H, s), 1.78 (3H, d, J=6.7 Hz), 3.84 (3H, s), 5.01 (1H, d, J=10.7 Hz), 5.30 (1H, d, J=10.7 Hz), 6.13 (1H, q, J=6.7 Hz), 6.9–7.08 (5H, m), 7.19 (1H, d, J=2.5 Hz), 7.34 (1H, s), 7.45 (1H, d, J=9 Hz)

MASS: 506 (M+H)$^+$

Elemental Analysis Calcd. for C$_{26}$H$_{27}$N$_5$O$_4$S: C, 62.42, H, 6.01, N, 12.82. Found C, 63.48, H, 6.17, N, 12.75.

2) 2-(4-tert-Butylthiazol-2-yl)-5-{[2-(1H-tetrazole-5-yl)methoxy-3-methoxyphenyl-]methoxy}benzofuran mp: 154.4–158.4° C.

IR (Nujol): 3200–2100, 1200 cm$^{-1}$

NMR (CDCl$_3$, δ): 1.41 (9H, s), 3.89 (3H, s), 5.18 (2H, s), 5.64 (2H, s), 6.96–7.04 (5H, m), 7.10 (1H, d, J=7.7 Hz), 7.17 (1H, s), 7.43 (1H, d, J=8.9 Hz)

MASS: 492 (M+H)$^+$

Example 114

2-{2-{[2-(4-tert-Butylthiazol-2-yl)benzofuran-5-yloxy]methyl}phenoxy}pentanenitrile (430 mg) was dissolved in dimethylformamide (5 ml), and sodium azide (364 mg) and ammonium chloride (0.3 g) were added. The mixture was stirred at 120° C. for three hours. The reaction mixture was cooled and poured into water and extracted with ethyl acetate. The aqueous layer was extracted with ethyl acetate again and the combined organic layer was washed with brine and dried over magnesium sulfate. After concentration, the crude product was purified on a silica gel column (15 g) eluting with a mixed solvent of methylene chloride and methanol (2% vol.) to give 2-(4-tert-butylthiazol-2-yl)-5-{2-[1-(1H-tetrazol-5-yl)butoxy]phenylmethoxy}benzofuran (400 mg).

NMR (CDCl$_3$, δ): 0.96 (3H, d, J=7 Hz), 1.41 (9H, s), 1.55 (2H, m), 2.10 (2H, m), 4.90 (1H, d, J=10 Hz), 5.60 (1H, d, J=10 Hz), 5.98 (1H, t, J=6 Hz), 6.97–7.5 (9H, m)

MASS: 504 (M+H)$^+$

Example 115

The following compound was prepared by a similar manner to that of Example 114.

2-(4-tert-Butylthiazol-2-yl)-5-{{2-[1-(1H-tetrazol-5-yl)-1-methylethoxy]phenyl}methoxy}benzofuran NMR (CDCl$_3$, δ): 1.41 (9H, s), 1.92 (6H, s), 5.17 (2H, s), 6.62 (1H, d, J=8 Hz), 7.0–7.3 (6H, m), 7.45 (2H, m)

MASS: 490 (M+H)$^+$

Example 116

Hydroxyamine hydrochloride (174 mg) was dissolved in dimethylsulfoxide (2 ml) and 28% solution of sodium methoxide in methanol (0.125 g) was added into it. The mixture was stirred for ten minutes at room temperature. 2-{2-{[2-(4-tert-butylthiazol-2-yl)benzofuran-5-yloxy]methyl}phenoxy}-pentanenitrile (224 mg) was added into the solution and the resulting mixture was stirred at 80° C. for an hour. The reaction mixture was collected and diluted with water and was extracted with ethyl acetate. The organic layer was washed with brine and was dried over magnesium sulfate. Concentration gave 2-{2-{[2-(4-tert-butylthiazol-2-yl)benzofuran-5-yloxy]methyl}phenoxy}pentanamide oxime as an amorphous solid (266 mg).

IR (Nujol): 3250, 1660, 1585 cm$^{-1}$

NMR (CDCl$_3$, δ): 0.93 (3H, t, J=7 Hz), 1.41 (9H, s), 1.50 (2H, m), 1.75–2.0 (2H, m), 4.73 (1H, m), 4.81 (2H, br s), 5.03 (1H, d, J=11.3 Hz), 5.27 (1H, d, J=11.3 Hz), 6.96–7.1 (4H, m), 7.16 (1H, d, J=2 Hz), 7.2–7.3 (3H, m), 7.4–7.5 (2H, m)

MASS: 494 (M+H)$^+$

Example 117

The following compound was prepared by a similar manner to that of Example 116.

2-{2-{[2-(4-tert-Butylthiazol-2-yl)benzofuran-5-yloxy]methyl}phenoxy}-2-methylpropionamide oxime NMR (CDCl$_3$, δ): 0.93 (3H, t, J=7 Hz), 1.41 (9H, s), 1.58 (6H, m), 4.96 (2H, br s), 5.12 (2H, s), 6.96–7.1 (4H, m), 7.0–7.5 (9H, m)

MASS: 480 (M+H)$^+$

Example 118

2-{2-{[2-(4-tert-Butylthiazol-2-yl)benzofuran-5-yloxy]methyl}phenoxy}pentanamide oxime (240 mg) and triethylamine (61 mg) were dissolved in tetrahydrofuran (3 ml). To this solution was added a solution of ethyl chloroformate (65 mg) dissolved in tetrahydrofuran (1 ml) under ice-cooling. The reaction mixture was stirred for fifteen minutes, filtered, and concentrated. The resulting material was dissolved in xylene (4 ml) and 1.8-diazabicyclo[5.4.0]undec-7-ene (152 mg) was added. The mixture was stirred at 50° C. for three hours. The mixture was cooled, diluted with toluene, and washed successively with 0.5N hydrochloric acid and brine, and dried over magnesium sulfate. The crude material was purified on a silica gel column eluting with a mixed solvent of methylene chloride and methanol (1% vol.) to give partially purified product which was again purified on a silica gel column eluting with a mixed solvent of toluene and ethyl acetate (6:1) to give 3-{1-{2-{[2-(4-tert-butylthiazol-2-yl)benzofuran-5-yloxy]methyl}phenoxy}butyl}-1,2,4-oxadiazoline-5-one (120 mg).

IR (Nujol): 1770, 1585 cm$^{-1}$

NMR (CDCl$_3$, δ): 0.96 (3H, t, J=7 Hz), 1.41 (9H, s), 1.53 (2H, m), 1.7–2.1 (2H, m), 4.85 (1H, d, J=10.2 Hz), 5.93 (1H, t, J=7 Hz), 5.46 (1H, d, J=10.2 Hz), 7.0–7.5 (9H, m), 10.1 (1H, br s)

MASS: 520 (M+H)$^+$

Example 119

The following compound was prepared in a similar manner to that of Example 118.

3-{1-{2-{[2-(4-tert-Butylthiazol-2-yl)benzofuran-5-yloxy]methyl}phenoxy}-1-methylethyl}-1,2,4-oxadiazolin-5-one mp: 120–122° C.

IR (Nujol): 1772, 1585 cm$^{-1}$

NMR (CDCl$_3$, δ): 1.40 (9H, s), 1.76 (6H, s), 5.12 (2H, s), 6.9–7.5 (9H, m), 10.2 (1H, br s)

MASS: 506 (M+H)$^+$

Example 120 tert-Butyl 2-{[2-(4-tert-butylthiazol-2-yl)benzofuran-5-yloxy]methyl}-4-[3-(ethoxycarbonyl)propoxy]phenoxyacetate (200 mg) was dissolved in a mixed solvent of acetnitrile (10 ml) and acetone (1 ml) and methanesulfonic acid (62 mg) was added. The resulting solution was stirred at 80° C. for two hours. The reaction mixture was concentrated and diluted with water and neutralized with sodium hydrogen carbonate solution. The mixture was acidified with 1N hydrochloric acid and extracted with ethyl acetate. The organic layer was washed with brine and was dried over magnesium sulfate. After concentration, the product was crystallized with a mixed solvent of diisopropyl ether and n-hexane (1:2), filtered and dried to give 2-{[2-(4-tert-butylthiazol-2-yl)benzofuran-5-yloxy]methyl}-4-[3-(ethoxycarbonyl)propoxy]-phenoxyacetic acid (117 mg).

mp: 102–103° C.

IR (Nujol): 1750 (sh), 1730 cm$^{-1}$

NMR (CDCl$_3$, δ): 1.24 (3H, t, J=7 Hz), 1.48 (9H, s), 2.07 (2H, m), 2.49 (2H, t, J=7 Hz), 3.95 (2H, t, J=7 Hz), 4.13 (2H, q, J=7 Hz), 4.71 (2H, s), 5.18 (2H, s), 6.79 (2H, d, J=2 Hz), 6.96 (1H, s), 7.03 (1H, dd, J=2.4, 9 Hz), 7.19 (1H, d, J=2.4 Hz), 7.26 (1H, d, J=2.4 Hz), 7.41 (1H, d, J=9 Hz)

MASS: 568 (M+H)$^+$

Example 121

Sodium hydride (60% in mineral oil, 7.79 g) was added into a solution of 5-methoxy-1H-indazole-3-carboxylic acid (17.0 g) in N,N-dimethylformamide (400 ml) at room temperature under nitrogen atmosphere. After 30 minutes, 4-tert-butyl-2-[5-(chloromethyl)benzofuran-2-yl]thiazole (29.76 g) was added to the solution over 5 minutes. After being stirred continuously for 3 hours at 45° C., the reaction mixture was poured into water (2 l) and the reaction vessel was washed with water (200 ml). After combining the washing mixture to the aqueous mixture, the resulting mixture was made acidic with 10% hydrochloric acid aqueous solution (500 ml) and stirred vigorously for one hour. The precipitate was collected by filtration, washed with water and air-dried for one day. The crude product was washed with a mixture of isopropyl alcohol and isopropylethyl ether (7:3) and dried in vacuo to give 5-methoxy-1-{[2-(4-tertbutylthiazol-2 -yl)benzofuran-5-yl]methyl}indazole-3-carboxylic acid (36.5 g).

IR (Nujol): 2900–2300, 1685, 1660, 1480, 1460, 1380 cm$^{-1}$

NMR (DMSO-d$_6$, δ): 1.35 (9H, s), 3.82 (3H, s), 5.84 (2H, s), 7.12 (1H, dd, J=2.4 and 9.0 Hz), 7.35 (1H, dd, J=1.8 and 8.6 Hz), 7.44 (1H, s), 7.45 (1H, d, J=2.4 Hz), 7.48 (1H, d, J=8.5 Hz), 7.64 (1H, s), 7.67 (1H, d, J=8.6 Hz), 7.79 (1H, d, J=9.0 Hz), 12.80–13.20 (1H, br s)

Example 122

A mixture of 5-methoxy-1-{[2-(4-tert-butylthiazol-2-yl) benzofuran-5-yl]methyl}indazole-3-carboxylic acid (3.0 g) and concentrated sulfuric acid (0.3 ml) in methanol (30 ml) was stirred under reflux for 6 hours. After being cooled to room temperature and stored for overnight, the precipitate was collected by filtration and washed with isopropyletyl ether to give methyl 5-methoxy-1-{[2-(4-tert-butylthiazol-2-yl)benzofuran-5-yl]methyl}indazole-3-carboxylate.

IR (Nujol): 1700, 1495, 1480, 1460 cm$^{-1}$

NMR (CDCl$_3$, δ): 1.41 (9H, s), 3.89 (3H, s), 4.06 (3H, s), 5.76 (2H, s), 6.98 (1H, s), 7.20 (1H, dd, J=2.4 and 8.7 Hz), 7.19–7.28 (2H, m), 7.35 (1H, s), 7.46 (1H, d, J=8.7 Hz), 7.49 (1H, s), 7.59 (1H, d, J=2.1 Hz)

Example 123

The following compound was prepared by a similar manner to that of Example 19.

5-Methoxy-1-{[2-(4-tert-butylthiazol-2-yl)benzofuran-5-yl]methyl}indazole-3-carboxamide.

IR (Nujol): 3500–3000, 1675 cm$^{-1}$

NMR (DMSO-d$_6$, δ): 1.34 (9H, s), 3.80 (3H, s), 5.81 (2H, s), 7.09 (1H, dd, J=2.3 and 9.2 Hz), 7.34 (1H, dd, J=1.8 and 8.6 Hz), 7.41 (1H, s), 7.49 (1H, s), 7.51 (1H, s), 7.56 (1H, d, J=2.3 Hz), 7.61 (1H, d, J=1.8 Hz), 7.66 (1H, br s), 7.66 (1H, d, J=8.6 Hz), 7.74 (1H, d, J=9.2 Hz)

MASS: 461 (M+H)$^+$

Example 124

The following compound was prepared by a similar manner to that of Example 44.

5-Methoxy-1-{[2-(4-tert-butylthiazol-2-yl)benzofuran-5-yl]methyl}indazole-3-carboxamide Example 125

The following compound was prepared by a similar manner to that of Example 20.

1-{[2-(4-tert-Butylthiazol-2-yl)benzofuran-5-yl]methyl}-5-methoxyindazole-3-carbonitrile Example 126

Aqueous 1N sodium hydroxide solution (27.8 ml) was added dropwise to a suspension of 5-{1-{[2-(4-tert-butylthiazol-2-yl)benzofuran-5-yl]methyl}-5-methoxy-1H-indazol-3-yl}-1H-tetrazole (13.5 g) in acetonitrile (150 ml). The mixture was warmed at 45° C. and stirred until to be dissolved completely. The solution was collected at room temperature and washed with a mixture of acetonitrile and isopropylether (1:1) to give 5-{1-[2-(4-tert-butylthiazol-2-yl)benzofuran-5-yl]methyl-5-methoxy-1H-indazol-3-yl}-1H-tetrazole sodium salt as a colorless powder.

mp: >250° C.

IR (Nujol): 3600–3300, 1640, 1630, 1540, 1510, 1380 cm$^{-1}$

NMR (DMSO-d$_6$, δ): 1.34 (9H, s), 3.84 (3H, s), 5.77 (2H, s), 7.04 (1H, dd, J=2.5 and 9.1 Hz), 7.36 (1H, dd, J=1.6 and 8.8 Hz), 7.46 (1H, s), 7.49 (1H, s), 7.61 (1H, s), 7.61 (1H, d, J=1.6 Hz), 7.63 (1H, d, J=9.1 Hz), 7.83 (1H, d, J=2.5 Hz)

We claim:
1. A compound of the formula:

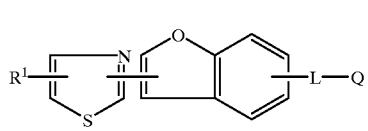

(I)

wherein R$^1$ is lower alkyl,
L is single bond or lower alkylene optionally substituted with aryl, oxo or hydroxy, and
Q is a group of the following formula:

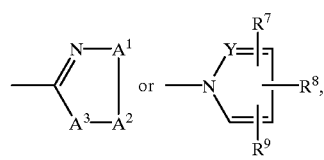

or lower alkoxy substituted with phenyl, wherein phenyl group is substituted with one or more of the same or different alkoxy group(s) optionally substituted with cyano; lower alkoxycarbonyl; benzyloxycarbonyl; diphenylmethyloxycarbonyl; carboxy; acyl; lower alkylene; a heterocyclic group consisting of tetrazolyl and oxadiazolinyl optionally substituted with oxo; or amidino optionally substituted with hydroxy or lower alkoxy;
wherein —A$^1$—A$^2$—A$^3$— is (a) —CR$^2$=CR$^3$—X—, (b) —N=N—NR$^4$— or (c) —NR$^5$—N=N—,
X is S, O or NR$^6$,
R$^2$ and R$^3$ are each independently hydrogen or substituent selected from the group consisting of acyl; carboxy; protected carboxy; aryl; and lower alkyl optionally substituted with acyl, carboxy, protected carboxy, halogen, tetrazolyl or cyano,
R$^4$ is hydrogen or lower alkyl optionally substituted with aryl which is optionally substituted with carboxy or protected carboxy, and
R$^5$ and R$^6$ are each same as R$^4$, Y is CR$^{10}$ or N,
R$^7$ and R$^8$ form a ring together with the vicinal carbon atoms to which they are attached, and R$^7$ and R$^8$ are represented by the structure:

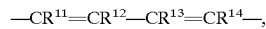

R$^9$ is hydrogen; cyano; acyl; carboxy; protected carboxy; tetrazolyl; lower alkyl optionally substituted with acyl, carboxy or protected carboxy; or lower alkenyl substituted with carboxy or protected carboxy,
R$^{10}$ is same as R$^9$, and
R$^{11}$, R$^{12}$, R$^{13}$ and R$^{14}$ are each independently hydrogen or substituent selected from the group consisting of acyl; carboxy; protected carboxy; halogen; nitro; amino; hydroxy; lower cycloalkoxy; lower alkyl optionally substituted with halogen, hydroxy, acyl, carboxy or protected carboxy; and lower alkoxy optionally substituted with cyano, tetrazolyl, acyl, carboxy, protected carboxy, lower alkylene, or aryl optionally substituted with halogen, acyl, carboxy or protected carboxy, and its salts.

2. The compound of claim 1, which has the following formula

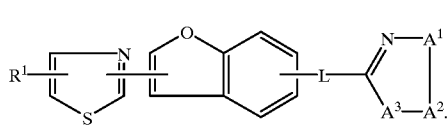

(II)

3. The compound of claim 1, which has the following formula:

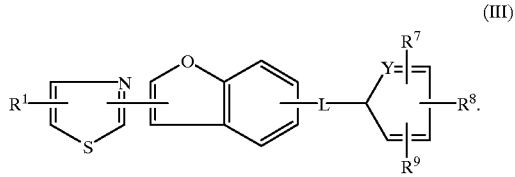

(III)

4. The compound of claim 3, wherein
Y is N,
$R^9$ is tetrazolyl, and one of $R^{11}$, $R^{12}$, $R^{13}$ and $R^{14}$ is lower alkoxy and the others are each hydrogen.

5. The compound of claim 1, wherein
L is single bond, and
Q is lower alkoxy substituted with phenyl, wherein
phenyl group is substituted with one or more of the same or different alkoxy group(s) optionally substituted with cyano; lower alkoxycarbonyl; benzyloxycarbonyl; diphenylmethyloxycarbonyl; carboxy; acyl; lower alkylene; a heterocyclic group consisting of tetrazolyl and oxadiazolinyl optionally substituted with oxo; or amidino optionally substituted with hydroxy or lower alkoxy.

6. A compound of claim 5, wherein
Q is lower alkoxy substituted with phenyl, wherein
phenyl group is substituted with lower alkoxy and lower alkoxy substituted with carboxy.

7. A pharmaceutical composition comprising a compound of claim 1, as an active ingredient, in association with a pharmaceutically acceptable, substantially non-toxic carrier or excipient.

8. A method of the therapeutic treatment and/or prevention of allergy or inflammation which comprises administering an effective amount of a compound of claim 1 to human beings or animals.

* * * * *